US011988667B2

(12) United States Patent
Nakata et al.

(10) Patent No.: US 11,988,667 B2
(45) Date of Patent: May 21, 2024

(54) FLUORESCENT COMPOUND AND FLUORESCENT LABELED BIOLOGICAL SUBSTANCE USING THE SAME

(71) Applicant: FUJIFILM Corporation, Tokyo (JP)

(72) Inventors: Hiyoku Nakata, Kanagawa (JP); Kousuke Watanabe, Kanagawa (JP); Akihiro Asakura, Kanagawa (JP); Keiko Makita, Kanagawa (JP); Yoshinori Kanazawa, Kanagawa (JP); Kazuhei Kaneko, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 746 days.

(21) Appl. No.: 17/105,638

(22) Filed: Nov. 27, 2020

(65) Prior Publication Data

US 2021/0088526 A1 Mar. 25, 2021

Related U.S. Application Data

(63) Continuation of application No. PCT/JP2019/021770, filed on May 31, 2019.

(30) Foreign Application Priority Data

Jun. 1, 2018 (JP) ................................ 2018-106460
Feb. 15, 2019 (JP) ................................ 2019-025958

(51) Int. Cl.

| | |
|---|---|
| ***C09K 11/06*** | (2006.01) |
| ***C09B 23/06*** | (2006.01) |
| ***G01N 21/64*** | (2006.01) |
| ***G01N 33/58*** | (2006.01) |

(52) U.S. Cl.

CPC ........... *G01N 33/582* (2013.01); *C09B 23/06* (2013.01); *C09K 11/06* (2013.01); *G01N 21/6428* (2013.01); *C09K 2211/1029* (2013.01); *G01N 2021/6439* (2013.01)

(58) Field of Classification Search

CPC ................................ C09K 11/06; C09B 23/06
See application file for complete search history.

(56) References Cited

U.S. PATENT DOCUMENTS

| | | | |
|---|---|---|---|
| 8,778,510 | B2 | 7/2014 | Okuda et al. |
| 9,616,140 | B2 | 4/2017 | Pinchuk et al. |
| 2009/0192298 | A1 | 7/2009 | Burgess |
| 2018/0134952 | A1 | 5/2018 | Ichihashi et al. |
| 2020/0347292 | A1 | 11/2020 | Ichihashi et al. |
| 2020/0354629 | A1 | 11/2020 | Kaneko et al. |

FOREIGN PATENT DOCUMENTS

| | | |
|---|---|---|
| CN | 106946919 | 7/2017 |
| CN | 106947469 | 7/2017 |
| JP | 2010184880 | 8/2010 |
| JP | 2013032297 | 2/2013 |

(Continued)

OTHER PUBLICATIONS

"Office Action of Japan Counterpart Application" with English translation thereof, issued on Aug. 31, 2021, p. 1-p. 11.
Rebecca Clarke et al: "Circularly Polarised Luminescence from Helically Chiral " Confused" N, N, O,C -Boron-Chelated Dipyrromethenes (BODIPYs)", ChemPhotoChem, Aug. 2017, pp. 513-517.
"Search Report of Europe Counterpart Application", issued on Jun. 30, 2021, pp. 1-8.
"International Search Report (Form PCT/ISA/210) of PCT/JP2019/021770," mailed on Aug. 13, 2019, with English translation thereof, pp. 1-5.

(Continued)

*Primary Examiner* — Shawquia Jackson
(74) *Attorney, Agent, or Firm* — JCIPRNET

(57) ABSTRACT

Provided are any one of the following fluorescent compounds and a fluorescent labeled biological substance having this fluorescent compound.

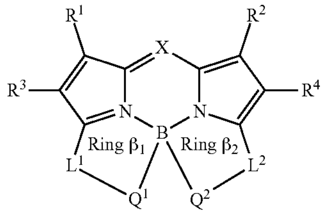

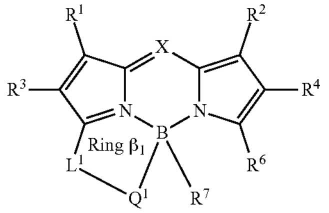

X represents $CR^5$ or N, and $R^1$ to $R^7$, $Q^1$, $Q^2$, $L^1$, and $L^2$ each represent a specific group.
a ring $\beta_1$ and a ring $\beta_2$ are a 5- to 8-membered ring,
At least one of $R^1$ to $R^7$, $L^1$, $L^2$, $Q^1$, or $Q^2$ has a specific hydrophilic group.
However, in a case where the ring $\beta_1$ and the ring $\beta_2$ are a 6-membered ring, and $L^1$ and $L^2$ are an arylene group, $R^5$ is not an aryl group substituted with a linear alkyl group having 18 or more carbon atoms. In addition to the regulation of the ring $\beta_1$, the ring $\beta_2$, $L^1$, and $L^2$, in a case where $R^5$ has a substituent having a dipyrromethene boron complex structure, the dipyrromethene boron complex structure has a structure in which a dipyrromethene skeleton is coordinately bonded to a boron atom in the tridentate or tetradentate coordination.

18 Claims, No Drawings

(56) References Cited

FOREIGN PATENT DOCUMENTS

| | | |
|---|---|---|
| JP | 2016193907 | 11/2016 |
| WO | 2010098098 | 9/2010 |
| WO | 2016190283 | 12/2016 |
| WO | 2019155911 | 8/2019 |

OTHER PUBLICATIONS

"Written Opinion of the International Searching Authority (Form PCT/ISA/237) of PCT/JP2019/021770," mailed on Aug. 13, 2019, with English translation thereof, pp. 1-9.

Chusaku Ikeda, et al., "Convenient and highly efficient synthesis of boron-dipyrrins bearing an arylboronate center," Tetrahedron Letters, vol. 50, Feb. 2009, pp. 3349-3351.

Masaki Yamamura, et al., "A facile and high-yield formation of dipyrrin-boronic acid dyads and triads: a light-harvesting system in the visible region based on the efficient energy transfer," Organic & Biomolecular Chemistry, Jan. 2015, pp. 2574-2581.

Dumitru Sirbu, et al., "One-Pot Synthesis of a Mono-O,B,N-strapped BODIPY Derivative Displaying Bright Fluorescence in the Solid State," Organic Letters, Mar. 2017, pp. 1626-1629.

Na Chen, et al., "Sterically Protected N2O-Type Benzopyrromethene Boron Complexes from Boronic Acids with Intense Red/Near-Infrared Fluorescence," Organic Letters, Mar. 2017, pp. 2026-2029.

Zhaoyang Ding, et al., "Thermo-Responsive Fluorescent Polymers with Diverse LCSTs for Ratiometric Temperature Sensing through FRET," Polymers, Mar. 2018, pp. 1-10.

FLUORESCENT COMPOUND AND FLUORESCENT LABELED BIOLOGICAL SUBSTANCE USING THE SAME

CROSS-REFERENCE TO RELATED APPLICATIONS

This application is a Continuation of PCT International Application No. PCT/JP2019/021770 filed on May 31, 2019, which claims priority under 35 U.S.C. § 119 (a) to Japanese Patent Application No. 2018-106460 filed in Japan on Jun. 1, 2018 and Japanese Patent Application No. 2019-025958 filed in Japan on Feb. 15, 2019. Each of the above applications is hereby expressly incorporated by reference, in its entirety, into the present application.

BACKGROUND OF THE INVENTION

1. Field of the Invention

The present invention relates to a fluorescent compound and a fluorescent labeled biological substance using the fluorescent compound.

2. Description of the Related Art

Bioimaging technology for analyzing the dynamics and functions of living body molecules, cells, tissues, and the like in the living body has been utilized for the diagnosis of various diseases. In recent years, in vivo fluorescence imaging, which visualizes and observes a specific portion of a living body with a fluorescent dye, is expected as a new technique for living body observation.

In this in vivo fluorescence imaging, an organic fluorescent dye is generally used. However, the organic fluorescent dye has low light resistance and deteriorates by irradiation with excitation light, and thus the observation of the target living body may not be sufficiently performed.

A dipyrromethene boron complex is known as a fluorescent dye that has a high quantum yield and exhibits sharp emission characteristics and thus is used in various fields.

For example, JP2016-193907A discloses a fluorescent lipid ether compound that is expected to be used for tumor diagnosis and discloses a dipyrromethene boron complex as an example of a fluorophore in the fluorescent lipid ether compound. In addition, US2009/0192298A discloses an energy transfer cassette through a chemical bond and discloses a dipyrromethene boron complex as an example of a donor or an acceptor of this cassette.

SUMMARY OF THE INVENTION

However, the dipyrromethene boron complex is generally poor water solubility and has low light resistance. Accordingly, in order to apply the dipyrromethene boron complex to a tool for living body observation, such as in vivo fluorescence imaging, it is necessary to impart both water solubility and light resistance to the dipyrromethene boron complex at a high level. From this viewpoint, the inventors of the present invention performed studies and found that although dipyrromethene boron complexes having high water solubility have been reported, such dipyrromethene boron complexes having high water solubility are easily discolored and still have poor light resistance.

An object of the present invention is to provide a fluorescent compound having a dipyrromethene boron complex structure and realizing both sufficient hydrophilicity required for in vivo fluorescence imaging and excellent light resistance. In addition, another object of the present invention is to provide a fluorescent labeled biological substance obtained by bonding the fluorescent compound to a biological substance.

The inventors of the present invention speculated that the discoloring of the existing dipyrromethene boron complexes having water solubility is mainly due to photolysis involving the boron atom by reactive oxygen species. Under this speculation, the inventors of the present invention further introduced a specific hydrophilic group into a compound having a specific structure in which a compound having a dipyrromethene skeleton into which a substituent had been introduced was coordinated to a boron atom as a tridentate ligand or a tetradentate ligand and have found that discoloring is successfully reduced and a fluorescent dye having excellent hydrophilicity can be obtained. The present invention has been completed through further studies based on these findings.

That is, the above objects of the present invention have been achieved by the following means.

<1> A fluorescent compound represented by Formula (1) or Formula (4).

Formula (1)

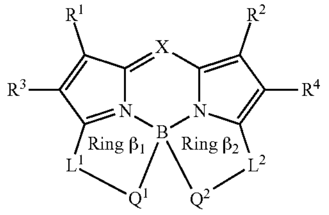

Formula (4)

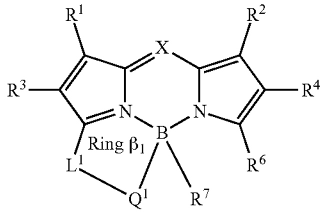

In the formula, X represents $CR^5$ or N.

$R^1$ to $R^6$ represent a halogen atom, a cyano group, or a group represented by Formula (A).

$R^7$ represents an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, or a halogen atom. Here, $R^6$ and $R^7$ do not bond to each other to form a ring.

$Q^1$ and $Q^2$ represent a group represented by any one of Formulae (1-1) to (1-3).

$L^1$ and $L^2$ represent an alkylene group, an alkenylene group, an arylene group, a heteroarylene group, a cycloalkylene group, a cycloalkenylene group, a divalent aliphatic heterocyclic group, a group represented by any one of Formulae (1-1) to (1-8), or a linking group formed by combining two to four of these groups.

A ring $\beta_1$ and a ring $\beta_2$ are a 5- to 8-membered ring.

Here, at least one of $R^1$ to $R^7$, $L^1$, $L^2$, $Q^1$, or $Q^2$ has at least one of a carboxy group or a salt thereof, a sulfo group or a salt thereof, a phosphono group or a salt thereof, an onio group, or a polyamino acid residue.

In a case where X is $CR^5$, where $R^5$ is a group represented by Formula (A), the ring $\beta_1$ and the ring $\beta_2$ are a 6-membered ring, and $L^1$ and $L^2$ are an arylene group, (a) there is no case in which $L^3$ is a single bond and $R^{111}$ is an aryl group having a linear alkyl group having 18 or more carbon atoms, as a substituent, and (b) there is no case in which $L^3$ is arylene group and $R^{111}$ is a linear alkyl group having 18 or more carbon atoms. Further, in a case where X is $CR^5$, where $R^5$ is a group represented by Formula (A), the ring $\beta_1$ and the ring 132 are a 6-membered ring, $L^1$ and $L^2$ are an arylene group, and $R^{111}$ has a substituent having a dipyrromethene boron complex structure, the dipyrromethene boron complex structure has a structure in which a dipyrromethene skeleton is coordinately bonded to a boron atom in the tridentate or tetradentate coordination.

$*L^3\text{-}R^{111}$ Formula (A)

In the formula, $L^3$ represents a single bond or a linking group formed by combining one or two or more of an alkylene group, an arylene group, and a group represented by any one of Formulae (1-1) to (1-8).

$R^{111}$ represents a hydrogen atom, an alkyl group, an alkenyl group, an alkynyl group, an aryl group, a heteroaryl group, or a monovalent aliphatic heterocyclic group.

* represents a bonding portion.

Formula (1-1)

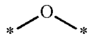

Formula (1-2)

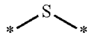

Formula (1-3)

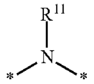

Formula (1-4)

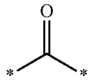

Formula (1-5)

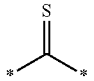

Formula (1-6)

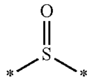

Formula (1-7)

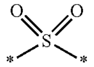

Formula (1-8)

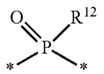

In the formula, $R^{11}$ and $R^{12}$ represent a hydrogen atom or a substituent.

* represents a bonding portion.

<2> The fluorescent compound according to <1>, in which both the $Q^1$ and the $Q^2$ are a group represented by Formula (1-1).

<3> The fluorescent compound according to <1> or <2>, in which the X is $CR^5$, where $R^5$ is represented by Formula (A), and $L^3$ and $R^{111}$ in Formula (A) satisfy the following.

The $L^3$ is a single bond, the $R^{111}$ is a hydrogen atom, an alkyl group, an alkenyl group, an alkynyl group, an aryl group, or a heteroaryl group, or the $L^3$ is a group formed by combining one or two or more of an alkylene group, an arylene group, and a group represented by any one of Formulae (1-1) to (1-8), and the $R^{111}$ is a hydrogen atom.

<4> The fluorescent compound according to any one of <1> to <3>, in which at least one of the $R^3$ or the $R^4$ is a group containing a carboxy group or a salt thereof, a group containing a sulfo group or a salt thereof, a group containing a phosphono group or a salt thereof, a group containing an onio group, or a group containing a polyamino acid residue.

<5> The fluorescent compound according to any one of <1> to <4>, in which at least one of the $R^3$ or the $R^4$ is a carboxy group or a salt thereof, a sulfo group or a salt thereof, or a phosphono group or a salt thereof.

<6> The fluorescent compound according to any one of <1> to <5>, in which at least one of the $R^3$ or the $R^4$ is a sulfo group or a salt thereof.

<7> The fluorescent compound according to any one of <1> to <6>, in which the $L^1$ and the $L^2$ are an alkylene group, an ethenylene group, an arylene group, a heteroarylene group, a cycloalkylene group, or a divalent aliphatic heterocyclic group, or a linking group formed by combining two of these groups, and the ring Pi and the ring $\beta_2$ are a 6- to 8-membered ring.

<8> The fluorescent compound according to <1>, wherein the $Q^1$ and the $Q^2$ are a group represented by Formula (1-1), the $R^1$ to $R^4$ are represented by Formula (A), where the $L^3$ is a single bond or $—SO_3—$, and the $R^{111}$ is a hydrogen atom, the $R^6$ is represented by Formula (A), where the $L^3$ is a single bond, an arylene group or a group represented by Formula (1-1), or, a group formed by combining an arylene group and a group represented by Formula (1-1), and, the $R^{111}$ is a hydrogen atom or an alkyl group, the $R^7$ is a hydroxy group, the $L^1$ and the $L^2$ is an alkylene group or an arylene group, or, a group formed by combining an alkylene group and an arylene group, the ring $\beta_1$ and the ring $\beta_2$ are a 7-membered ring, the X is $CR^5$, where $R^5$ is represented by Formula (A), and the $L^3$ and the $R^{111}$ in Formula (A) satisfy the following (a) or (b);

(a) the $L^3$ is a single bond, and, the $R^{111}$ is an aryl group (b) the $L^3$ is an alkylene group, an arylene group, a group represented by Formula (1-1), a group represented by Formula (1-3), a group represented by Formula (1-4), or a group represented by Formula (1-7), or, a group formed by combining two or more of an alkylene group, an arylene group, a group represented by Formula (1-1), a group represented by Formula (1-3), a group represented by Formula (1-4), or a group represented by Formula (1-7), and, the $R^{111}$ is a hydrogen atom.

wherein, in the fluorescent compound represented by Formula (1), at least one of the $R^3$ and the $R^4$ is a sulfo group or a salt thereof, or, at least one of the $R^1$ to $R^5$ includes two or more of a carboxy group or a salt thereof, a sulfo group or a salt thereof, a phosphono group or a salt thereof, an onio group, or a polyamino acid residue, wherein, in the fluorescent compound represented by Formula (4), at least one of the $R^3$ and the $R^4$ is a sulfo group or a salt thereof, or, at least one of the $R^1$ to $R^7$ includes two or more of a carboxy group or a salt thereof, a sulfo group or a salt thereof, a phosphono group or a salt thereof, an onio group, or a polyamino acid residue.

<9> The fluorescent compound according to any one of <1> to <7>, in which the fluorescent compound is represented by Formula (2) or Formula (5), Formula (2)

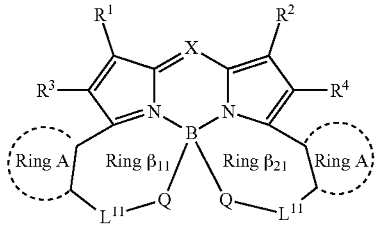

Formula (5)

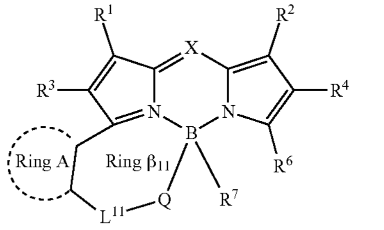

In the formula, X represents $CR^5$ or N.

$R^1$ to $R^7$ and Q respectively have the same meanings as $R^1$ to $R^7$ and $Q^1$ in Formula (1) or (4).

A ring A represents a hydrocarbon ring or a heterocycle.

$L^{11}$ represents a single bond or an alkylene group, an alkenylene group, an arylene group, a heteroarylene group, a cycloalkylene group, a divalent aliphatic heterocyclic group, or a group represented by any one of Formulae (1-1) to (1-8), or a linking group formed by combining two of these groups.

Here, a ring $\beta_{11}$ and a ring $\beta_{21}$ are a 6- to 8-membered ring.

<10> The fluorescent compound according to any one of <1> to <8>, in which the fluorescent compound is represented by Formula (3) or Formula (6).

Formula (3)

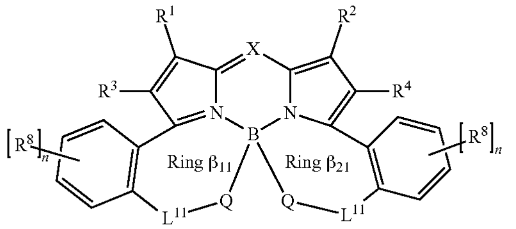

Formula (6)

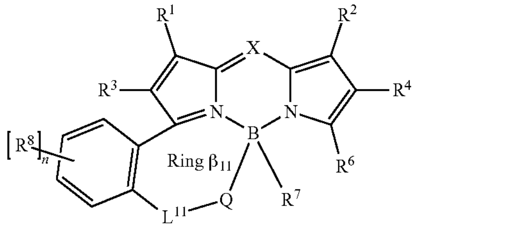

In the formula, X represents $CR^5$ or N.

$R^1$ to $R^7$ and Q respectively have the same meanings as $R^1$ to $R^7$ and $Q^1$ in Formula (1) or (4), and $L^{11}$ has the same meaning as $L^{11}$ in Formula (2) or (5).

$R^8$ represents a substituent, and n is an integer of 0 to 4.

Here, a ring $\beta_{11}$ and a ring $\beta_{21}$ are a 6- to 8-membered ring.

<11> The fluorescent compound according to <10>, wherein the fluorescent compound is represented by Formula (3), wherein the X is $CR^5$, where $R^5$ is represented by Formula (A) and the $L^3$ in Formula (A) is a single bond, an alkylene group, an arylene group, a group represented by Formula (1-1), a group represented by Formula (1-3), a group represented by Formula (1-4), or a group represented by Formula (1-7), or, a group formed by combining two or more of an alkylene group, an arylene group, a group represented by Formula (1-1), a group represented by Formula (1-3), a group represented by Formula (1-4), or a group represented by Formula (1-7), and, the $R^{111}$ in Formula (A) is a hydrogen atom or an aryl group, the $R^1$ and $R^2$ are a hydrogen atom, the $R^3$ and $R^4$ are represented by Formula (A), where the $L^3$ is a single bond or $—SO_3—$, and the $R^{111}$ is a hydrogen atom, the Q is a group represented by Formula (1-1), the $L^{11}$ is a methylene group, the $R^8$ bonds only at the meta position on the side opposite to the pyrrole ring with respect to the bonding position with $L^{11}$, and is an alkoxy group or a halogen atom, and n is 0 or 1, in the case where n is 0, at least one of the $R^1$ to $R^5$, $L^{11}$, and Q includes a carboxy group or a salt thereof, a sulfo group or a salt thereof, and, in the case where n is 1, at least one of the $R^1$ to $R^5$, $R^8$, $L^{11}$, and Q includes a carboxy group or a salt thereof, a sulfo group or a salt thereof, wherein at least one of the $R^3$ and $R^4$ is a sulfo group or a salt thereof, or, at least one of the $R^1$ to $R^5$ includes two or more of a carboxy group or a salt thereof, a sulfo group or a salt thereof, a phosphono group or a salt thereof, an onio group, or a polyamino acid residue in the case where n is 0, or at least one of the $R^1$ to $R^5$ and $R^8$ includes two or more of a carboxy group or a salt thereof, a sulfo group or a salt thereof, a phosphono group or a salt thereof, an onio group, or a polyamino acid residue in the case where n is 1.

<12> The fluorescent compound according to any one of <1> to <6>, in which the fluorescent compound is represented by Formula (7) or Formula (8).

Formula (7)

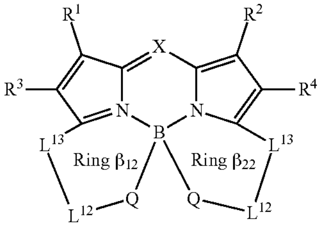

-continued

Formula (8)

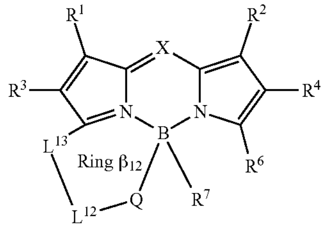

In the formula, X represents $CR^5$ or N.

$R^1$ to $R^7$ and Q respectively have the same meanings as $R^1$ to $R^7$ and $Q^1$ in Formula (1) or (4).

$L^{12}$ represents a single bond or an alkylene group, an alkenylene group, an arylene group, a heteroarylene group, a cycloalkylene group, a divalent aliphatic heterocyclic group, or a group represented by any one of Formulae (1-1) to (1-8), or a linking group formed by combining two of these groups.

$L^{13}$ represents a methylene group or a group represented by any one of Formulae (1-1) to (1-8).

Here, a ring $\beta_{12}$ and a ring $\beta_{22}$ are a 5- to 8-membered ring.

<13> The fluorescent compound according to <12>, wherein the fluorescent compound is represented by Formula (7), wherein the Q is a group represented by Formula (1-1),
the $R^1$ and the $R^2$ are a hydrogen atom,
the $R^3$ and $R^4$ are represented by Formula (A), where the $L^3$ is a single bond or $—SO_3—$, and the $R^{111}$ is a hydrogen atom,
the $L^{12}$ is an alkylene group,
the $L^{13}$ is a methylene group, or a group represented by Formula (1-3),
the ring $\beta_{12}$ and the ring $\beta_{22}$ are a 7-membered ring,
the X is $CR^5$, where $R^5$ is represented by Formula (A), and the $L^3$ and the $R^{11}$ in Formula (A) satisfy the following (a) or (b);
(a) the $L^3$ is a single bond, and, the $R^{111}$ is an aryl group
(b) the $L^3$ is an alkylene group, an arylene group, a group represented by Formula (1-1), a group represented by Formula (1-3), a group represented by Formula (1-4), or a group represented by Formula (1-7), or, a group formed by combining two or more of an alkylene group, an arylene group, a group represented by Formula (1-1), a group represented by Formula (1-3), a group represented by Formula (1-4), or a group represented by Formula (1-7), and, the $R^{111}$ is a hydrogen atom.

<14> The fluorescent compound according to any one of <1> to <6>, in which the fluorescent compound is represented by Formula (9).

Formula (9)

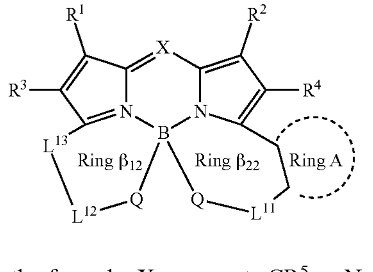

In the formula, X represents $CR^5$ or N.

$R^1$ to $R^5$ and Q respectively have the same meanings as $R^1$ to $R^5$ and $Q^1$ in Formula (1) or (4).

$L^{11}$ and $L^{12}$ represent a single bond or an alkylene group, an alkenylene group, an arylene group, a heteroarylene group, a cycloalkylene group, a divalent aliphatic heterocyclic group, or a group represented by any one of Formulae (1-1) to (1-8), or a linking group formed by combining two of these groups.

$L^{13}$ represents a methylene group or a group represented by any one of Formulae (1-1) to (1-8).

A ring A represents a hydrocarbon ring or a heterocycle.

Here, a ring $\beta_{12}$ is a 5- to 8-membered ring, and a ring $\beta_{21}$ is a 6- to 8-membered ring.

<15> The fluorescent compound according to any one of <1> to <11>, in which at least one of $R^1$ to $R^8$, $L^1$, $L^2$, $L^{11}$ to $L^{13}$, Q, $Q^1$, or $Q^2$ has a moiety bondable to a biological substance.

<16> A fluorescent labeled biological substance, which is obtained through bonding between the fluorescent compound according to <15> and a biological substance.

<17> The fluorescent labeled biological substance according to <16>, in which the biological substance is any one of a protein, a peptide, an amino acid, a nucleic acid, a sugar chain, or a lipid.

<18> The fluorescent labeled biological substance according to <16> or <17>, in which the bonding between the fluorescent compound and the biological substance is formed by any one of the followings i) to v).

i) non-covalent or covalent bond between peptides,
ii) Van der Waals interaction between a long-chain alkyl group in a fluorescent compound and a lipid bilayer or lipid in a biological substance,
iii) an amide bond formed by reacting an N-hydroxysuccinimide ester in a fluorescent compound with an amino group in a biological substance,
iv) a thioether bond formed by reacting a maleimide group in a fluorescent compound with a sulfanyl group in a biological substance, and
v) a bond with a formation of a triazole ring, which is formed by Click reaction between an azido group in a fluorescent compound and an acetylene group in a biological substance, or between an acetylene group in a fluorescent compound and an azido group in a biological substance.

The fluorescent compound according to an aspect of the present invention is a fluorescent compound that realizes both sufficient hydrophilicity and high light resistance required for in vivo fluorescence imaging. In addition, the fluorescent labeled biological substance according to an aspect of the present invention have both excellent hydrophilicity and excellent light resistance and thus can be suitably used for in vivo fluorescence imaging.

DESCRIPTION OF THE PREFERRED EMBODIMENTS

In the present invention, in a case where there are a plurality of substituents or linking groups represented by a specific symbol or formula (hereinafter, referred to as substituents or the like), or in a case where a plurality of substituents or the like are regulated at the same time, the substituents or the like may be the same or different from each other, unless otherwise specified. The same applies to the regulation of the number of substituents or the like. Further, in a case where a plurality of substituents or the like are close to each other (particularly in a case where they are adjacent to each other), they may be linked to each other to form a ring, unless otherwise specified. Further, unless otherwise specified, rings such as an alicyclic ring, an aromatic ring, and a heterocycle may be condensed to form a fused ring.

In the present specification, in a case where E type and Z type of the double bond are present in the molecule, any one of the E type or the Z type, or a mixture thereof may be used unless otherwise specified. In addition, in a case where a compound has a diastereomer and an enantiomer, any one of the diastereomer or the enantiomer may be used, or a mixture thereof may be used unless otherwise specified. For example, among the fluorescent compounds according to the embodiment of the present invention, a compound having a tridentate dipyrromethene skeleton include enantiomers having a boron atom as an asymmetric center.

In the present invention, the representation of a compound (including a complex) or substituent is used to mean not only the compound itself but also a salt thereof, and an ion thereof. For example, in a case where $R^{111}$ in Formula (A) is a dissociative hydrogen atom (preferably a dissociative hydrogen atom in the specific hydrophilic group Pi described later), the hydrogen atom may dissociate to provide a salt structure (preferably, a salt in the specific hydrophilic group Pi).

In a case of a salt structure, the kind of the salt may be one kind, two or more kinds may be mixed, the group having the salt form and the group having the free acid structure may be mixed in the compound, and the compound having the salt structure and the compound having the free acid structure compound may be mixed.

In addition, it is meant to include those in which a part of the structure is changed within a range that does not impair the effects of the present invention. Furthermore, it is meant that a compound, which is not specified to be substituted or unsubstituted, may have any substituent within a range that does not impair the effects of the present invention. The same applies to a substituent (for example, a group represented by "alkyl group", "methyl group", "methyl") and a linking group (for example, a group represented by "alkylene group", "methylene group", "methylene"). Among such substituents, a preferred substituent in the present invention is a substituent selected from a substituent group T described later.

In the present invention, the dipyrromethene boron complex structure means a structure in which a dipyrromethene skeleton is coordinated to a boron atom in any one of a bidentate, tridentate, or tetradentate coordination. The tridentate or tetradentate coordination is formed by coordinating, to the boron atom, one or two substituents on the dipyrromethene skeleton in addition to the two nitrogen atoms of dipyrromethene.

Further, in the chemical structural formulae described in the present invention, the positive charge on one of the two nitrogen atoms of dipyrromethene and the negative charge on the boron atom are omitted.

In addition, in the present invention, the numerical range indicated by using "to" means a range including the numerical values before and after "to" as the lower limit value and the upper limit value, respectively.

Further, in the present invention, $C_o$ means the number of carbon atoms o, and for example, a linear alkyl group having $C_{18}$ or more means a linear alkyl group having 18 or more carbon atoms.

The fluorescent compound according to the embodiment of the present invention is represented by Formula (1) or Formula (4) described later. Although the details of the reason why the fluorescent compound according to the embodiment of the present invention exhibits sufficient hydrophilicity and excellent light resistance required for in vivo fluorescence imaging are not clear, it is speculated as follows.

Any fluorescent compound according to the embodiment of the present invention is a compound having a specific structure in which a compound having a dipyrromethene skeleton into which one or two or more substituents have been introduced is coordinated to a boron atom as a tridentate ligand or a tetradentate ligand instead of a bidentate ligand, and further has a specific hydrophilic group, as shown in each formula. Therefore, it is speculated that the stability of the boron atom in the compound (complex) is improved, photolysis involving the boron atom by reactive oxygen species is inhibited, excellent light resistance is exhibited, and sufficient hydrophilicity is also exhibited.

Hereinafter, the fluorescent compound according to the embodiment of the present invention, which is represented by Formula (1), and the fluorescent compound according to the embodiment of the present invention, which is represented by Formula (4), will be described in detail in order.

<Fluorescent Compound Represented by Formula (1)>

The fluorescent compound according to the embodiment of the present invention, which is represented by Formula (1), is as follows.

Formula (1)

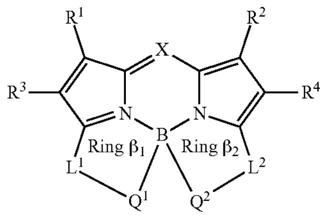

In the formula, X represents $CR^5$ or N.

$R^1$ to $R^5$ represent a halogen atom, a cyano group, or a group represented by Formula (A).

$Q^1$ and $Q^2$ represent a group represented by any one of Formulae (1-1) to (1-3).

$L^1$ and $L^2$ represent an alkylene group, an alkenylene group, an arylene group, a heteroarylene group, a cycloalkylene group, a cycloalkenylene group, a divalent aliphatic heterocyclic group, a group represented by any one of Formulae (1-1) to (1-8), or a linking group formed by combining two to four of these groups.

A ring $\beta_1$ (that is, a ring constituted of $L^1$, $Q^1$, a boron atom, and among the atoms constituting a pyrrole ring, a nitrogen atom and a carbon atom which connects $L^1$ and the nitrogen atom) and a ring $\beta_2$ (that is, a ring constituted of $L^2$, $Q^2$, a boron atom, and among the atoms constituting a pyrrole ring, a nitrogen atom and a carbon atom which connects $L^2$ and the nitrogen atom) are each a 5- to 8-membered ring.

Here, at least one of $R^1$ to $R^5$, $L^1$, $L^2$, $Q^1$, or $Q^2$ has, as a hydrophilic group, at least one of a carboxy group or a salt thereof, a sulfo group or a salt thereof, a phosphono group or a salt thereof, an onio group, or a polyamino acid residue (hereinafter, also referred to as a "specific hydrophilic group Pi").

Further, $Q^1$, $Q^2$, $L^1$, and $L^2$ do not include a group in which two or more groups represented by any one of Formulae (1-1) to (1-3) are consecutive.

In a case where X is $CR^5$, where $R^5$ is a group represented by Formula (A), the ring $\beta_1$ and the ring $\beta_2$ are a 6-membered ring, and $L^1$ and $L^2$ are an arylene group, it is preferable that (a) there is no case in which $L^3$ is a single bond and $R^{111}$ is an aryl group having a linear alkyl group having 18 or more carbon atoms as a substituent. In a case where X is $CR^5$, where $R^5$ is a group represented by Formula (A), the ring $\beta_1$ and the ring $\beta_2$ are a 6-membered ring, and $L^1$ and $L^2$ are an arylene group, it is preferable that (b) there is no case in which $L^3$ is an arylene group and $R^{111}$ is a linear alkyl group having 18 or more carbon atoms. In these fluorescent compounds of the (a) and the (b), $Q^1$ and $Q^2$ that are coordinated to the boron atom are directly linked to the arylene group, and thus the fluorescent compounds of the (a) and the (b) have high acidity, thereby being hydrolyzed in water and hydrolyzed by a substance derived from a living body, and sufficient light resistance cannot be obtained. On the other hand, in the fluorescent compound according to the embodiment of the present invention, which is not the compound of the (a) and the (b), it is speculated that hydrolysis is inhibited since $Q^1$ and $Q^2$ are not directly linked to the arylene group and high light resistance can be maintained in water and in the vicinity of the substance derived from the living body.

In addition, in a case where X is $CR^5$, where $R^5$ is a group represented by Formula (A), it is preferable that (c) there is no case in which L is a single bond and $R^{111}$ is an aryl group having a linear alkyl group having 18 or more carbon atoms as a substituent. Further, in a case where X is $CR^5$, where $R^5$ is a group represented by Formula (A), it is preferable that (d) there is no case in which L is an arylene group and $R^{111}$ is a linear alkyl group having 18 or more carbon atoms. From the viewpoint of stabilizing the coordinate bond with $Q^1$ and $Q^2$ by suppressing the strain generated in the conformation of the boron atom and obtaining more sufficient light resistance, it is preferable that the above (c) and (d) are satisfied in a case where the ring $\beta_1$ and the ring $\beta_2$ are a 6-membered ring, and it is more preferable for the above (c) and (d) be satisfied in a case where the ring $\beta_1$ and the ring $\beta_2$ are a 5-, 6-, or 8-membered ring.

In a case where X is $CR^5$, where $R^5$ is a group represented by Formula (A), the ring $\beta_1$ and the ring $\beta_2$ are a 6-membered ring, $L^1$ and $L^2$ are an arylene group, and $R^{111}$ has a substituent having a dipyrromethene boron complex structure, it is preferable that (e) the dipyrromethene boron complex structure of this $R^{111}$ has a structure in which a dipyrromethene skeleton is coordinately bonded to a boron atom in the tridentate or tetradentate coordination. That is, the dipyrromethene boron complex structure of this $R^{111}$ is preferably a structure having a tridentate skeleton or a tetradentate skeleton with respect to a boron atom and more preferably have a tridentate coordinate skeleton represented by Formula (4) described later or a tetradentate skeleton represented by Formula (1). Since a fluorescent compound that does not satisfy the (e), that is, a fluorescent compound having a dipyrromethene skeleton in which the dipyrromethene boron complex structure of $R^{111}$ has a bidentate skeleton, has a bidentate skeleton, photolysis involving the boron atom caused by reactive oxygen species easily occurs, and sufficient light resistance cannot be obtained. On the other hand, it is speculated that in the fluorescent compound according to the embodiment of the present invention, satisfying the (e), the dipyrromethene skeleton is coordinately bonded by the tridentate or tetradentate coordination, whereby photolysis is inhibited and high light resistance is maintained.

Further, in a case where X is $CR^5$, where $R^5$ is a group represented by Formula (A), and $R^{111}$ has a substituent having a dipyrromethene boron complex structure, it is preferable that (f) the dipyrromethene boron complex structure has a structure in which a dipyrromethene skeleton is coordinately bonded to a boron atom in the tridentate or tetradentate coordination. That is, this dipyrromethene boron complex structure is preferably a structure having a tridentate skeleton or a tetradentate skeleton with respect to a boron atom and more preferably has a tridentate coordinate skeleton represented by Formula (4) described later or a tetradentate skeleton represented by Formula (1). It is speculated that in the fluorescent compound satisfying the (e), the dipyrromethene skeleton of the dipyrromethene boron complex structure of $R^{111}$ is coordinately bonded by the tridentate or tetradentate coordination, whereby photolysis due to the bidentate coordination is inhibited and sufficient light resistance is obtained. It is noted that this effect is more prominent in a case where the light resistance decreases due to the strain generated in the conformation of the boron atom. From this point, it is preferable that another configuration of the above (f) satisfies the (f) in a case where the ring $\beta_1$ and the ring $\beta_2$ are a 6-membered ring, and more preferable to satisfy the (f) in a case where the ring $\beta_1$ and the ring $\beta_2$ are a 5-, 6-, or 8-membered ring.

Hereinafter, the substituent and the like in Formula (1) will be described in detail.

Group Represented by Formula (A)

$$*\text{-}L^3\text{-}R^{111} \quad \text{Formula (A)}$$

In the formula, $L^3$ represents a single bond or a linking group formed by combining one or two or more of an alkylene group, an arylene group, and a group represented by any one of Formulae (1-1) to (1-8).

However, $L^3$ does not include a group in which two or more groups represented by any one of Formulae (1-1) to (1-3) are consecutive.

$R^{111}$ represents a hydrogen atom, an alkyl group, an alkenyl group, an alkynyl group, an aryl group, a heteroaryl group, or a monovalent aliphatic heterocyclic group.

In a case where the hydrogen atom that can be adopted as $R^{111}$ is a dissociative hydrogen atom in the specific hydrophilic group Pi, which is described later, the hydrogen atom may dissociate to form a salt structure in the specific hydrophilic group Pi, which is described later. This salt has the same meaning as the salt which is described later in "Specific hydrophilic group Pi".

In addition, the number of combinations of the alkylene group, the arylene group, and the group represented by any one of Formulae (1-1) to (1-8) is one or two or more, and the number of combinations is not particularly limited.

However, regarding the groups represented by Formula (A), in a case where the group closest to * is an alkylene group or an arylene group (hereinafter, referred to as a "*-alkylene group or *-arylene group"), and the following (i) or (ii) is satisfied, it should be understood that $L^3$ is a single bond and $R^{111}$ is an alkyl group or an aryl group.

(i) The *-alkylene group or *-arylene group is an unsubstituted group.

(ii) The group represented by Formula (A) is a group having a specific hydrophilic group Pi, and all the specific hydrophilic group Pi's included in the group represented by Formula (A) are directly bonded to the *-alkylene group or *-arylene group.

Regarding a group represented by Formula (A), having a*-alkylene group or *-arlylene group other than the one described above, it should be understood that $L^3$ is not a single bond.

* represents a bonding portion.

The alkylene group that can be adopted as $L^3$ has the same meaning as the group in which one hydrogen atom is further removed from the alkyl group selected from the substituent group T, which is described later, and the same applies to the preferred one.

The arylene group that can be adopted as $L^3$ has the same meaning as the group in which one hydrogen atom is further removed from the aryl group selected from the substituent group T, which is described later, and the same applies to the preferred one.

The alkylene group and arylene group that can be adopted as $L^3$ may be an unsubstituted group or a group having a substituent. The substituent that the alkylene group and arylene group that can be adopted as $L^3$ may have is not particularly limited and is preferably selected from the substituent group T, which is described later, and the number of substituents is not particularly limited as long as it is one or more, and for example, can be four or less.

The substituent that the alkylene group and arylene group that can be adopted as $L^3$ may have is more preferably an alkoxy group and a specific hydrophilic group Pi.

The linking group that can be adopted as $L^3$, formed by combining one or two or more of an alkylene group, an arylene group, and a group represented by any one of Formulae (1-1) to (1-8), is preferably a linking group formed by combining one to six of an alkylene group, an arylene group, and a group represented by any one of Formulae (1-1) to (1-8), and more preferably a linking group formed by combining three to six of an alkylene group, an arylene group, and a group represented by any one of Formulae (1-1) to (1-8), and more preferably a linking group formed by combining three to six of an alkylene group, an arylene group, and a group represented by any one of Formulae (1-1), (1-3), (1-4) and (1-7), more preferably a linking group formed by combining five or six of an alkylene group, an arylene group, and a group represented by any one of Formulae (1-1), (1-3), (1-4) and (1-7).

In the linking group that can be adopted as $L^3$, formed by combining one or two or more of an alkylene group, an arylene group, and a group represented by any one of Formulae (1-1) to (1-8), the number of groups to be combined is not particularly limited, and preferably 2 to 20,000 on average.

The alkyl group, alkenyl group, alkynyl group, aryl group, heteroaryl group, and monovalent aliphatic heterocyclic group that can be adopted as $R^{111}$ have the same meanings as the corresponding groups in the substituent group T, and the same applies to the preferred ones.

In addition, all the alkyl group, alkenyl group, alkynyl group, aryl group, heteroaryl group, and monovalent aliphatic heterocyclic group that can be adopted as $R^{111}$ may be an unsubstituted group or a group having a substituent. The substituent that each of the above groups that may be adopted as $R^{111}$ may have is not particularly limited, is preferably a group selected from the substituent group T, which is described later and is more preferably an alkyl group, an alkoxy group, an aryl group, and a specific hydrophilic group Pi. In this case, the number of substituents is not particularly limited as long as the substituents of the corresponding number can be adopted as the structure, and the number of substituents is preferably, for example, 1 to 5. Further, the number of the specific hydrophilic group Pi's is not particularly limited as long as the specific hydrophilic group Pi's of the corresponding number can be adopted as the structure. Specifically, in a case of an alkyl group, an alkenyl group, an alkynyl group, an aryl group, a heteroaryl group, and a monovalent aliphatic heterocyclic group, all of which can adopt a plurality of specific hydrophilic group Pi's, the number of the specific hydrophilic group Pi's is, for example, preferably 1 to 5, more preferably 1 to 4, and still more preferably 1 or 2. Further, the substituent (where the specific hydrophilic group Pi is excluded) that each of the above groups that may be adopted as $R^{111}$ may have, preferably have a substituent, and examples thereof include a group selected from the substituent group T, which is described later, and preferably an alkyl group and an alkoxy group.

In the configuration in which the monovalent aliphatic heterocyclic group has the specific hydrophilic group Pi, for example, a configuration (for example, a piperazinium group) in which the nitrogen atom, which is a ring-constituting atom of the aliphatic heterocycle, is incorporated as an ammonio group is also included, in addition to the configuration in which the specific hydrophilic group Pi is adopted as the substituent.

More specifically, the following groups are preferably mentioned as the $R^{111}$.

(1) In a case where $L^3$ is a single bond and does not have a specific hydrophilic group Pi as Formula (A)

$R^{111}$ is preferably a hydrogen atom, or an alkyl group, an alkenyl group, an alkynyl group, an aryl group, or a heteroaryl group, which does not have a specific hydrophilic group Pi, and is more preferably an aryl group.

(2) In a case where $L^3$ is a single bond and has a specific hydrophilic group Pi as Formula (A)

$R^{111}$ is preferably an alkyl group, an alkenyl group, an alkynyl group, an aryl group, or a monovalent aliphatic heterocyclic group, which has a specific hydrophilic group Pi, and is more preferably an aryl group.

(3) In a case where $L^3$ is a group formed by combining one or two or more of an alkylene group, an arylene group, and a group represented by any one of Formulae (1-1) to (1-8).

$R^{111}$ is preferably a hydrogen atom, or an alkyl group, an alkenyl group, an alkynyl group, an aryl group, or a monovalent aliphatic heterocyclic group, which has a specific hydrophilic group Pi, and is more preferably a hydrogen atom, or an alkyl group having a specific hydrophilic group Pi.

Among them, it is more preferable that X is $CR^5$, where $R^5$ is a group represented by Formula (A), and the above-described preferred configurations of the (1) to (3) are satisfied, from the viewpoint that the high light resistance can be imparted due to the inhibition of photochemical degradation. The reason for this is presumably due to a mechanism similar to the mechanism in which the photochemical degradation of the boron complex having a bidentate dipyrromethene ligands easily occurs in a case where the meso position is N as compared with a case where the meso position is CH, as described in The Journal of Physical Chemistry A, 2016, 120, p. 2537-2546.

Group Represented by Formula (1-1) to Formula (1-8)

Formula (1-1)

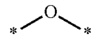

-continued

Formula (1-2)

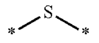

Formula (1-3)

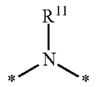

Formula (1-4)

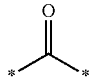

Formula (1-5)

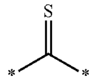

Formula (1-6)

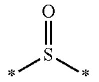

Formula (1-7)

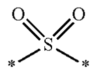

Formula (1-8)

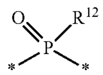

in the formulae, $R^{11}$ and $R^{12}$ each independently represent a hydrogen atom or a substituent.

* represents a bonding portion.

The substituent that can be adopted as $R^{11}$ is not particularly limited and is preferably selected from the substituent group T, which is described later. $R^{11}$ is preferably a hydrogen atom, an alkyl group, an aryl group, a heteroaryl group, an acyl group, or a sulfonyl (a sulfonyl group substituted with alkyl, cycloalkyl, or aryl, and preferably alkylsulfonyl) and more preferably a hydrogen atom or an alkyl group.

All the alkyl group, aryl group, heteroaryl group, acyl group, and sulfonyl group that can be adopted as $R^{11}$ may have no substituent or may have a substituent. As the above group having a substituent, an alkyl group, an aryl group, a heteroaryl group, an acyl group, and a sulfonyl group, which have a specific hydrophilic group Pi as a substituent, can be preferably mentioned.

The substituent that can be adopted as $R^{12}$ is not particularly limited and is preferably selected from the substituent group T, which is described later. $R^{12}$ is preferably a hydrogen atom, a hydroxy group, an alkoxy group, an aryloxy group, an alkyl group, an aryl group, or a heteroaryl group, more preferably a hydroxy group, an alkoxy group, or an aryloxy group, and still more preferably a hydroxy group.

In a case where $R^{12}$ is a dissociative hydrogen atom in the specific hydrophilic group Pi, which is described later, the hydrogen atom may dissociate to form a salt form in the specific hydrophilic group Pi, which is described later. This salt has the same meaning as the salt which is described later in "Specific hydrophilic group Pi".

As the group formed by combining groups represented by Formulae (1-1) to (1-8), groups represented by Formulae (1A-1) to (1A-9) are preferably mentioned.

Formula (1A-1)

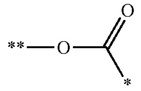

-continued

Formula (1A-2)

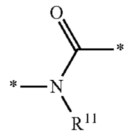

Formula (1A-3)

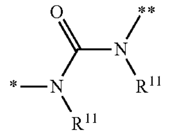

Formula (1A-4)

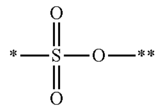

Formula (1A-5)

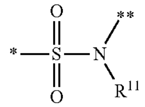

Formula (1A-6)

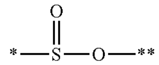

Formula (1A-7)

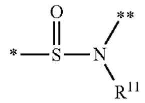

Formula (1A-8)

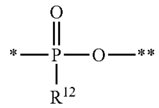

Formula (1A-9)

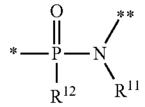

$R^{11}$ and $R^{12}$ respectively have the same meanings as the above $R^{11}$ and $R^{12}$.

* and  represents a bonding portion. In addition,  represents a bonding portion with $R^{111}$ in a case where the group is a group that can be adopted as L. Formula (1A-2) may be bonded with $R^{111}$ on any * side in $L^3$.

As the linking group formed by combining groups represented by Formulae (1-1) to (1-8), which can be adopted as $L^1$ and $L^2$, a group represented by Formulae (1A-2) is preferred. In addition, a bond may be formed on any * side as long as the bonding is possible.

As the linking group formed by combining groups represented by Formulae (1-1) to (1-8), which can be adopted as $L^3$, a group represented by Formulae (1A-1), (1A-2), (1A-4), or (1A-8) is preferred, and a group represented by Formulae (1A-1), (1A-2), or (1A-4) is more preferred.

The groups represented by Formula (1A-1), (1A-4), and (1A-8) together with the group represented by $R^{111}$ as a hydrogen atom respectively corresponds to a carboxy group, a sulfo group, or phosphono group, as the specific hydrophilic group Pi. In addition, the groups formed by dissociating hydrogen atoms from these groups as the dissociative hydrogen atom respectively correspond to a salt of the carboxy group, a salt of the sulfo group, or a salt of the phosphono group.

$L^1$ to $L^3$ may be a group represented by any one of Formulae (1-1) to (1-8) or a linking group formed by combining a linking group formed by combining these groups with an alkylene group and the like. In addition, $L^1$ to $L^3$ may be a group represented by any one of Formulae (1-1) to (1-8), linked via one or two or more alkylene groups, or a linking group formed by linking two or three or more linking groups formed by combining groups represented by Formulae (1-1) to (1-8). However, each of the combinations for $L^1$ and $L^2$ is a combination within a range satisfying the number of ring members of the ring $\beta_1$ and the ring $\beta_2$.

Examples of the linking group formed by combining two or more groups, which can be adopted as $L^3$, preferably include: a group represented by alkylene group—[group represented Formula (1A-2)-alkylene group]—group represented Formula (1A-1), (1A-4), or (1A-8); a group represented by arylene group—[group represented Formula (1A-2)—alkylene group]—group represented by Formula (1A-1), (1A-4), or (1A-8); arylene group—group represented by Formula (1A-1), arylene group—group represented by Formula (1A-2)-alkylene group—group represented by Formula (1A-1), arylene group—group represented by Formula (1A-2)—alkylene group (—group represented by Formula (1A-4))—group represented by Formula (1A-1), a group represented by arylene group—group represented Formula (1A-2)—[alkylene group—group represented by Formula (1-1)]—alkylene group—group represented by Formula (1A-1), (1A-4), or (A-8); and a group represented by alkylene group—group represented Formula (1A-2)—[alkylene group—group represented by Formula (1-1)]-alkylene group—group represented by Formula (1A-1), (1A-4), or (A-8), and more preferably include: arylene group—group represented by Formula (1A-1), arylene group—group represented by Formula (1A-2)—alkylene group—group represented by Formula (1A-1), arylene group—group represented by Formula (1A-2)—alkylene group (—group represented by Formula (1A-4))—group represented by Formula (1A-1), arylene group—group represented by Formula (1A-2)—[alkylene group—group represented by Formula (1-1)]—alkylene group—group represented by Formula (1A-1). It is noted that [ ] indicates a repeating structure.

The linking groups that can be used as $L^1$ and $L^2$ are as described later.

X

The X represents $CR^5$ or N, and $CR^5$ is preferred.

$R^1$ to $R^5$

The $R^1$ to $R^5$ each independently represent a halogen atom, a cyano group, or a group represented by Formula (A).

As the halogen atom that $R^1$ to $R^5$ can adopt, a fluorine atom, a chlorine atom, a bromine atom, and an iodine atom are mentioned, and a fluorine atom is preferred.

The $R^1$ to $R^4$ is preferably a group represented by Formula (A) and more preferably any one of the groups of the preferred aspects (1) to (3) of the $R^{111}$. In a case where the $R^1$ to $R^4$ have a specific hydrophilic group Pi, the $R^1$ to $R^4$ is preferably the group having a specific hydrophilic group Pi, described in the preferred aspect (2) or (3) of the $R^{111}$.

The $R^5$ is preferably a hydrogen atom, an alkyl group, an alkenyl group, an alkynyl group, an aryl group, or a heteroaryl group. Here, preferred substituents as $R^5$ respectively have the same meanings as the alkyl group, alkenyl group, alkynyl group, aryl group, and heteroaryl group in $R^{111}$ of Formula (A). The $R^5$ is more preferably an alkyl group, an alkenyl group, an alkynyl group, an aryl group, or a heteroaryl group, and is more preferably an aryl group. The alkyl group, alkenyl group, alkynyl group, aryl group, and heteroaryl group, all of which can be preferably adopted as $R^5$ are preferably groups having a specific hydrophilic group Pi.

$Q^1$ and $Q^2$

The $Q^1$ and $Q^2$ each independently represent a group represented by any one of Formulae (1-1) to (1-3), $Q^1$ and $Q^2$ may be the same or different from each other and are preferably the same.

More specifically, one of $Q^1$ and $Q^2$ is preferably a group represented by Formula (1-1) and more preferably both $Q^1$ and $Q^2$ are a group represented by Formula (1-1), from the viewpoint of having the highest bond energy with the boron atom and being stable. The fact that the group represented by Formula (1-1), that is, the oxygen atom, has the highest bonding energy with the boron atom and is stable as compared with other atoms can be referred to, for example, Dean, John, A. Lange's Handbook of Chemistry. McGraw-Hill., PROPERTIES OF ATOMS, RADICALS, AND, BONDS, SECTION 4.41.

$L^1$ and $L^2$

The $L^1$ and $L^2$ each independently represent an alkylene group, an alkenylene group, an arylene group, a heteroarylene group, a cycloalkylene group, a cycloalkenylene group, a divalent aliphatic heterocyclic group, a group represented by any one of Formulae (1-1) to (1-8), or a linking group formed by combining two to four of these groups. The $L^1$ and $L^2$ each independently preferably represent an alkylene group, an alkenylene group, an arylene group, a group represented by any one of Formulae (1-1) to (1-8), or a linking group formed by combining two of these groups. The $L^1$ and $L^2$ each independently more preferably represent a linking group formed by combining an alkylene group and an arylene group.

The alkylene group, the alkenylene group, the arylene group, the heteroarylene group, the cycloalkylene group, the cycloalkenylene group, and the divalent aliphatic heterocyclic group, all of which can be adopted as $L^1$ and $L^2$, respectively have the same meanings as groups obtained by further removing one hydrogen atom from an alkyl group, an alkenyl group, an aryl group, a heteroaryl group, a cycloalkyl group, a cycloalkenyl group, and an aliphatic heterocyclic group, which are selected from the substituent group T described later, and the same applies to the preferred ones.

Further, each of the above groups that can be adopted as $L^1$ and $L^2$ may be an unsubstituted group or a group having a substituent. The substituent that each of the above groups that may be adopted as $L^1$ and $L^2$ may have is not particularly limited and is preferably selected from the substituent group T, which is described later, and the number of substituents is not particularly limited as long as it is one or more, and for example, can be four or less.

The substituent that each of the above groups that may be adopted as $L^1$ and $L^2$ may have is more preferably a halogen atom, a cyano group, an alkoxy group, an oxygen atom, a group containing one or more carboxy groups, a group containing one or more sulfo groups, a group containing one or more phosphono groups, a group containing one or more onio groups, or a group containing a polyamino acid residue, and still more preferably a halogen atom, an alkoxy group, a carboxy group, a phosphono group, a sulfo group, an onio group, a polyamino acid residue, or an amino group having a polyamino acid residue as a substituent, and particularly more preferably a halogen atom or an alkoxy group. The above-described carboxy group, sulfo group, and phosphono group each include a salt thereof.

In the arylene group, heteroarylene group, cycloalkylene group, cycloalkenylene group, and divalent aliphatic heterocyclic group, which can be adopted as $L^1$, the relationship between the bonding portion that bonds to the carbon atom in the pyrrole ring in Formula (1) and the bonding portion that bonds to the $Q^1$ is not particularly limited, but it is preferably a relationship in which two atoms (vicinal atoms) are adjacent to each other in each group. In addition, in the arylene group, heteroarylene group, cycloalkylene group, cycloalkenylene group, and divalent aliphatic heterocyclic group, which can be adopted as $L^2$, the relationship between the bonding portion that bonds to the carbon atom in the pyrrole ring in Formula (1) and the bonding portion that bonds to the $Q^2$ is not particularly limited, but it is preferably a relationship in which two atoms (vicinal atoms) are adjacent to each other in each group.

For example, in a case where a phenylene group is contained in $L^1$ and $L^2$, a 1,2-phenylene group is preferable.

The position of the carbon-carbon double bond (C═C bond) in the alkenylene group and cycloalkenylene group that can be adopted as $L^1$ is not particularly limited. In addition, the position of the carbon-carbon double bond (C═C bond) in the alkenylene group and cycloalkenylene group that can be adopted as $L^2$ is also not particularly limited.

The number of carbon atoms of the alkylene group that can constitute $L^1$ and $L^2$ is not the total number of carbon atoms that constitutes the alkylene group, but means the number of carbon atoms incorporated in the ring structure (that is, the ring $\beta_1$ (or ring $\beta_2$)) constituted of the carbon atom and the nitrogen atom adjacent to each other in the pyrrole ring, the boron atom, and $Q^1$ and $L^1$ (or $Q^2$ and $L^2$) in Formula (1). In the present invention, it is also referred to as "the number of carbon atoms forming a ring structure together with $Q^1$ (or $Q^2$)". For example, in a case of a 1-carboxy-2,3-propylidene group, the carbon atom at the 1-position at which the carboxy group introduced is not a carbon atom forming a ring structure together with $Q^1$ (or $Q^2$), and thus the number of carbon atoms forming a ring structure together with $Q^1$ (or $Q^2$) is 2. The alkylene group that can constitute $L^1$ and $L^2$ has preferably 1 to 3 carbon atoms, more preferably 1 or 2 carbon atoms, and still more preferably 1 carbon atoms. On the other hand, the total number of carbons of $L^1$ and $L^2$ is preferably 1 to 46, more preferably 1 to 13, still more preferably 1 to 7, and particularly preferably 1 to 3.

The number of carbon atoms of the alkenylene group that can constitute $L^1$ and $L^2$ and the total number of carbons of the alkenylene group are respectively the same as the number of carbon atoms of the alkylene group that can constitute $L^1$ and $L^2$ and the total number of carbons of the alkylene group. The alkenylene group that can constitute $L^1$ and $L^2$ has preferably 2 or 3 carbon atoms and more preferably 2 carbon atoms. On the other hand, the total number of carbons of $L^1$ and $L^2$ is preferably 2 to 46, more preferably 2 to 13, still more preferably 2 to 7, and particularly preferably 2 or 3.

The number of carbon atoms of the alkylene group that can constitute L described above and alkylene group that can constitute $L^{11}$ and $L^{12}$ described later and the total number of carbons of the alkylene group and alkylene group are respectively counted in the same manner as in the number of carbon atoms of the alkylene group that can constitute $L^1$ and $L^2$ and the total number of carbons of the alkylene group. In addition, the number of carbons of groups, other than these groups, that can constitute $L^1$ to $L^3$, $L^{11}$, and $L^{12}$ (that is, an arylene group, a heteroarylene group, a cycloalkylene group, a cycloalkenylene group, and a divalent aliphatic heterocyclic group) means the total number of carbons.

$L^1$ and $L^2$ may be the same or different from each other and are preferably the same.

$L^1$ and $L^2$ not containing a group represented by any one of Formulae (1-1) to (1-8) are preferably an alkylene group, an alkenylene group (preferably an ethenylene group, and this ethenylene group may have a substituent. The same applies hereinafter.), an arylene group, a heteroarylene group, a cycloalkylene group, a cycloalkenylene group, or a divalent aliphatic heterocyclic group, or a linking group formed by combining two of these groups, more preferably an alkylene group, an alkenylene group (preferably an ethenylene group), an arylene group, a heteroarylene group, a cycloalkylene group or a divalent aliphatic heterocyclic group, or a linking group formed by combining two of these groups, and still more preferably an alkylene group, an alkenylene group (preferably an ethenylene group), an arylene group, or a heteroarylene group, or a linking group formed by combining two of these groups, and particularly more preferably a linking group formed by combining an alkenylene group and an arylene group.

$L^1$ and $L^2$ containing a group represented by any one of Formulae (1-1) to (1-8) are preferably a linking group formed by combining two to four groups among any one of [an alkylene group, an alkenylene group (preferably an ethenylene group), an arylene group, a heteroarylene group, a cycloalkylene group, and a divalent aliphatic heterocyclic group] and [a group represented by any one of Formulae (1-1) to (1-8) described above], and more preferably a linking group formed by combining two to four groups among any one of [an alkylene group, an alkenylene group (preferably an ethenylene group), an arylene group, a heteroarylene group, a cycloalkylene group, and a divalent aliphatic heterocyclic group] and [a group represented by any one of Formulae (1-1), (1-2), (1-3), (1-4), or (1A-2) described above].

Specific hydrophilic group Pi: carboxy group or salt thereof, sulfo group or salt thereof, phosphono group or salt thereof, onio group, and polyamino acid residue.

At least one of $R^1$ to $R^5$, $L^1$, $L^2$, $Q^1$, or $Q^2$ has at least one of a carboxy group or a salt thereof, a sulfo group ($—SO_3H$) or a salt thereof, a phosphono group [$—PO(OH)_2$] or a salt thereof, an onio group, or a polyamino acid residue. The "salt" is meant to include a configuration in which a salt is formed in the molecule of the fluorescent compound represented by Formula (1).

Examples of the salt of carboxy group, sulfo group, and phosphono group include salts of alkali metals such as Na, Li, and K, salts of alkaline earth metals such as Mg, Ca, and Ba, and salts of organic amines such as tetraalkylammonium.

The number of the specific hydrophilic group Pi in the compound represented by Formula (1) is not particularly limited as long as any one of $R^1$ to $R^5$, $L^1$, $L^2$, $Q^1$ or $Q^2$ is included. The number of the specific hydrophilic group Pi that can be possessed as the compound represented by Formula (1) is preferably 1 to 6, more preferably 1 to 4, still more preferably 1 to 3, and particularly preferably 2 or 3, from the viewpoint of compatibility of hydrophilicity and light resistance.

In a case where the fluorescent compound represented by Formula (1) contains a plurality of carboxy groups or the like, the plurality of groups may have any one of a salt structure or a free acid structure and may be the same or different from each other.

Here, the "polyamino acid" means a compound in which two or more amino acids are linked by a peptide bond and has a concept including a peptide and a protein. The number of amino acids constituting the "polyamino acid" is preferably 2 to 30, more preferably 4 to 20, and still more preferably 6 to 10. The "polyamino acid residue" is a group derived from the polyamino acid. The "polyamino acid residue" is preferably a group in which one of the hydrogen atoms of —$NH_2$, —$CO_2H$, —OH, and —SH contained in the amino acids constituting the polyamino acid is replaced with a bond (—) (for example, in a case where the hydrogen atom of —$CO_2H$ is replaced with a bond, —$CO_2H$ becomes —C(═O)—O—.  is a bonding portion served for the polyamino acid to be incorporated into the fluorescent compound of formula (1)). Further, the group in which one of the hydrogen atoms of —$NH_2$, —$CO_2H$, —OH, and —SH contained in the amino acids constituting the polyamino acid is replaced with a bond (—) may be incorporated as a polyamino acid residue via a bond such as >C═O and >NH.

Examples of the onio group include an ammonio group (including a cyclic ammonio such as a pyridinium salt, a piperidinium salt, a piperazinium salt, and a pyrrolidinium salt), a sulfonio group, and a phosphonio group, and an ammonio group is preferred.

Examples of the counter ion constituting the onio group include inorganic ions such as a sulfonate ion and an iodide ion.

In particular, in a case of introducing an electron-withdrawing group such as the above-described sulfo group into at least one of $R^3$ or $R^4$, which has a rich Highest Occupied Molecular Orbital (HOMO), an effect of deepening the oxidation potential of the whole molecule can be obtained, and as a result, it is speculated that high light resistance is imparted as a synergistic effect in addition to water solubility (sufficient hydrophilicity).

From the above viewpoint, at least one of $R^3$ or $R^4$ is preferably a group containing one or more carboxy groups or salts thereof, a group containing one or more sulfo groups or salts thereof, a group containing one or more phosphono groups or salts thereof, a group containing one or more onio groups, or a group containing a polyamino acid residue, more preferably a carboxy group or a salt thereof, a sulfo group or a salt thereof, or a phosphono group or a salt thereof, and still more preferably a sulfo group or a salt thereof.

Other Regulations

The ring $\beta_1$ and the ring $\beta_2$ are each a 5- to 8-membered ring, preferably a 6- to 8-membered ring, more preferably a 6- or 7-membered ring, and still more preferably a 7-membered ring.

Here, the ring $\beta_1$ and the ring $\beta_2$ may be the same or different from each other and are preferably the same.

In the ring structure of the ring $\beta_1$ and the ring $\beta_2$, the combination of $L^1$ and $Q^1$, the combination of $L^2$ and $Q^2$, and the like are not particularly limited, and a combination of the preferred groups that can be respectively adopted as $L^1$, $L^2$, $Q^1$, and $Q^2$, or a combination of the linking groups is preferably mentioned. For example, it is preferable that $L^1$ and $L^2$ are an alkylene group, an ethenylene group, an arylene group, or a heteroarylene group, or a linking group formed by combining two of these groups, and the ring $\beta_1$ and the ring $\beta_2$ are a 6- to 8-membered ring.

The fluorescent compound according to the embodiment of the present invention may have a substituent having a dipyrromethene boron complex structure as a substituent, other than the dipyrromethene boron complex structure represented by Formula (1). In a case of having two or more dipyrromethene boron complex structures in the same molecule, all the dipyrromethene boron complex structures have a tridentate skeleton or a tetradentate skeleton with respect to the boron atom. As a result, high light resistance can be exhibited.

Further, at least one of $R^3$ or $R^4$ has a specific hydrophilic group Pi, and X is $CR^5$. From the viewpoint of improving the light resistance of the fluorescent labeled biological substance according to the embodiment of the present invention, obtained by bonding to with a biological substance at $R^5$, in the fluorescent compound according to the embodiment of the present invention, it is preferable that at least one of $L^1$ or $L^2$ is a linking group containing an unsubstituted or a one substituted arylene group and $R^5$ is an aryl group having a substituent at at least one of the ortho positions with respect to the bonding position to the dipyrromethene skeleton. It is speculated that in a case where the fluorescent compound according to the embodiment of the present invention is a compound having the above-described chemical structure, the decomposition reaction due to the biological substance is inhibited.

Further, it is preferable that $R^5$ has a substituent at both of the ortho positions with respect to the bonding position to the dipyrromethene skeleton, and it is more preferable for these substituents to be an alkyl group or an alkoxy group.

In a case where X is $CR^5$, where $R^5$ is a group represented by Formula (A), $L^3$ is a single bond, and $R^{111}$ is an aryl group, it is preferable that $R^{111}$ is not an aryl group having a linear alkyl group having 18 or more carbon atoms as a substituent, from the viewpoint of obtaining more sufficient water solubility (hydrophilicity). In a case where X is $CR^5$, where $R^5$ is a group represented by Formula (A), $L^3$ is a single bond, and $R^1$ is an aryl group, it is preferable that $R^{111}$ is not an aryl group having a linear alkyl group having 10 or more carbon atoms as a substituent and more preferably not an aryl group having a linear alkyl group having 7 or more carbon atoms as a substituent.

Further, in a case where X is $CR^5$, where $R^5$ is a group represented by Formula (A), $L^3$ is a single bond, and $R^{111}$ is an aryl group, it is preferable that $R^{111}$ is not an aryl group substituted with a substituent containing a boron atom.

As another aspect, in a case where X is $CR^5$, where $R^5$ is a group represented by Formula (A), $L^3$ is a single bond, and $R^{111}$ is an aryl group, it is preferable that $R^{111}$ is an aryl group not substituted with a substituent containing an aryl group or a heteroaryl group.

In addition, in a case where X is $CR^5$, where R is a group represented by Formula (A), $L^3$ is an arylene group, and $R^{111}$ is an alkyl group, it is preferable that $R^{111}$ is not a linear alkyl group having 18 or more carbon atoms, from the viewpoint of obtaining more sufficient water solubility (hydrophilicity). In a case where X is $CR^5$, where $R^5$ is a group represented by Formula (A), $L^3$ is an arylene group, and $R^{111}$ is an alkyl group, it is preferable that $R^{111}$ is not a linear alkyl group having 10 or more carbon atoms and more preferably not a linear alkyl group having 7 or more carbon atoms.

<Fluorescent Compound Represented by Formula (2)>

The fluorescent compound according to the embodiment of the present invention, which is represented by Formula (1), is preferably represented by Formula (2).

Formula (2)

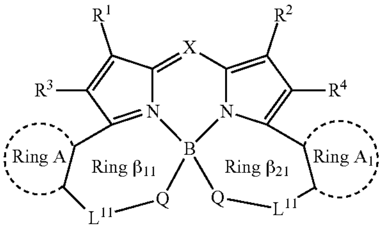

In the formula, X represents $CR^5$ or N and has the same meaning as X in Formula (1).

$R^1$ to $R^5$ and Q respectively have the same meanings as $R^1$ to $R^5$ and $Q^1$ in Formula (1).

A ring A represents a hydrocarbon ring or a heterocycle.

$L^{11}$ represents a single bond or an alkylene group, an ethenylene group, an arylene group, a heteroarylene group, a cycloalkylene group, a divalent aliphatic heterocyclic group, or a group represented by any one of Formulae (1-1) to (1-8), or a linking group formed by combining two of these groups.

However, the ring $\beta_{11}$ and the ring $\beta_{21}$ (that is, two rings constituted of $L^{11}$, Q, the atom bonded to the pyrrole ring and the atom bonded to $L^{11}$ among the atoms constituting the ring A, the boron atom, and the carbon atom bonding the ring A with the nitrogen atom and the nitrogen atom among the atoms constituting the pyrrole ring) are each independently a 6- to 8-membered ring, more preferably a 6- or 7-membered ring, and still more preferably a 7-membered ring. The ring $\beta_{11}$ and the ring $\beta_{21}$ may be the same or different from each other and are preferably the same.

The alkylene group, the arylene group, the heteroarylene group, the cycloalkylene group, and the divalent aliphatic heterocyclic group, all of which can be adopted as $L^{11}$, respectively have the same meanings as groups obtained by further removing one hydrogen atom from an alkyl group, an aryl group, a heteroaryl group, a cycloalkyl group, and an aliphatic heterocyclic group, which are selected from the substituent group T described later, and the same applies to the preferred ones.

Further, each of the above groups that can be adopted as $L^{11}$ may be an unsubstituted group or a group having a substituent. The substituent that each of the above groups that may be adopted as $L^{11}$ may have is not particularly limited and has the same meaning as the substituent for $L^1$ and $L^2$ described above. A group containing one or more carboxy groups, a group containing one or more sulfo groups, a group containing one or more phosphono groups, a group containing one or more onio groups, or a polyamino acid residue is preferred and a carboxy group, a phosphono group, a sulfo group, an onio group, or a polyamino acid residue are more preferred. The above-described carboxy group, sulfo group, and phosphono group each include a salt thereof.

The ethenylene group that can be adopted as $L^{11}$ has the same meaning as the ethenylene group for $L^1$ described above.

$L^{11}$ is preferably an alkylene group and more preferably a methylene group. This methylene group may have a substituent.

The two $L^{11}$'s in the formula may be the same or different from each other.

The ring A is incorporated as a divalent group in the fluorescent compound represented by Formula (2).

As the hydrocarbon ring and heterocycle that can be adopted as the ring A, an aromatic hydrocarbon ring, an aliphatic hydrocarbon ring, an aromatic heterocycle, and an aliphatic heterocycle are mentioned. The ring in the aliphatic hydrocarbon ring and the aliphatic heterocycle may have an unsaturated bond. These rings respectively have the same meanings as rings obtained by substituting, with a hydrogen atom, the bond portion in an aryl group, a cycloalkyl group and cycloalkenyl group, and a heteroaryl group and heterocycle group, which are selected from the substituent group T described later, and the same applies to the preferred ones.

In a case where the ring A is a heterocycle, the atoms constituting the ring $\beta_{11}$ or the ring $\beta_{21}$ are not particularly limited, and examples thereof include a carbon atom, a nitrogen atom, an oxygen atom, and a sulfur atom, and atoms constituting at least one of the ring are preferably carbon atoms.

Specifically, as the aromatic hydrocarbon ring, benzene, naphthalene, and the like are mentioned; as the aliphatic hydrocarbon ring, cyclopropane, cyclopentane, cyclohexane, cyclopropene, cyclopentene, cyclohexene, and the like are mentioned; as the aromatic heterocycle, furan, thiophene, pyrrole, oxazole, thiazole, imidazole, isoxazole, isothiazole, pyrazole, pyridine, pyrimidine, pyridazine, pyrazine, 1,2,3-triazine, condensed rings thereof, and the like are mentioned; and as the aliphatic heterocycle, pyrrolidine, piperidine, piperazine, morpholine and the like are mentioned.

The two ring A's in the formula may be the same or different from each other.

Particularly, in a case where the ring A is a benzene ring and Q is a group represented by formula (1-1), the ring $\beta_{11}$ and ring $\beta_{21}$ are preferably a 7-membered ring rather than a 6-membered ring, as described later, from the viewpoint of exhibiting higher light resistance.

That is, a compound in which $L^{11}$ is a single bond and the ring $\beta_{11}$ and the ring $\beta_{21}$ have a 6-membered ring has high acidity since Q (oxygen atom) coordinated to the boron atom is a phenolic hydroxyl group, and thus the compound may be hydrolyzed in water. On the other hand, in a compound in which $L^{11}$ is, for example, a methylene group and the ring $\beta_{11}$ and the ring $\beta_{21}$ are a 7-membered ring, Q (oxygen atom) coordinated to the boron atom is a benzyl alcohol type, and thus it is speculated that the acidity of the hydroxyl group is low, hydrolysis is inhibited, and as a result, higher light resistance is maintained in water.

<Fluorescent Compound Represented by Formula (3)>

The fluorescent compound according to the embodiment of the present invention, which is represented by Formula (1), is more preferably represented by Formula (3).

Formula (3)

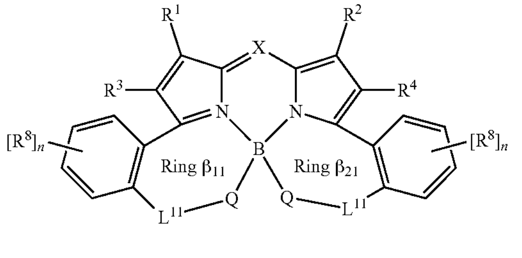

In the formula, X represents $CR^5$ or N and has the same meaning as X in Formula (1).

$R^1$ to $R^5$ and Q respectively have the same meanings as $R^1$ to $R^5$ and $Q^1$ in Formula (1), and $L^{11}$ has the same meaning as $L^{11}$ in Formula (2).

$R^8$ represents a substituent.

n is an integer of 0 to 4, preferably an integer of 0 to 3, more preferably an integer of 0 to 2, and particularly preferably 0 or 1.

However, the ring $\beta_{11}$ and the ring $\beta_{21}$ (that is, rings constituted of $L^{11}$, Q, the atom bonded to the pyrrole ring and the atom bonded to $L^{11}$ among the constituent atoms constituting the benzene ring, the boron atom, and the carbon atom bonding the benzene ring with the nitrogen atom and the nitrogen atom among the atoms constituting the pyrrole ring) are a 6- to 8-membered ring, more preferably a 6- or 7-membered ring, and still more preferably a 7-membered ring. The ring $\beta_{11}$ and the ring $\beta_{21}$ may be the same or different from each other and are preferably the same.

As the substituent that can be adopted as $R^8$, a substituent that each of the above groups that can be adopted as $L^1$ and $L^2$ may have is mentioned, and a halogen atom, a cyano group, an alkoxy group, or an oxygen atom is preferred, and a halogen atom or an alkoxy group is more preferred. In a case where a plurality of $R^8$'s are present, the plurality of $R^8$'s may be the same or different from each other.

Among them, the benzene ring represented by Formula (3) preferably has $R^8$ at the meta position on the side opposite to the pyrrole ring with respect to the bonding position with $L^{11}$, from the viewpoint that the fluorescent compound according to the embodiment of the present invention has the improved light resistance in the aqueous solution.

Among them, the benzene ring represented by Formula (3) preferably has $R^8$ at the meta position on the side opposite to the pyrrole ring with respect to the bonding position with $L^{11}$, from the viewpoint that the light resistance of the stained cells is improved in a case where the cells are stained using, as a fluorescent dye, a fluorescent labeled biological substance containing the fluorescent compound according to the embodiment of the present invention.

<Fluorescent Compound Represented by Formula (7)>

The fluorescent compound according to the embodiment of the present invention, which is represented by Formula (1), is also preferably represented by Formula (7).

Formula (7)

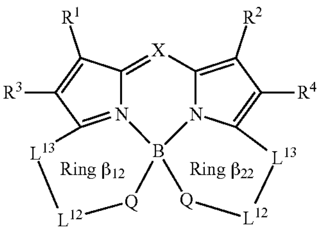

In the formula, X represents $CR^5$ or N and has the same meaning as X in Formula (1).

$R^1$ to $R^5$ and Q respectively have the same meanings as $R^1$ to $R^5$ and $Q^1$ in Formula (1).

$L^{12}$ represents a single bond or an alkylene group, an alkenylene group, an arylene group, a heteroarylene group, a cycloalkylene group, a divalent aliphatic heterocyclic group, or a group represented by any one of Formulae (1-1) to (1-8), or a linking group formed by combining two of these groups.

$L^{13}$ represents a methylene group or a group represented by any one of Formulae (1-1) to (1-8).

However, the ring $\beta_{12}$ and the ring $\beta_{22}$ (that is, rings constituted of $L^{12}$, $L^{13}$, Q, the boron atom, and the carbon atom bonding $L^{13}$ with the nitrogen atom and the nitrogen atom among the atoms constituting the pyrrole ring) are a 5- to 8-membered ring, more preferably a 6- or 7-membered ring, and still more preferably a 7-membered ring. The ring $\beta_{12}$ and the ring $\beta_{22}$ may be the same or different from each other and are preferably the same.

In the formula, the two $L^{11}$'s may be the same or different from each other, and the two $L^{13}$'s may be the same or different from each other.

Regarding an alkylene group, arylene group, heteroarylene group, cycloalkylene group, and divalent aliphatic heterocyclic group, all of which can be adopted as $L^{12}$ the descriptions of the alkylene group, arylene group, heteroarylene group, cycloalkylene group, and divalent aliphatic heterocyclic group for $L^{11}$ can be applied respectively.

$L^{12}$ is preferably an alkylene group, an alkenylene group, an arylene group, a heteroarylene group, a cycloalkylene group, a divalent aliphatic heterocyclic group, or a linking group formed by combining an alkylene group with any one of Formulae (1-1), . . . , or (1-8), more preferably an alkylene group, an alkenylene group, an arylene group, a heteroarylene group, a cycloalkylene group, a divalent aliphatic heterocyclic group, or a linking group formed by combining an alkylene group with Formula (1-3) or (1-4), still more preferably an alkylene group, an alkenylene group, an arylene group, a heteroarylene group, a cycloalkylene group, or a divalent aliphatic heterocyclic group, particularly preferably an alkylene group or a cycloalkylene group, and most preferably an alkylene group.

The number of carbon atoms of the alkylene group is preferably 1 or 2.

The methylene group that can be adopted as $L^{13}$ may have a substituent.

$L^{13}$ is preferably a methylene group or a group represented by any one of Formulae (1-4), . . . , or (1-7), more preferably a methylene group or a group represented by Formula (1-1) or Formula (1-3), still more preferably a methylene group or a group represented by Formula (1-1), and particularly preferably a methylene group.

<Fluorescent Compound Represented by Formula (9)>

The fluorescent compound according to the embodiment of the present invention, which is represented by Formula (1), is also preferably represented by Formula (9).

Formula (9)

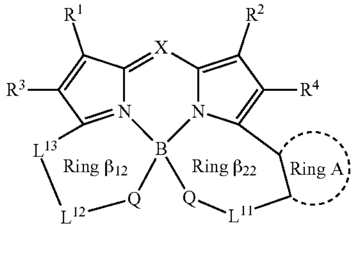

The fluorescent compound represented by Formula (9) is the same as the compound represented by Formula (2)

describe above, except that the fluorescent compound has the ring $\beta_{12}$ in Formula (7) instead of the ring $\beta_{11}$ in Formula (2).

Accordingly, X, $R^1$ to $R^5$, the ring $\beta_{21}$, and $L^{11}$, Q, and the ring A, which constitute the ring $\beta_{21}$, in Formula (9) are respectively the same as X, $R^1$ to $R^5$, the ring $\beta_{21}$, and $L^{11}$, Q, and the ring A, which constitute the ring $\beta_{21}$, in Formula (2), and the same applies to the preferred ones.

Further, in Formula (9), the ring $\beta_{12}$ and $L^{12}$, $L^{13}$, and Q, which constitute the ring $\beta_{12}$, are respectively the same as the ring $\beta_{12}$ and $L^{12}$, $L^{13}$, and Q, which constitute the ring $\beta_{12}$, in Formula (7), and the same applies to the preferred ones.

<Fluorescent Compound Represented by Formula (4)>

The fluorescent compound according to the embodiment of the present invention, which is represented by Formula (4), is as follows.

Formula (4)

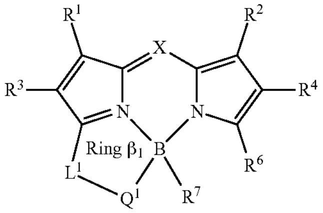

The fluorescent compound represented by Formula (4) is the same as the fluorescent compound represented by Formula (1), except that it does not have a ring structure constituted of the carbon atom and the nitrogen atom adjacent to each other in the pyrrole ring, the boron atom, $L^2$, and $Q^2$.

Accordingly, X, $R^1$ to $R^5$, $L^1$, $Q^1$, and the ring $\beta_1$ in Formula (4) are respectively the same as X, $R^1$ to $R^5$, $L^1$, $Q^1$, and the ring $\beta_1$ in Formula (1), and the same applies to the preferred ones.

However, in Formula (4), at least one of $R^1$ to $R^7$, $L^1$, or $Q^1$ has at least one of a carboxy group or a salt thereof, a sulfo group or a salt thereof, a phosphono group or a salt thereof, an onio group, or a polyamino acid residue, that is, the specific hydrophilic group Pi described above.

In Formula (4), $R^6$ has the same meaning as $R^1$ in Formula (1). However, $R^6$ is preferably a hydrogen atom, an alkyl group, an alkoxy group, an aryl group, a halogen atom, or a heteroaryl group.

$R^7$ represents an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, or a halogen atom. These groups or atoms that can be adopted as $R^7$ have the same meanings as the corresponding groups or atoms that can be taken as $R^1$, and the same applies to the preferred ones. However, $R^7$ is preferably a halogen atom, an alkynyl group, an alkoxy group, a hydroxyl group, or an aryl group and more preferably a halogen atom or a hydroxyl group.

Each of the above groups that can be adopted as $R^6$ and $R^7$ may be each an unsubstituted group or a group having a substituent. The substituent that each of the above groups that may be adopted as $R^6$ and $R^7$ may have is not particularly limited and preferably selected from the substituent group T, more preferably an alkyl group, an alkoxy group, a carbamoyl group (these alkyl group, alkoxy group, and carbamoyl group may be an unsubstituted group or a group having a substituent, and the substituent that these alkyl group and alkoxy group may have is not particularly limited and is preferably selected from the substituent group T described later and more preferably a hydrophilic group Pi.) or a specific hydrophilic group Pi. The number of substituents is not particularly limited as long as it is one or more.

$R^6$ and $R^7$ do not bond, directly or via a linking group, to each other to form a ring. The ring means a ring constituted of the carbon atom and the nitrogen atom adjacent to each other in the pyrrole ring, the boron atom, $L^2$, and $Q^2$, that is the ring n in the fluorescent compound represented by Formula (1), and a ring may be formed as long as the ring described is not the ring $\beta_{11}$.

<Fluorescent Compound Represented by Formula (5)>

The fluorescent compound according to the embodiment of the present invention, which is represented by Formula (4), is preferably represented by Formula (5).

Formula (5)

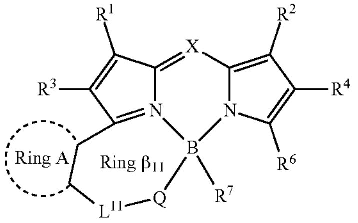

The fluorescent compound represented by Formula (5) is the same as the compound represented by Formula (2) describe above, except that $R^6$ and $R^7$ do not bond to each other to form a ring and the fluorescent compound does not have the ring $\beta_{21}$ in Formula (2).

Accordingly, X, $R^1$ to $R^5$, $L^{11}$, Q, and the ring $\beta_{11}$, and the ring A in Formula (5) are respectively the same as X, $R^1$ to $R^5$, $L^{11}$, Q, and the ring $\beta_{11}$ in Formula (2), and the same applies to the preferred ones.

In Formula (5), $R^6$ and $R^7$ have the same meanings as $R^6$ and $R^7$ in Formula (4), and the same applies to the preferred ones.

<Fluorescent Compound Represented by Formula (6)>

The fluorescent compound according to the embodiment of the present invention, which is represented by Formula (4), is more preferably represented by Formula (6).

Formula (6)

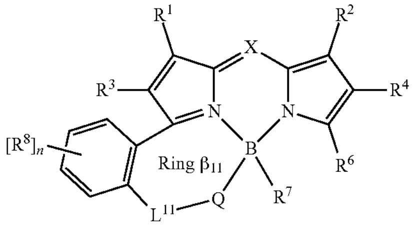

The fluorescent compound represented by Formula (6) is the same as the compound represented by Formula (3) describe above, except that $R^6$ and $R^7$ do not bond to each other to form a ring and the fluorescent compound does not have the ring $\beta_{21}$ in Formula (3).

Accordingly, X, $R^1$ to $R^5$, $R^8$, $L^{11}$, Q, n, and the ring $\beta_{11}$ in Formula (5) are respectively the same as X, $R^1$ to $R^5$, $R^8$, $L^{11}$, Q, n, and the ring $\beta_{11}$ in Formula (3), and the same applies to the preferred ones.

In Formula (6), $R^6$ and $R^7$ have the same meaning as $R^6$ and $R^7$ in Formula (4), the same applies to the preferred ones.

<Fluorescent Compound Represented by Formula (8)>

The fluorescent compound according to the embodiment of the present invention, which is represented by Formula (4), is also preferably represented by Formula (8).

Formula (8)

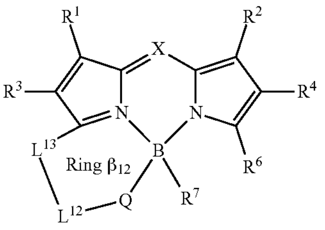

The fluorescent compound represented by Formula (8) is the same as the compound represented by Formula (7) describe above, except that $R^6$ and $R^7$ do not bond to each other to form a ring and the fluorescent compound does not have the ring $\beta_{22}$ in Formula (7).

Accordingly, X, $R^1$ to $R^5$, $L^{12}$, $L^{13}$, Q, and the ring $\beta_{12}$ in Formula (8) are respectively the same as X, $R^1$ to $R^5$, $L^{12}$, $L^{13}$, Q, and the ring $\beta_{12}$ in Formula (7), and the same applies to the preferred ones.

In Formula (8), $R^6$ and $R^7$ have the same meanings as $R^6$ and $R^7$ in Formula (4), and the same applies to the preferred ones.

The fluorescent compound represented by any one of Formula (7) or Formula (8) has the above-described specific group as $L^{13}$ in the ring $\beta_{12}$ or the ring $\beta_{22}$, whereby R-conjugation of the dipyrromethene skeleton is not elongated as compared with a compound having an arylene group and a heteroarylene group at the position of $L^{13}$, and thus the fluorescent compound represented by any one of Formula (7) or Formula (8) among the fluorescent compounds according to the embodiment of the present invention can be used as a fluorescent compound having an excitation wavelength or an emission wavelength on a shorter wavelength side.

Specific examples of the fluorescent compounds according to the embodiment of the present invention, which are respectively represented by Formula (1) and Formula (4), are shown below, but the present invention is not limited to these compounds. In the following specific examples, a group having a dissociative hydrogen atom such as a specific hydrophilic group Pi may adopt a salt structure by dissociating the dissociative hydrogen atom. In addition, m in the structural formula is an average number of repetitions and represents 0 to 10,000.

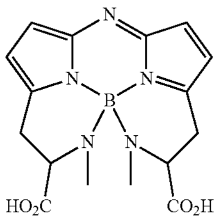

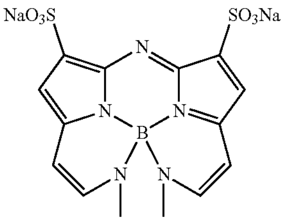

-continued

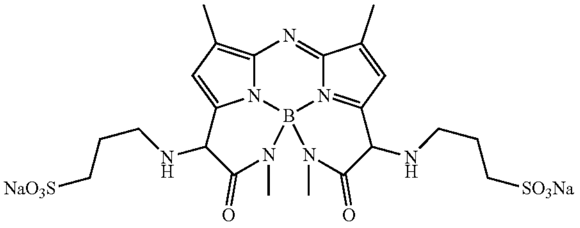

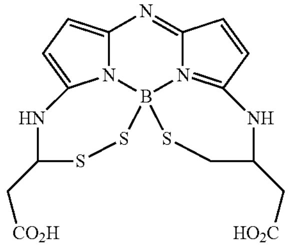

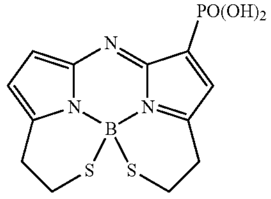

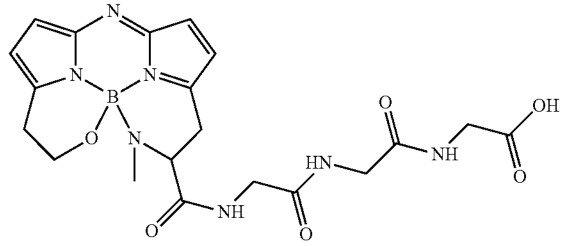

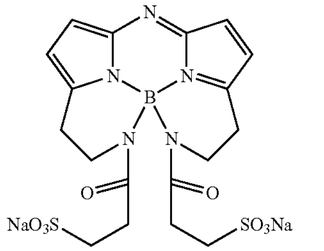

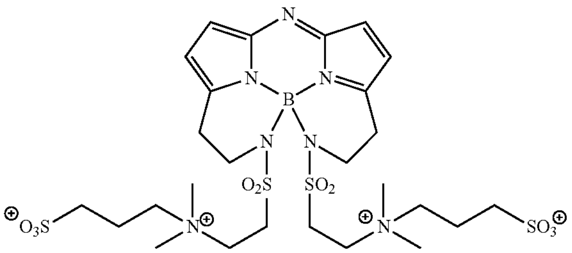

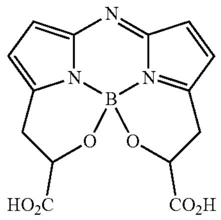

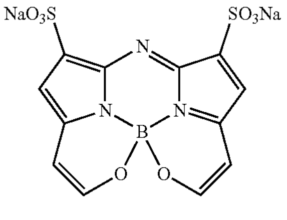

-continued
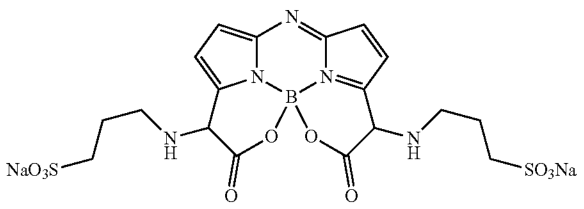
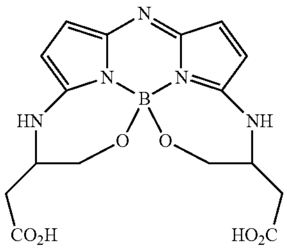
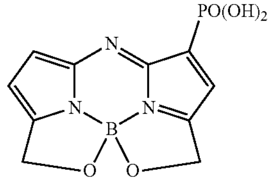
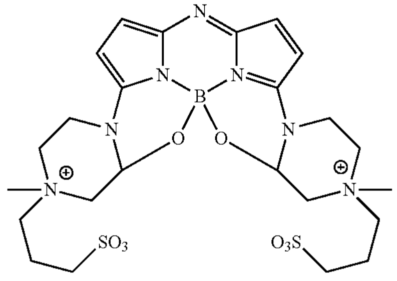
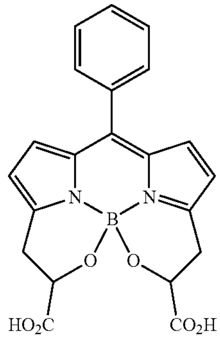
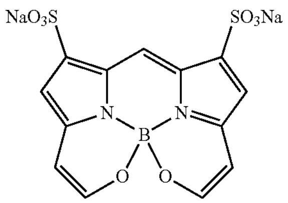
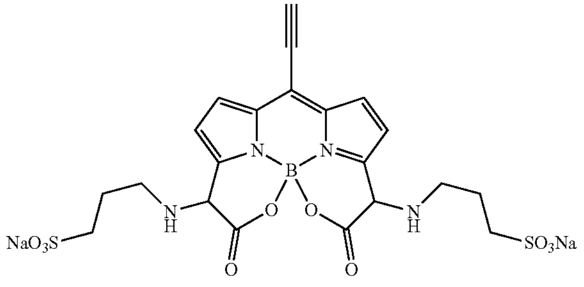
-continued
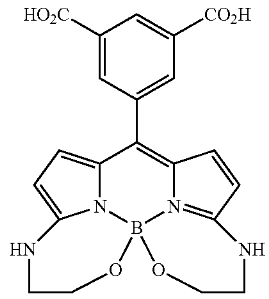
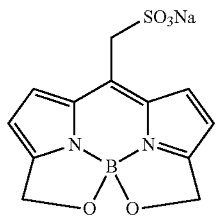
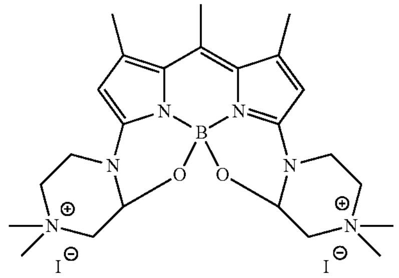
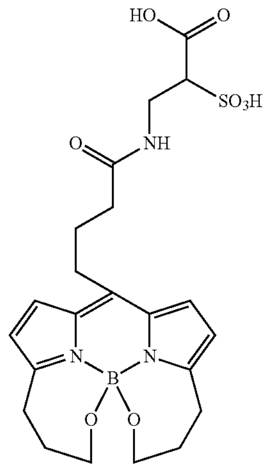
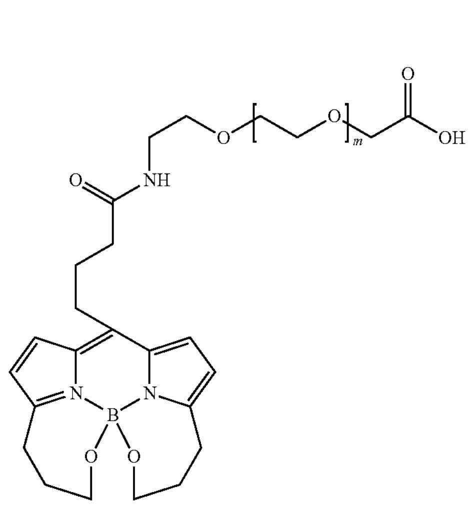

-continued
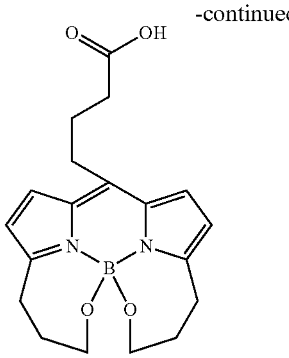
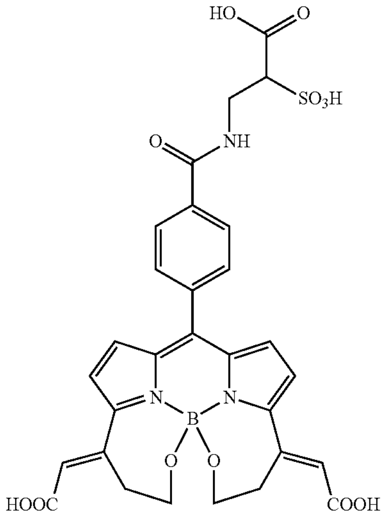
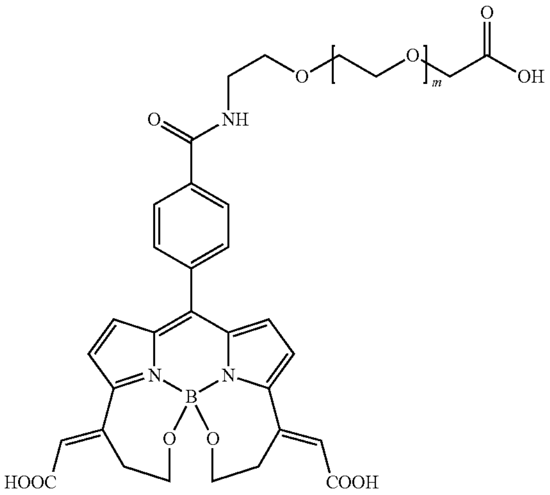
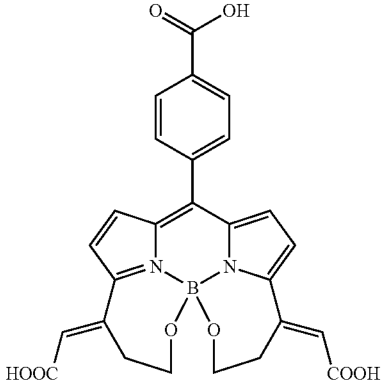
-continued
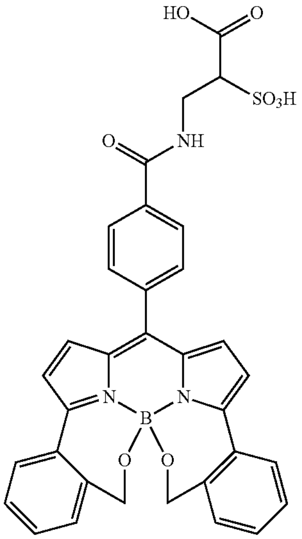
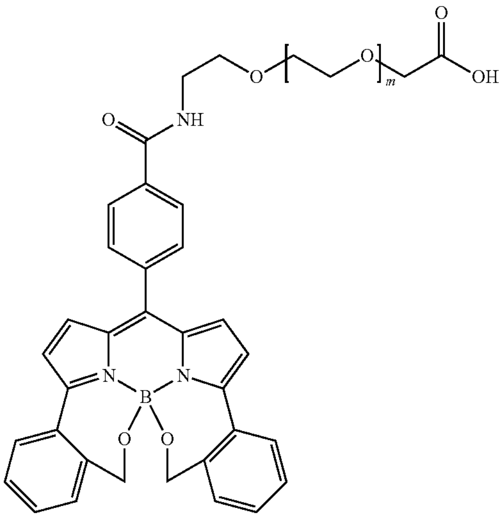
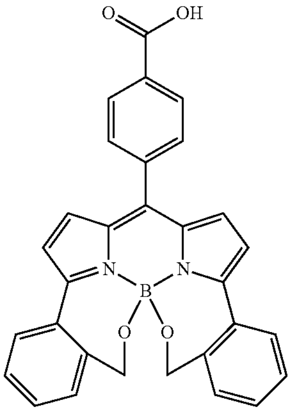
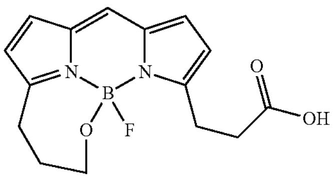

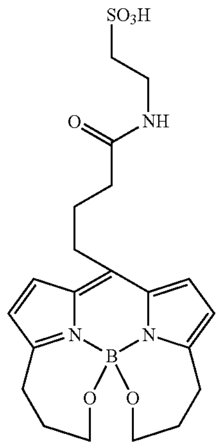
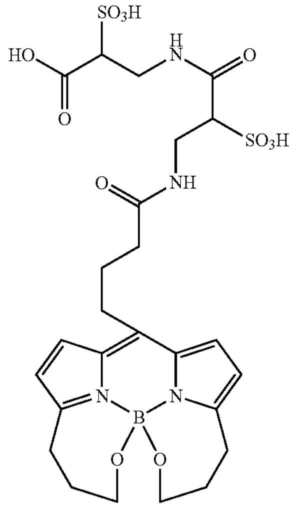
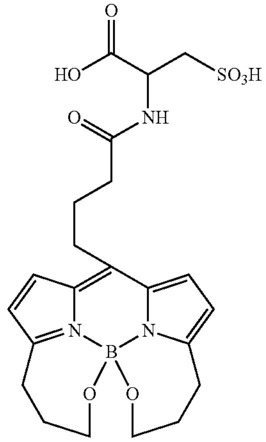
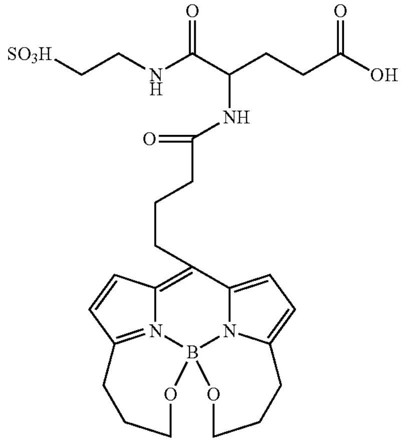
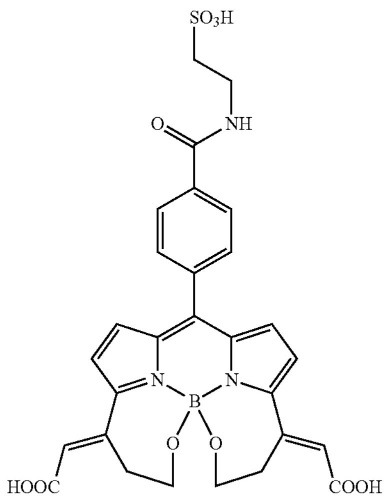
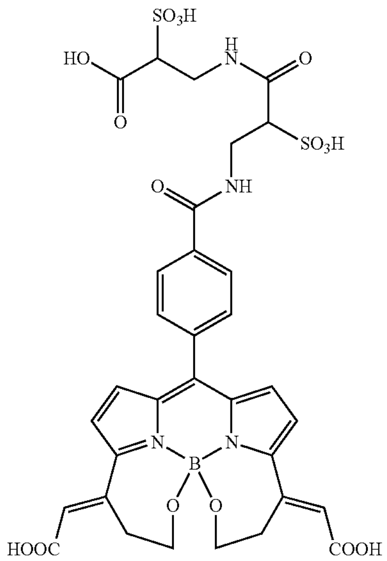

-continued
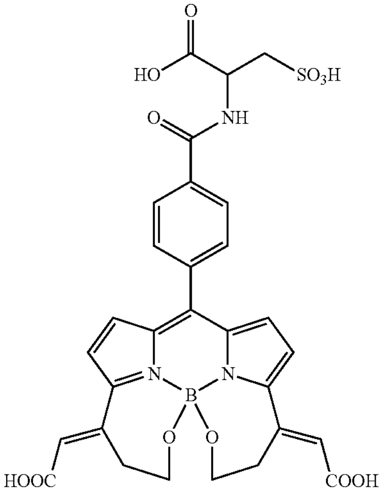
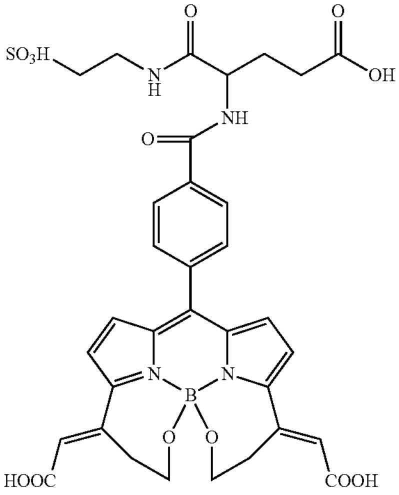
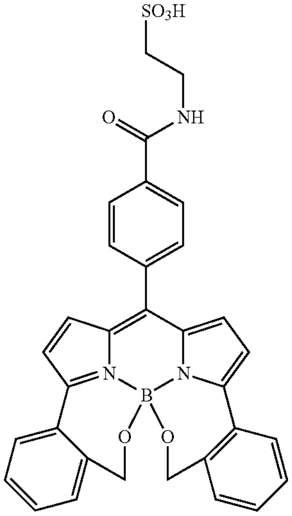
-continued
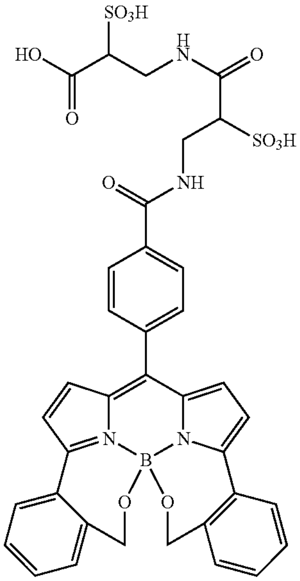
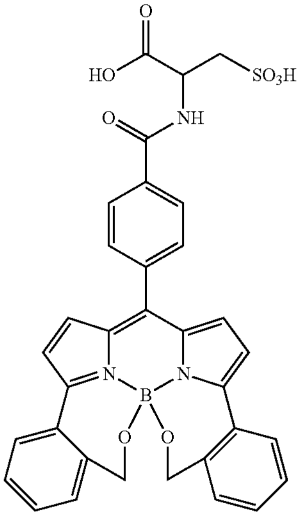
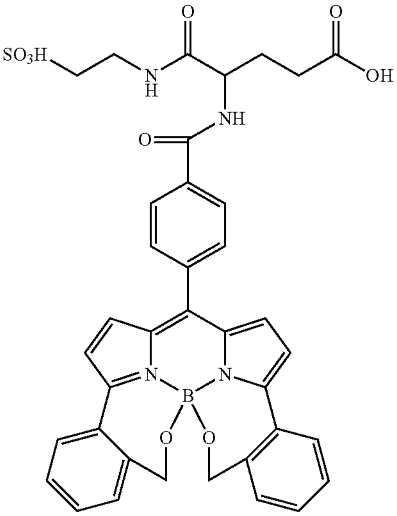

-continued
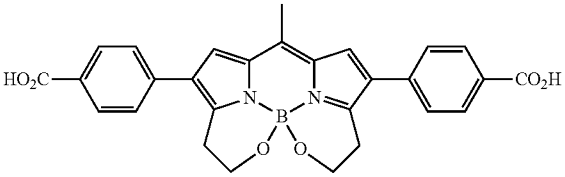
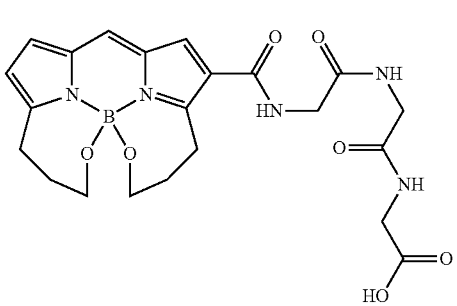
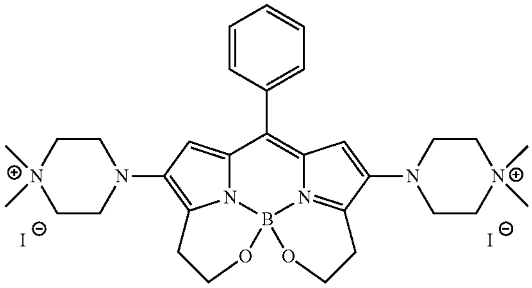
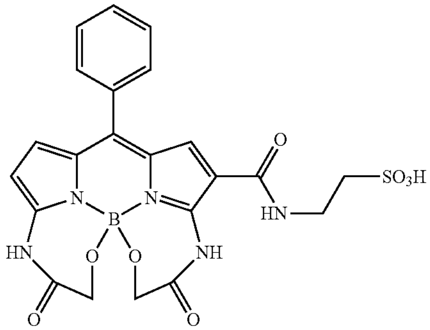
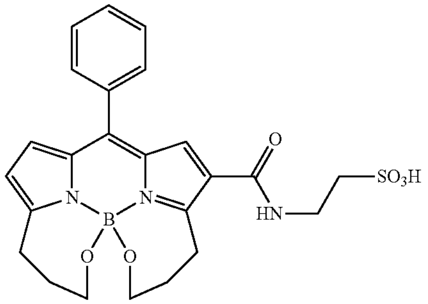
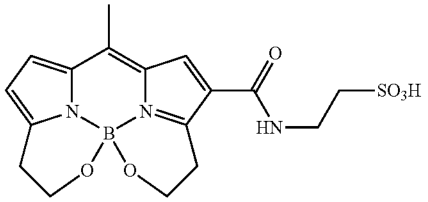
-continued
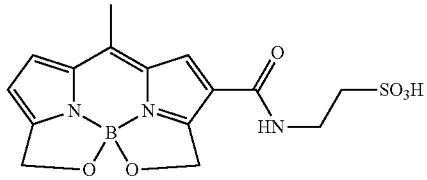
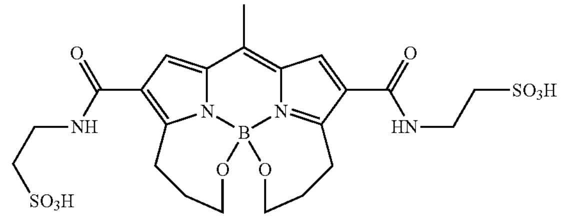
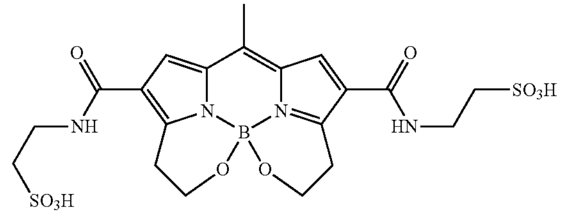
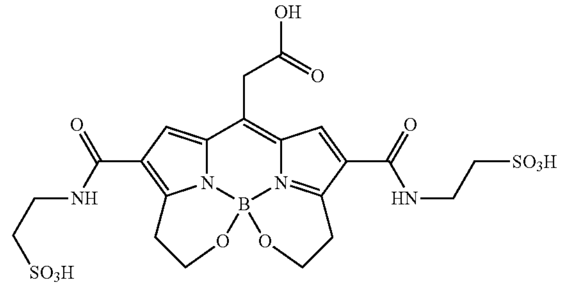
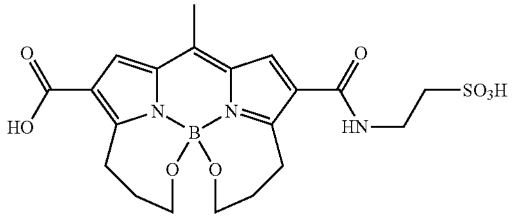
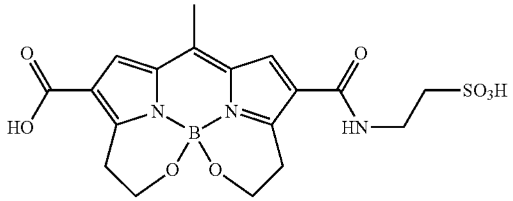
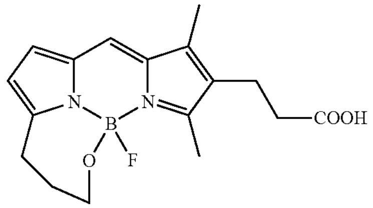
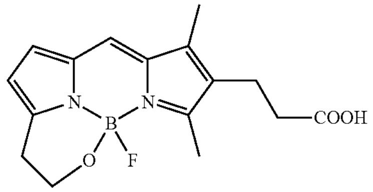

-continued
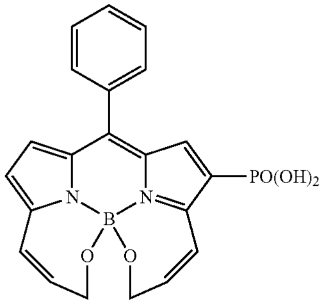
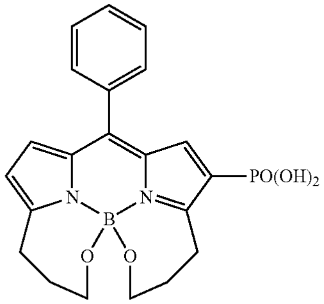
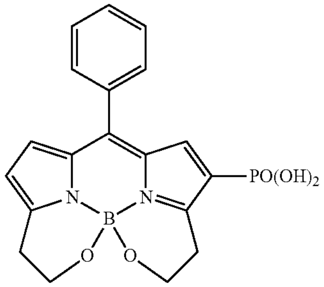
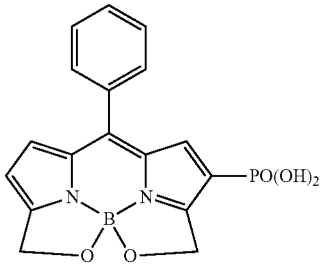
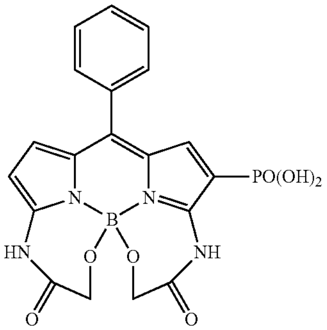
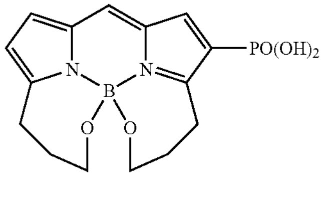
-continued
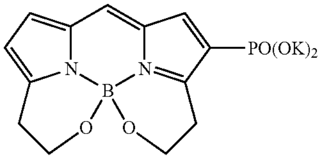
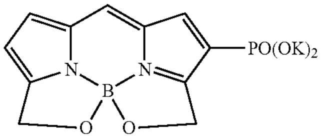
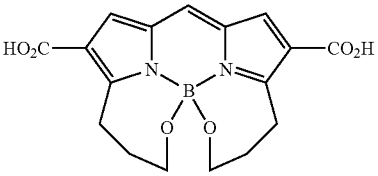
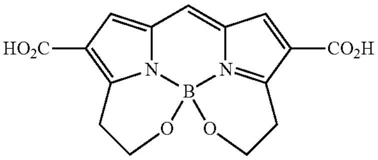
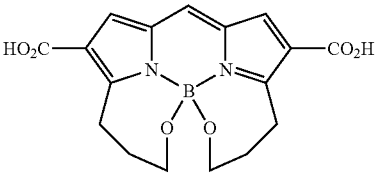
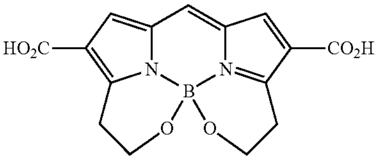
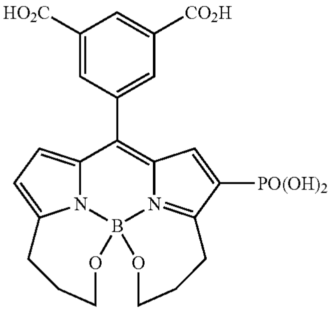
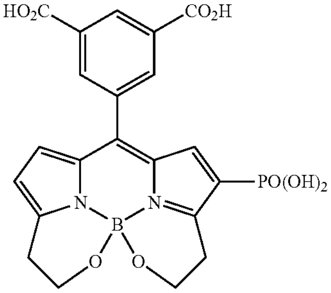

-continued
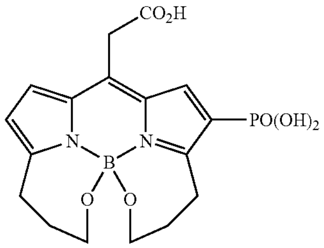
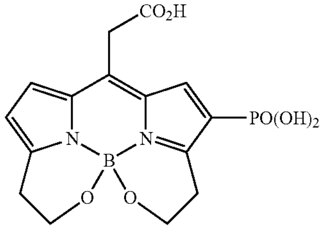
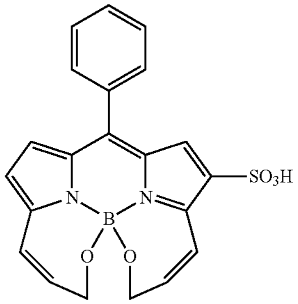
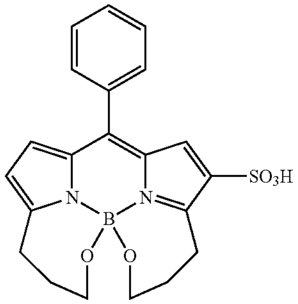
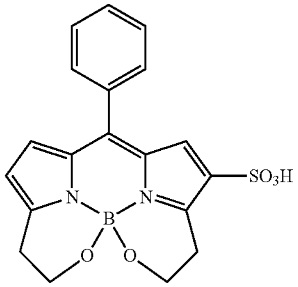
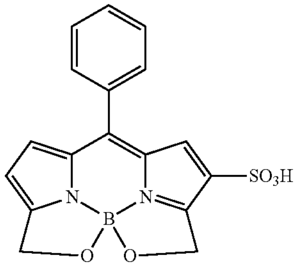
-continued
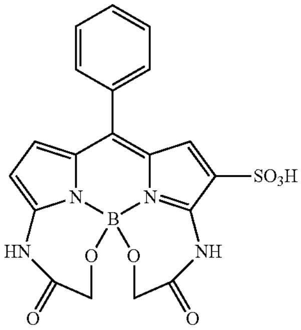
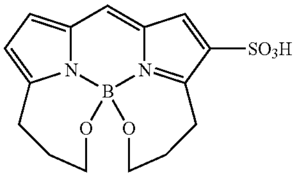
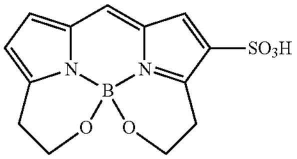
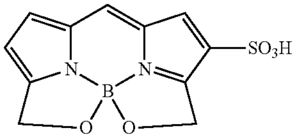
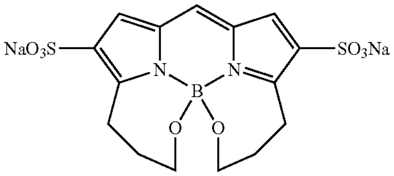
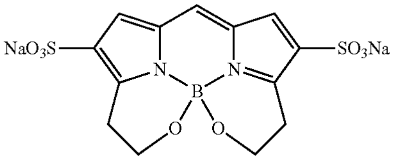
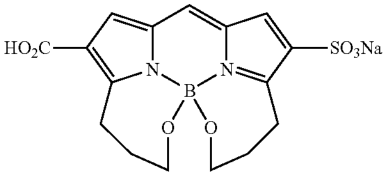
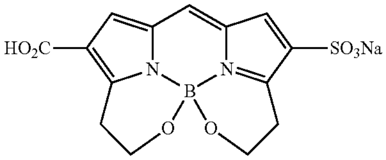

-continued
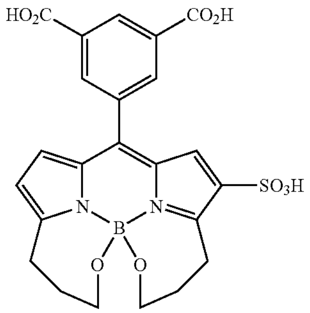
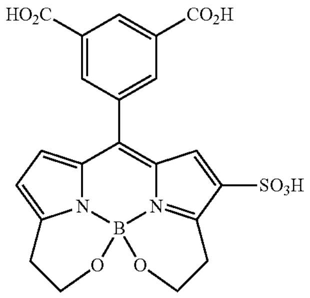
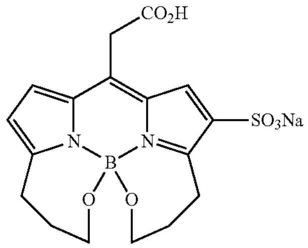
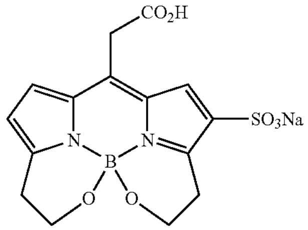
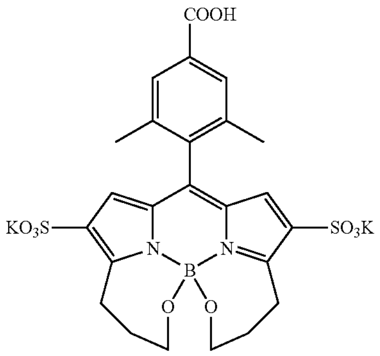
-continued
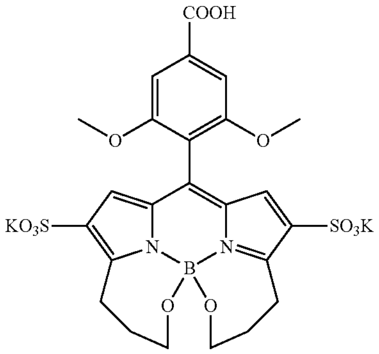
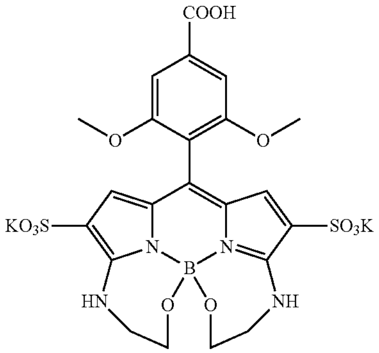
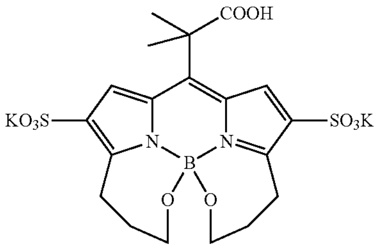
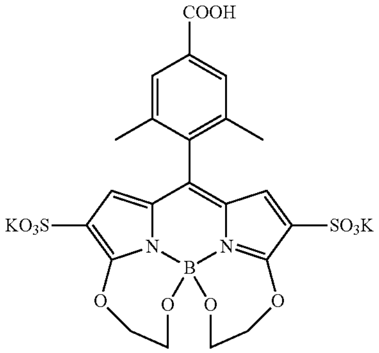
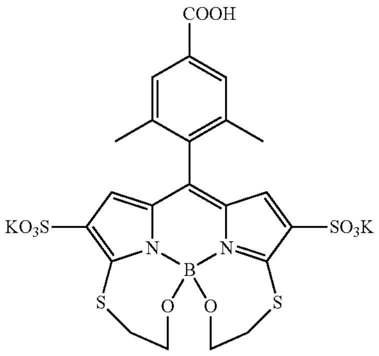

-continued
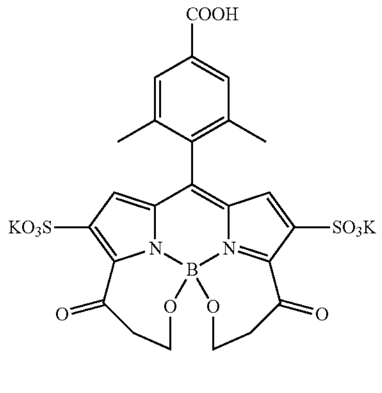
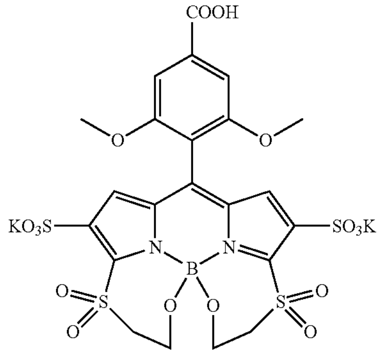
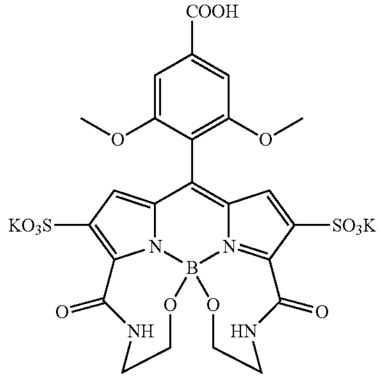
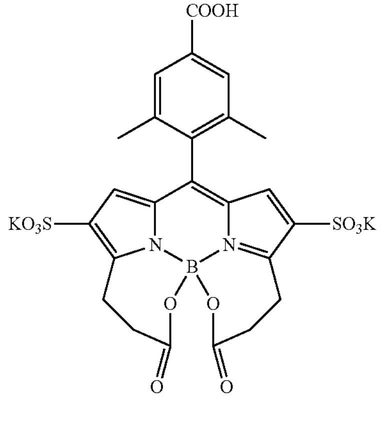
-continued
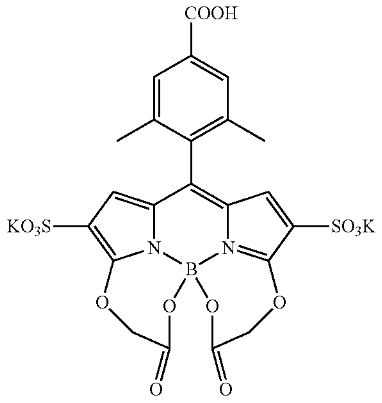
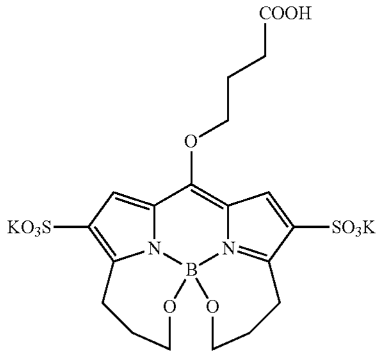
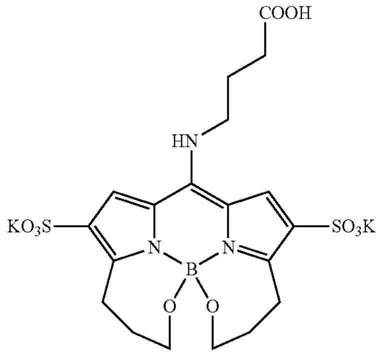
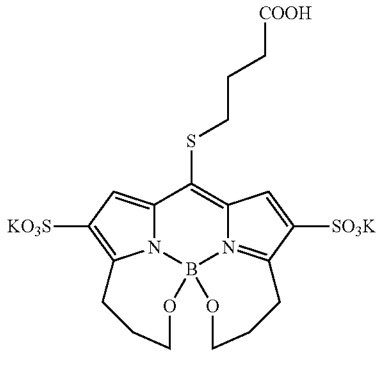

-continued
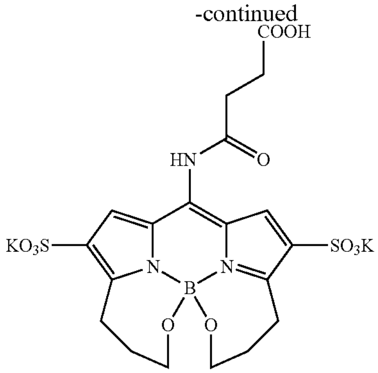
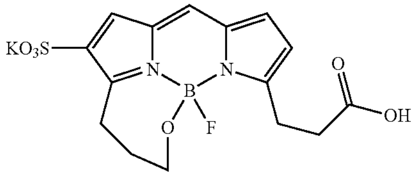
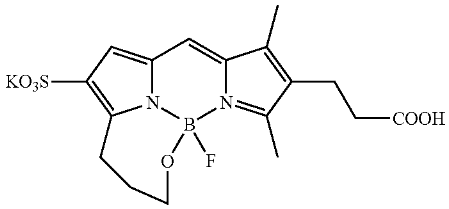
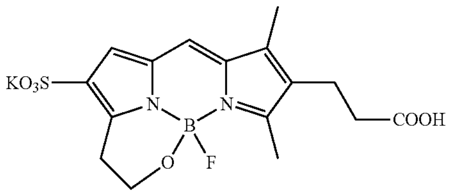
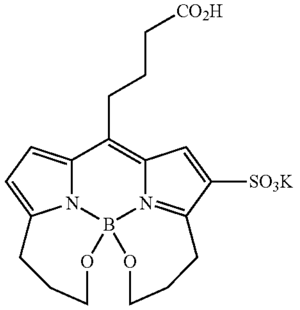
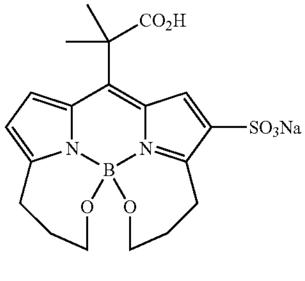
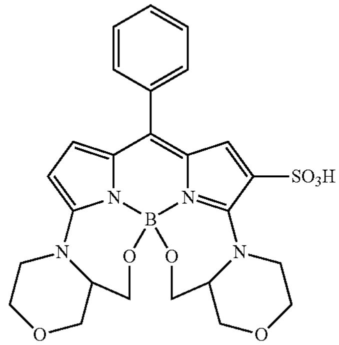
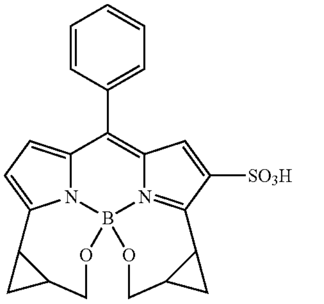
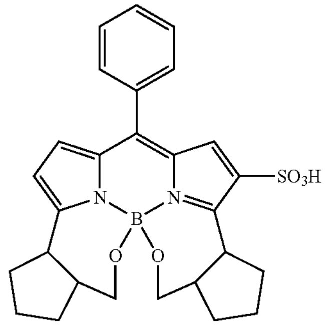
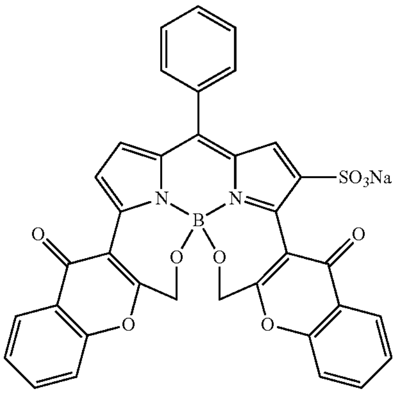
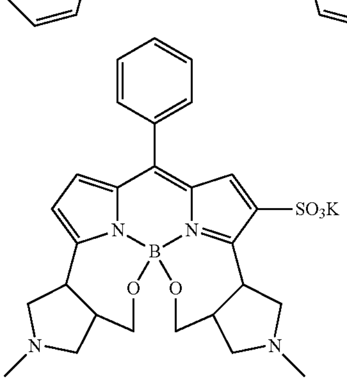

-continued
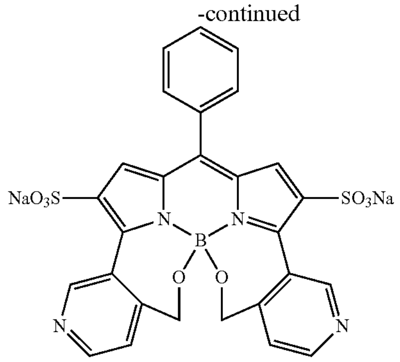
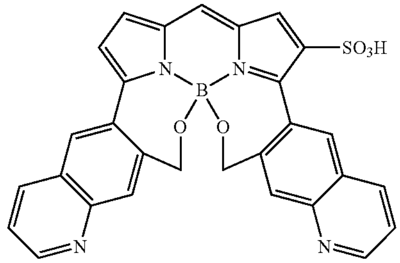
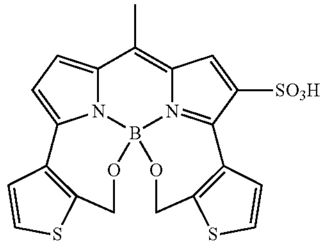
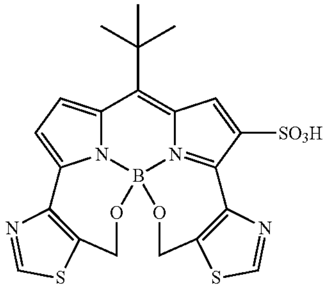
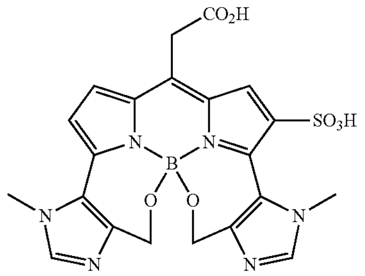
-continued
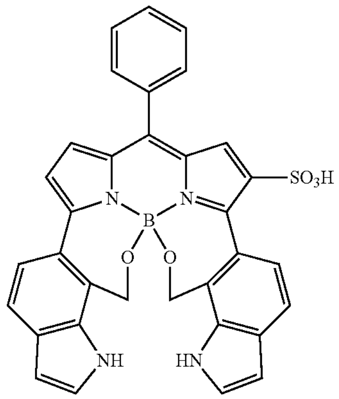
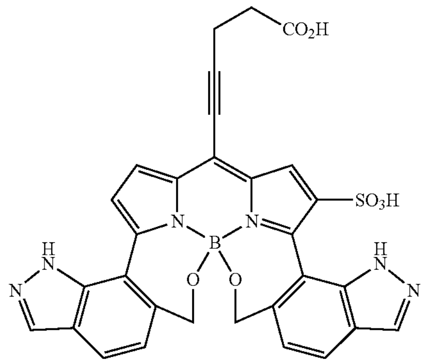
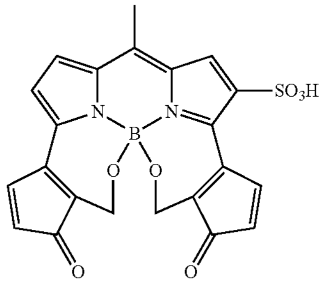
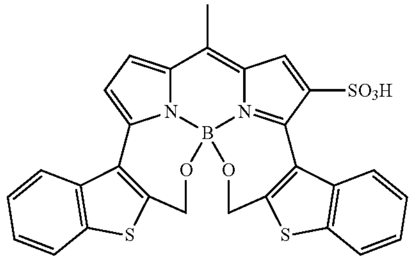
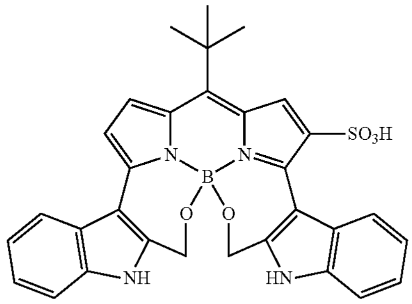

-continued
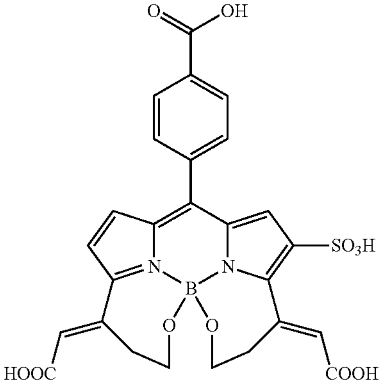
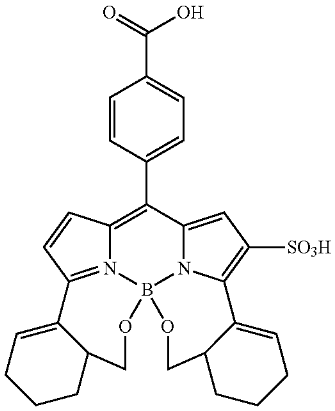
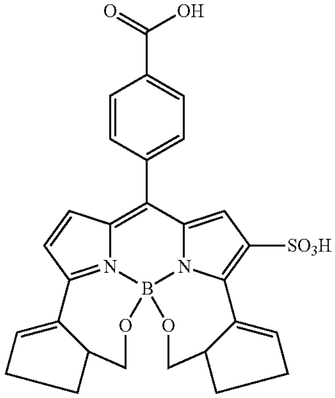
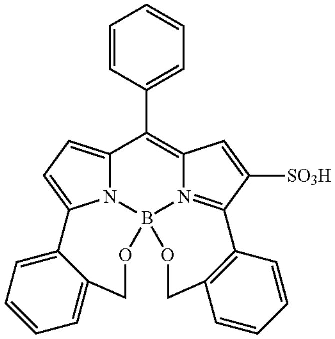
-continued
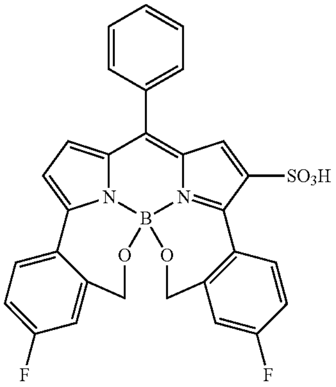
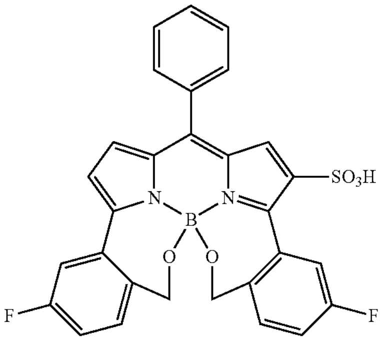
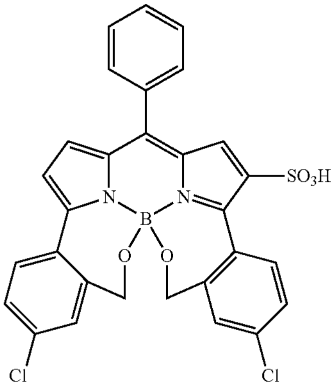
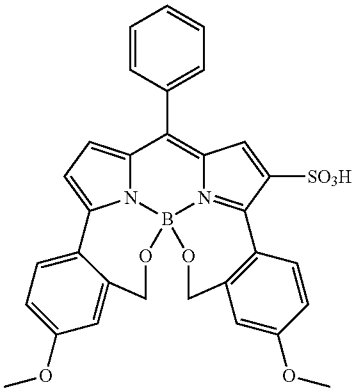

-continued
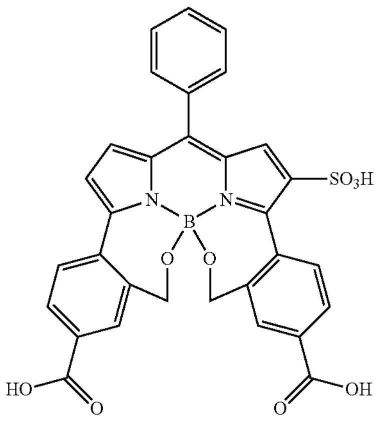
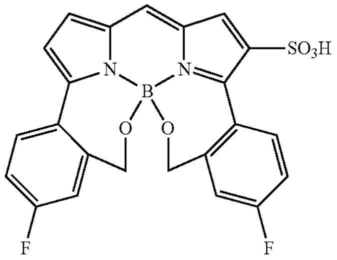
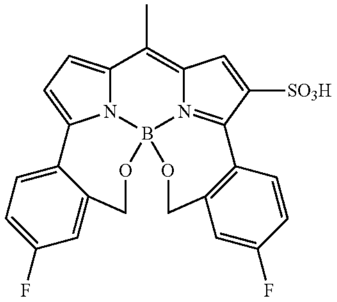
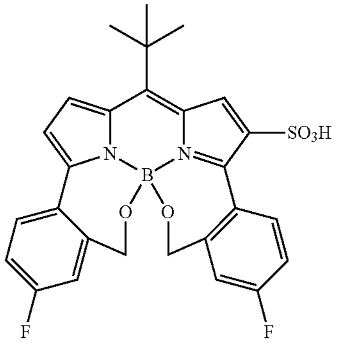
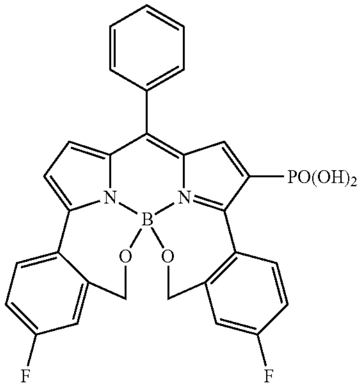
-continued
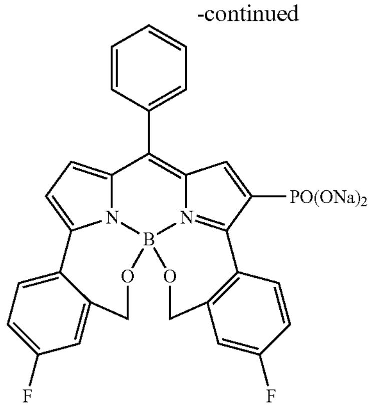
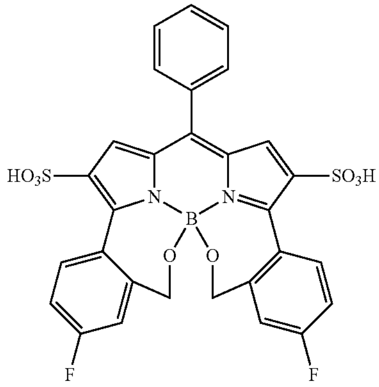
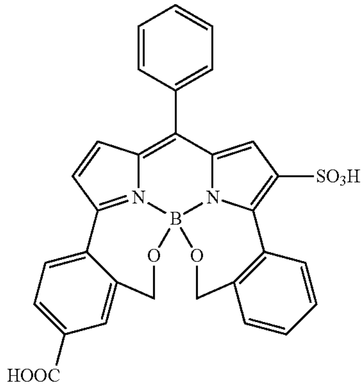
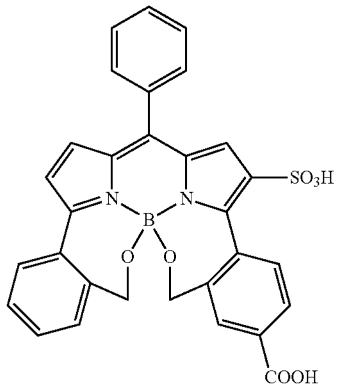

-continued
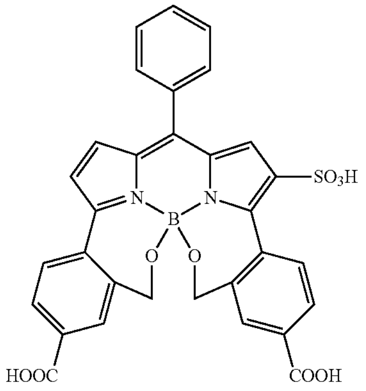
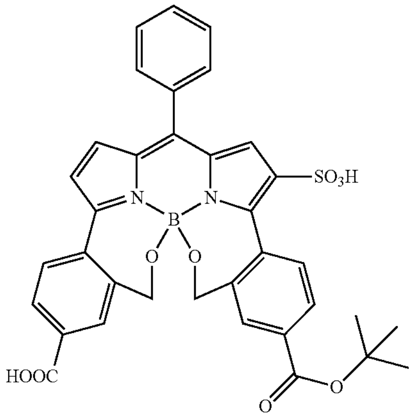
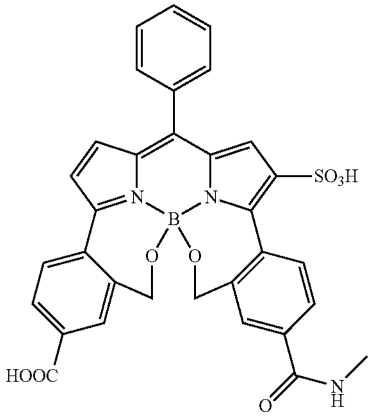
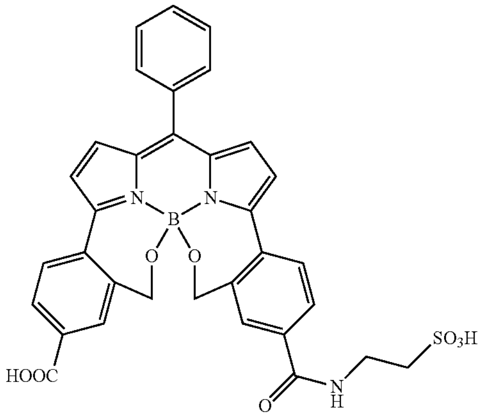
-continued
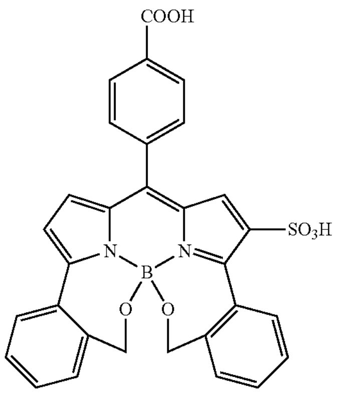
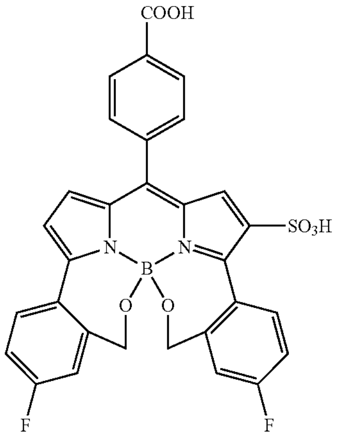
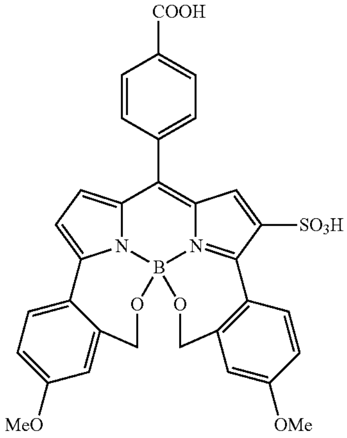
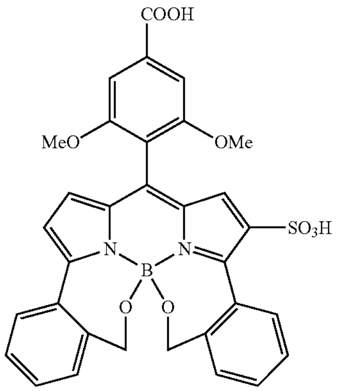

-continued
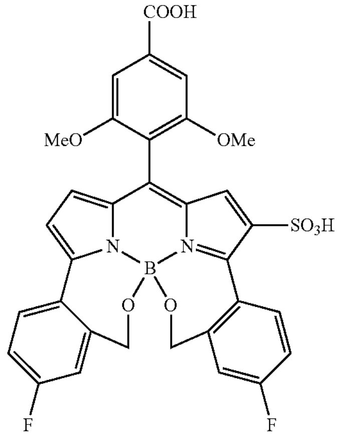
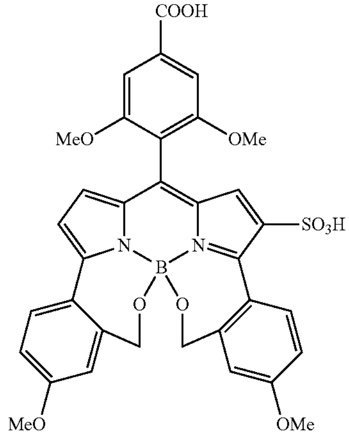
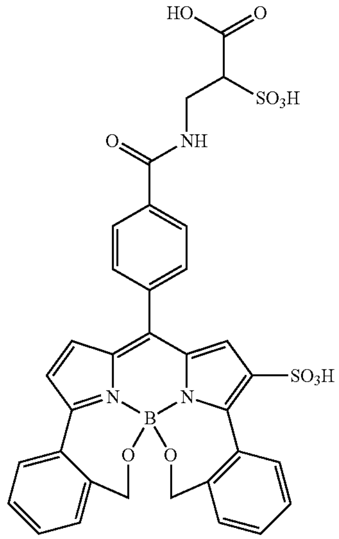
-continued
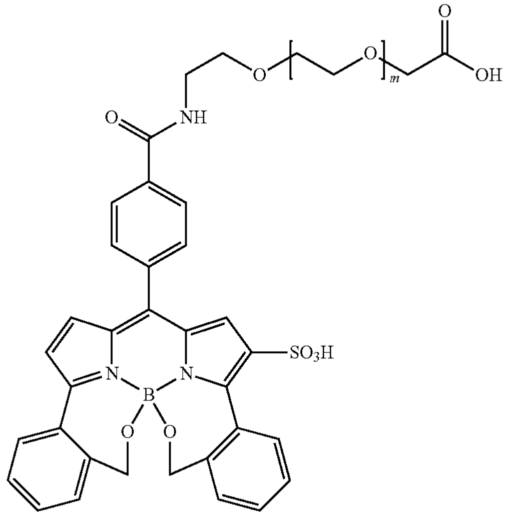
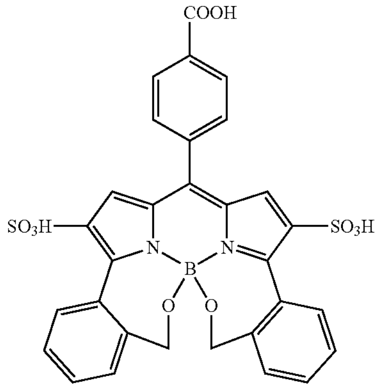
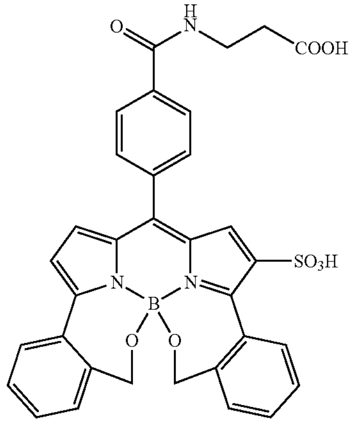

-continued
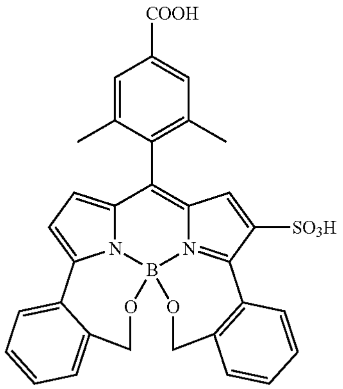
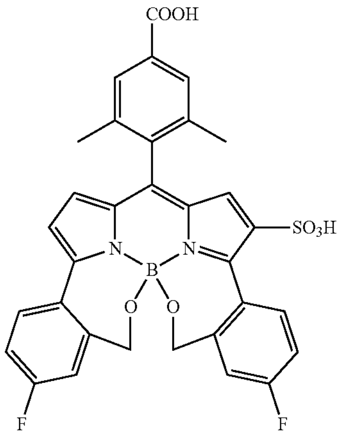
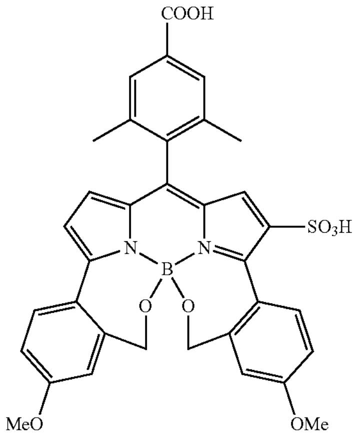
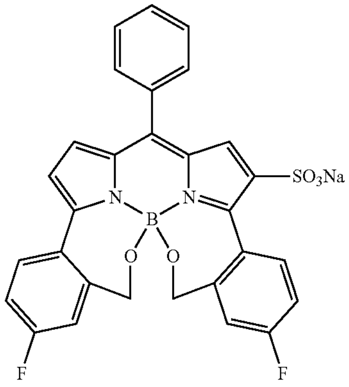
-continued
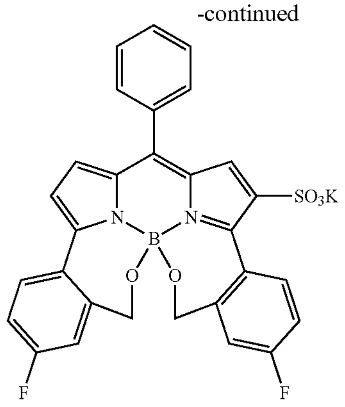
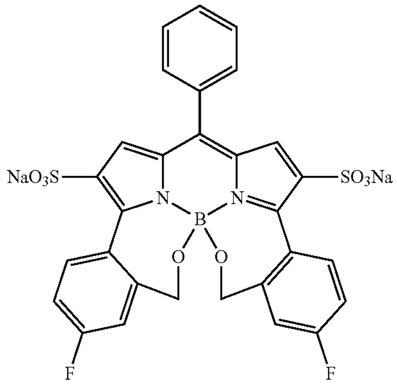
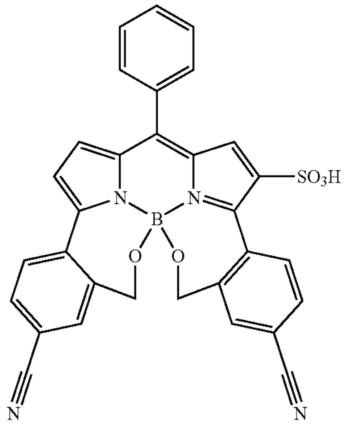
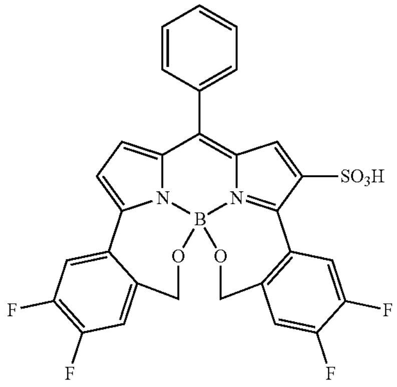

-continued
-continued
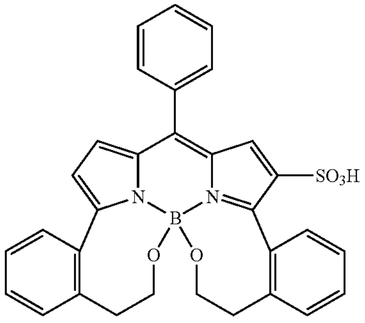
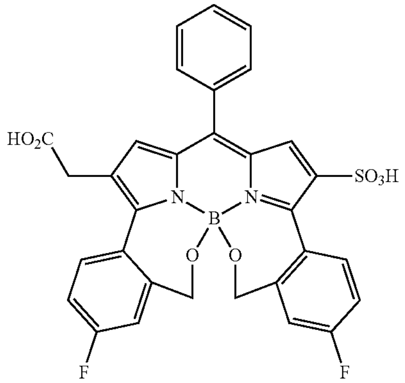
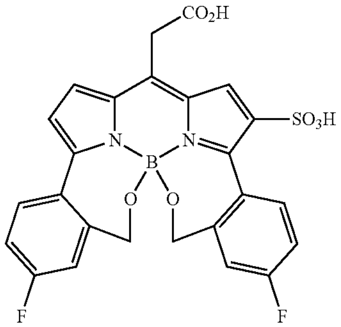
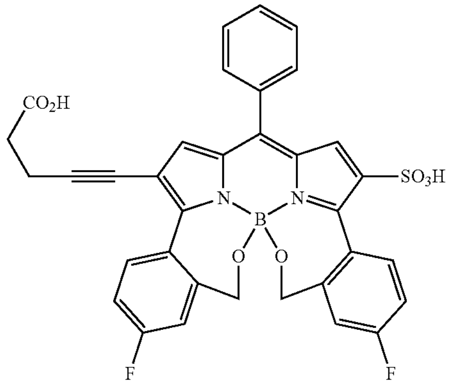
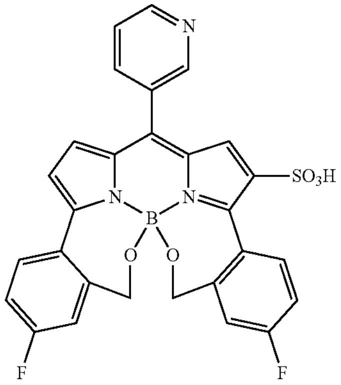
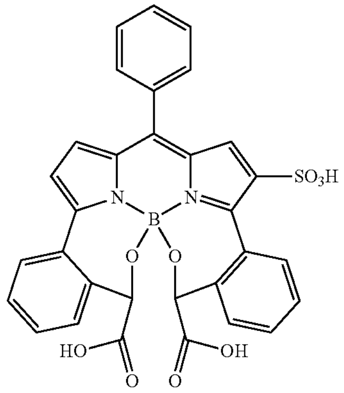
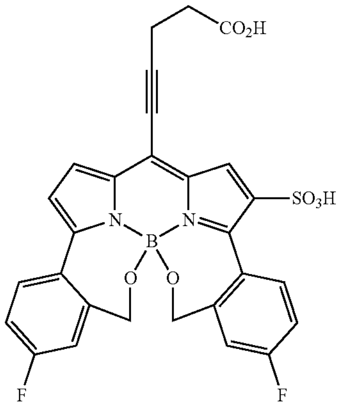
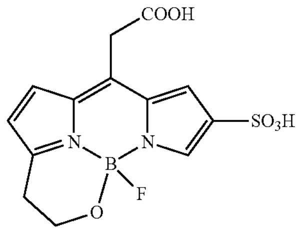
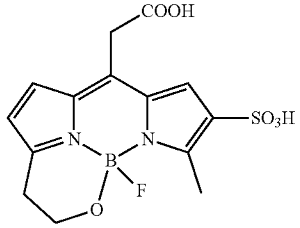

-continued
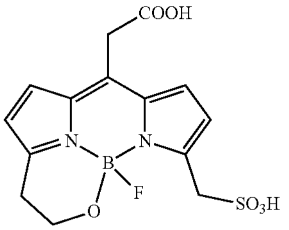
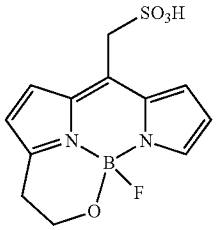
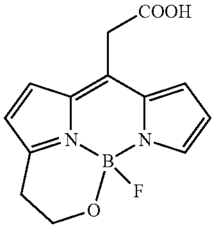
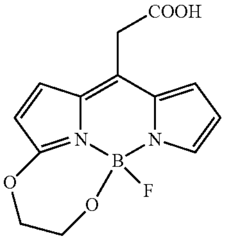
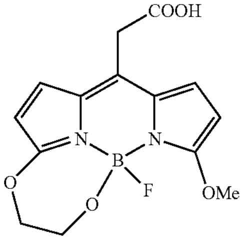
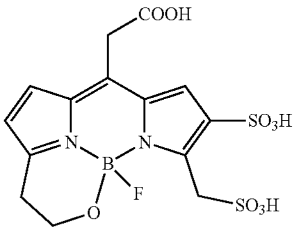
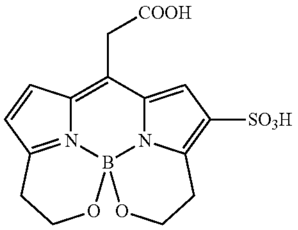
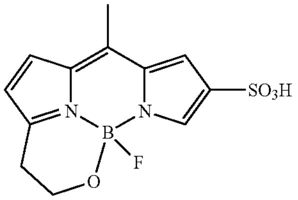
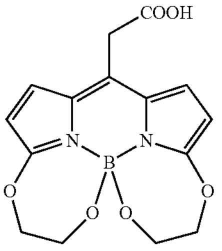
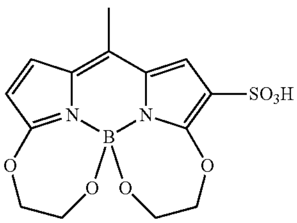
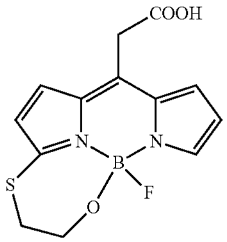
-continued
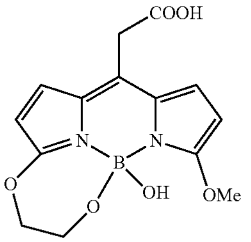
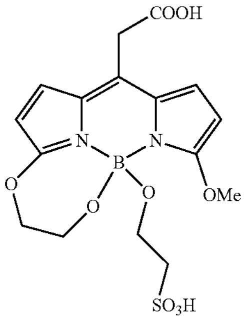
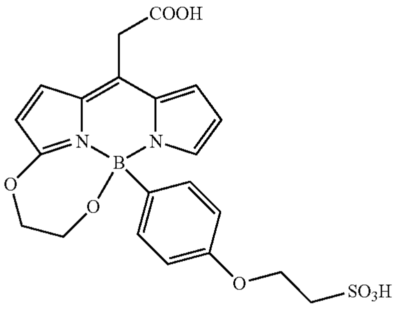
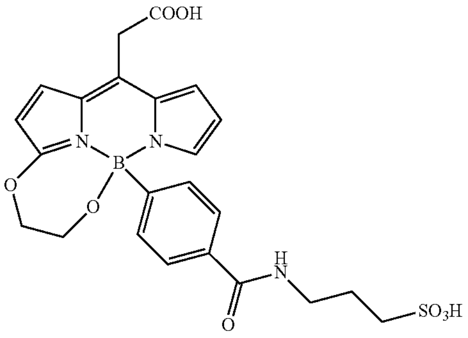
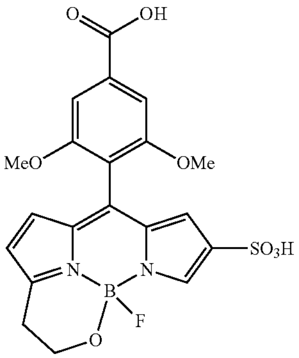
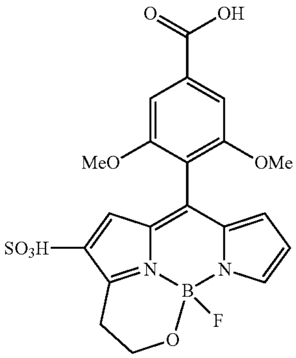

-continued
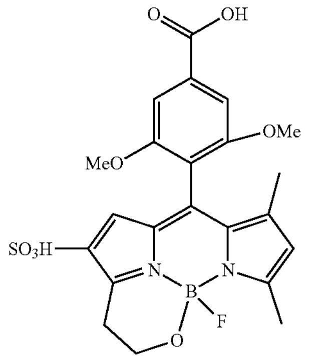
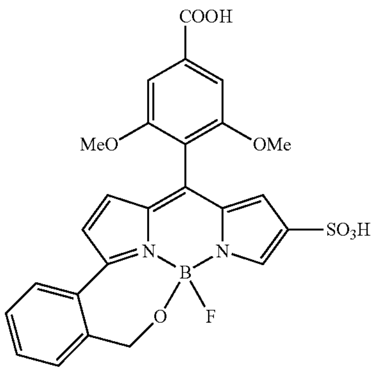
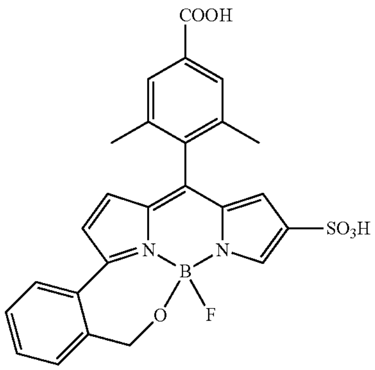
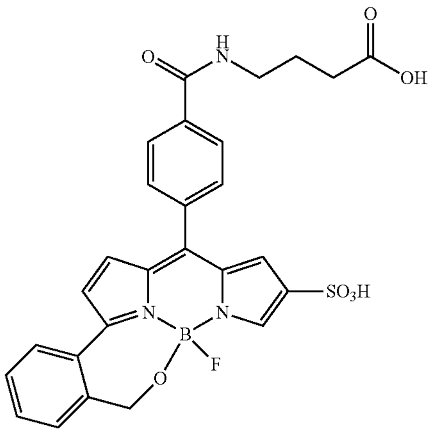
-continued
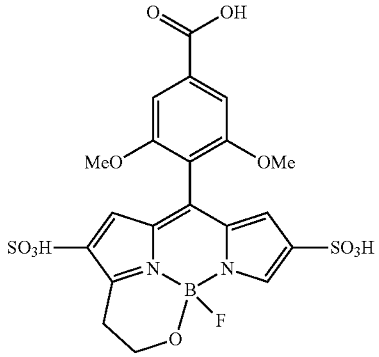
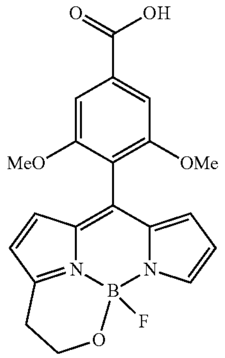
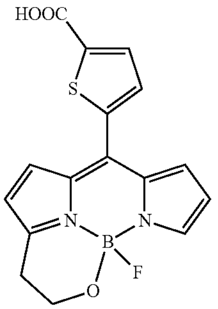
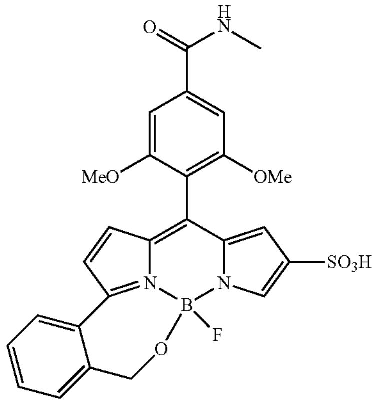
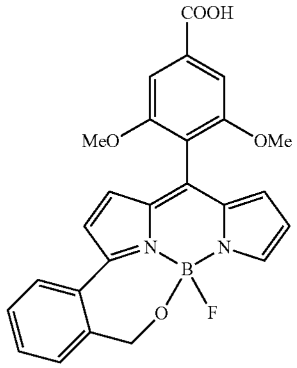

-continued
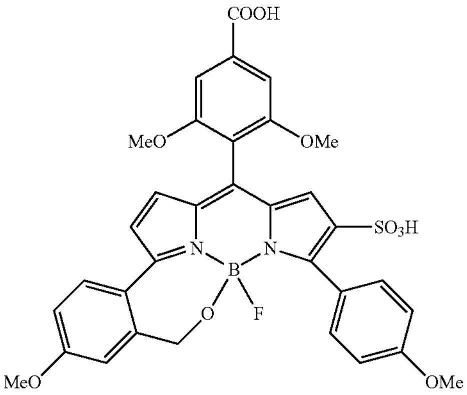
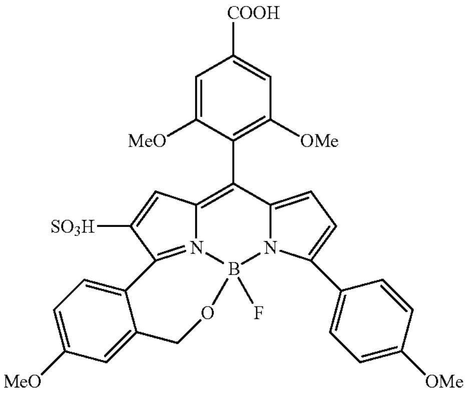
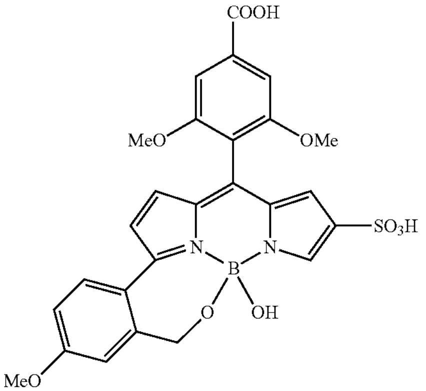
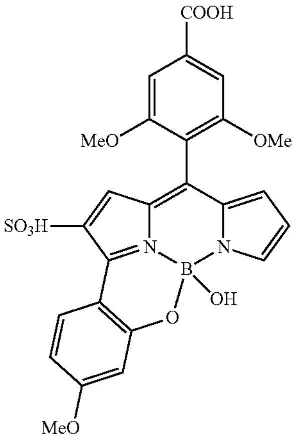
-continued
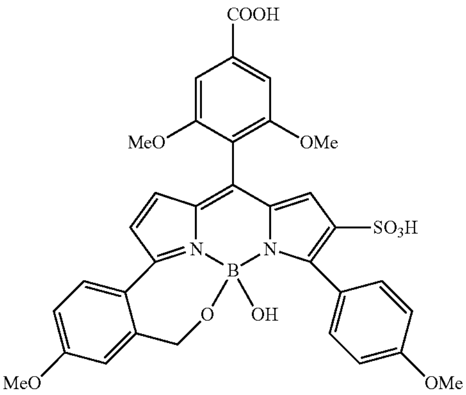
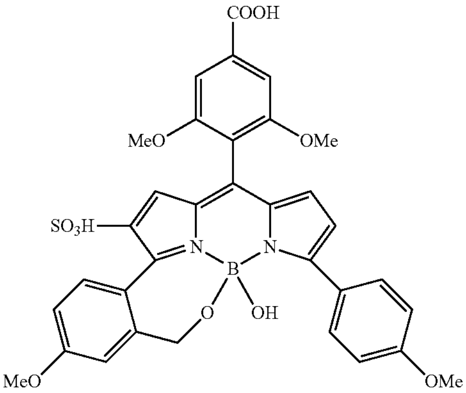
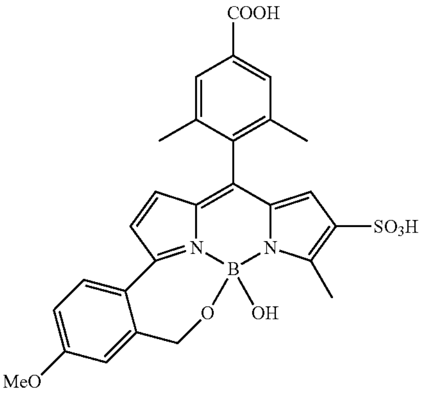
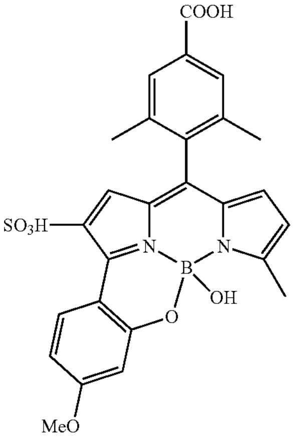

-continued
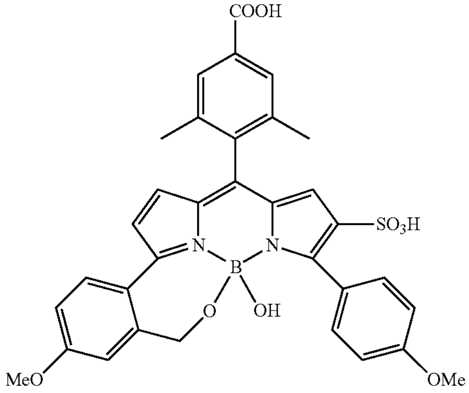
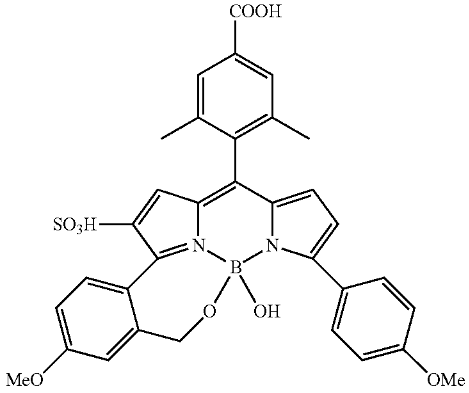
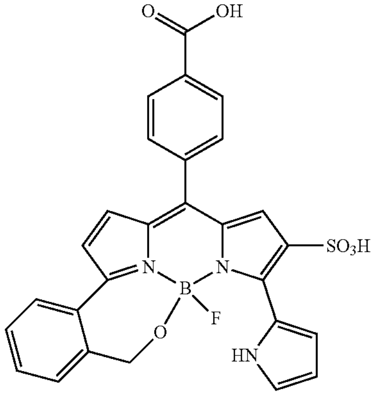
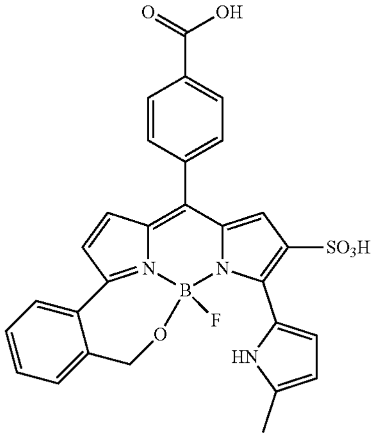
-continued
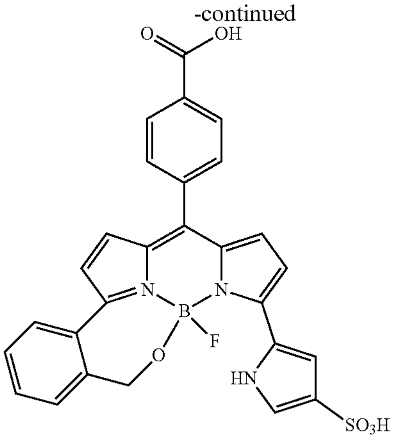
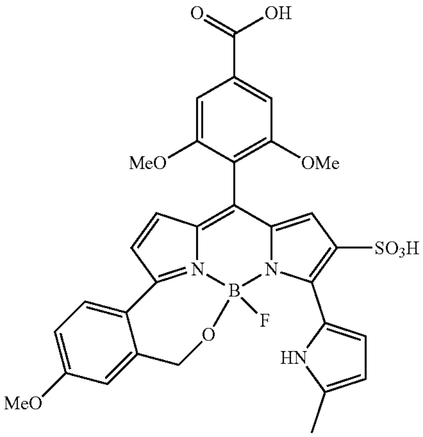
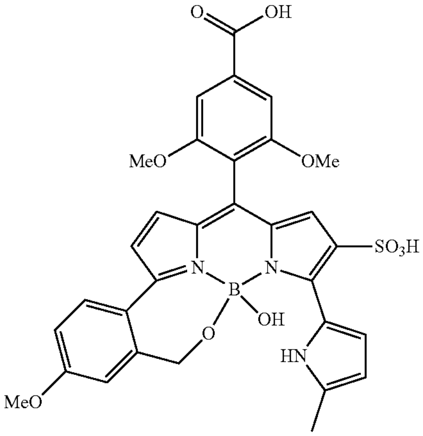
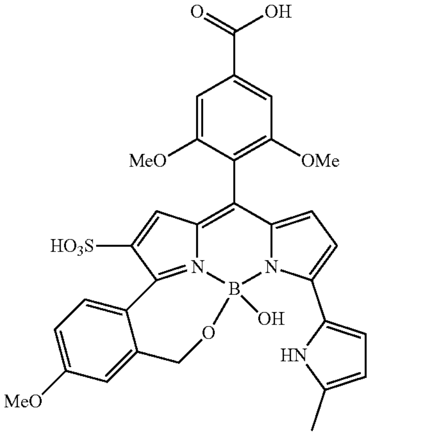

-continued
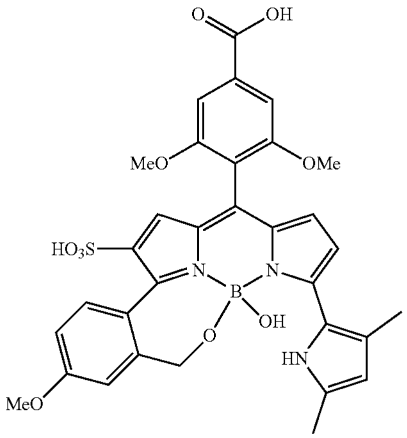
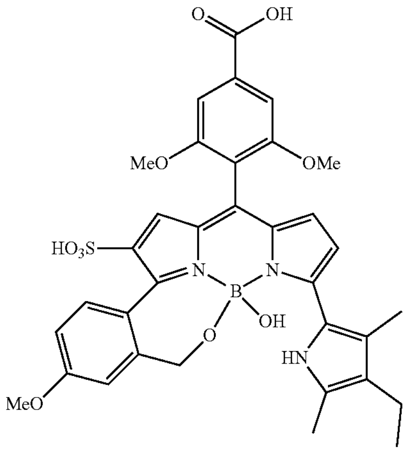
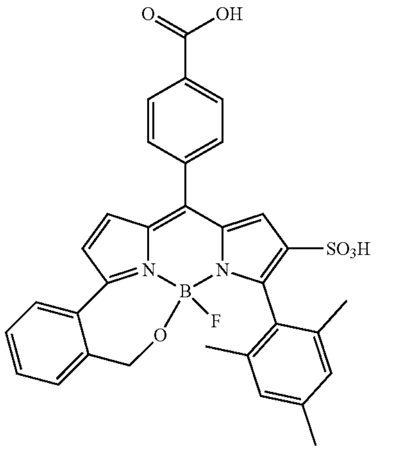
-continued
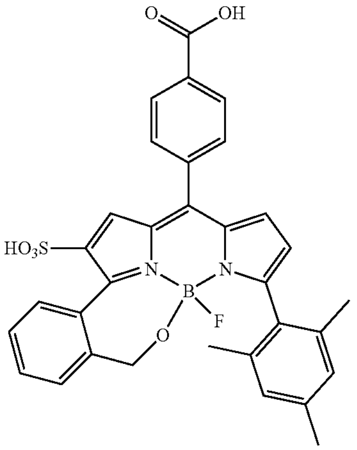
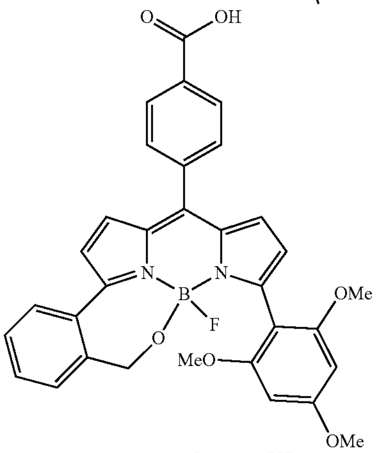
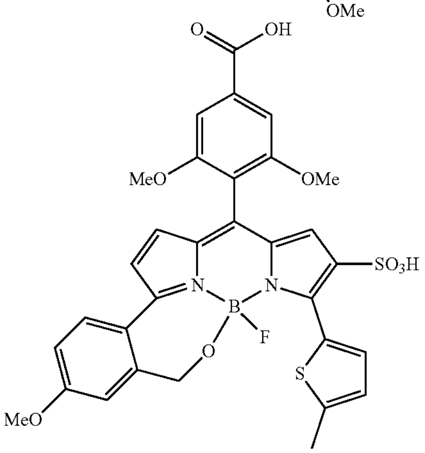
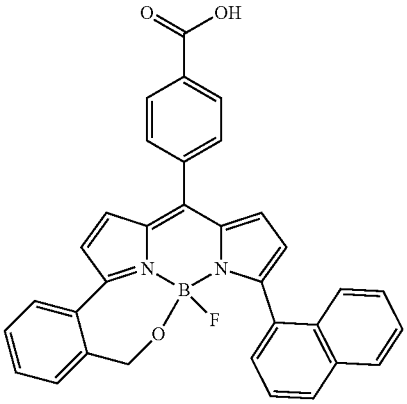

-continued
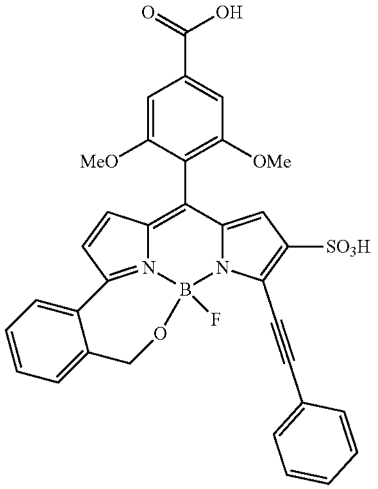
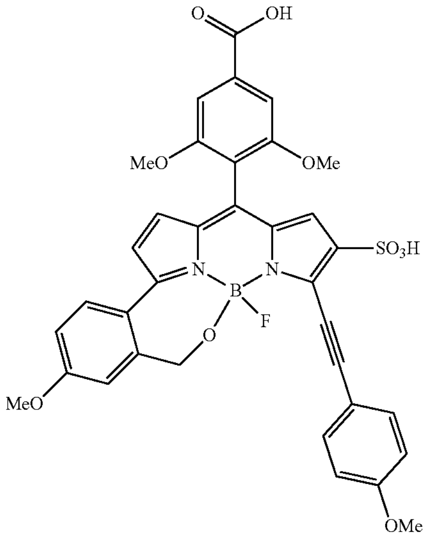
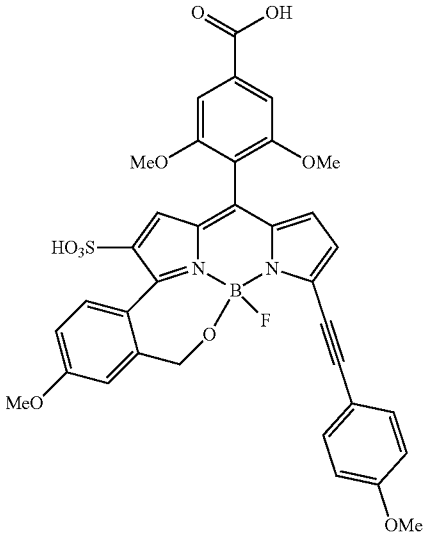
-continued
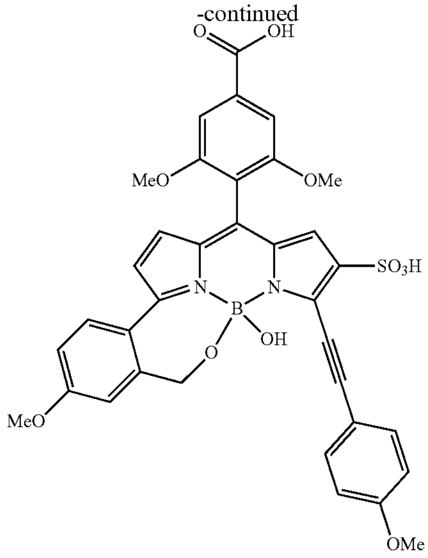
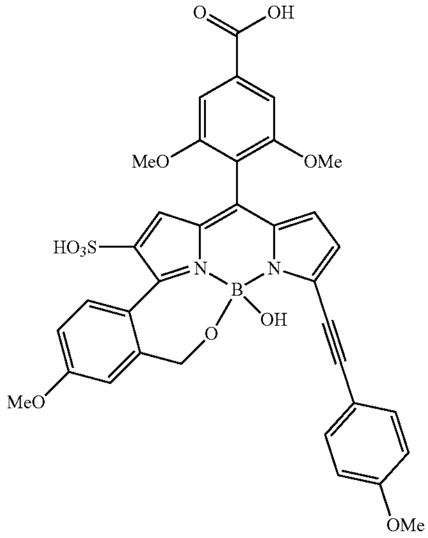
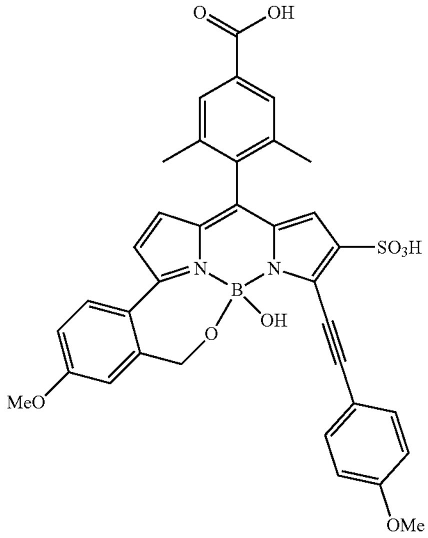

-continued
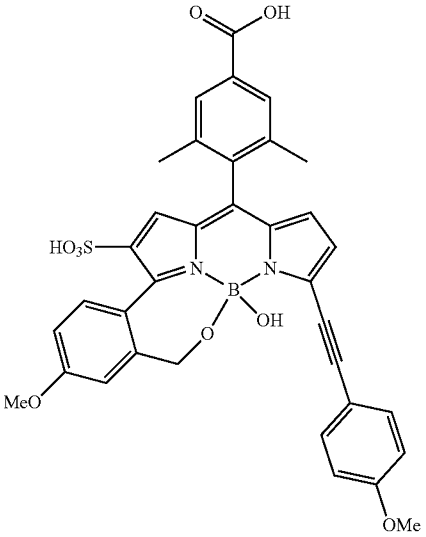
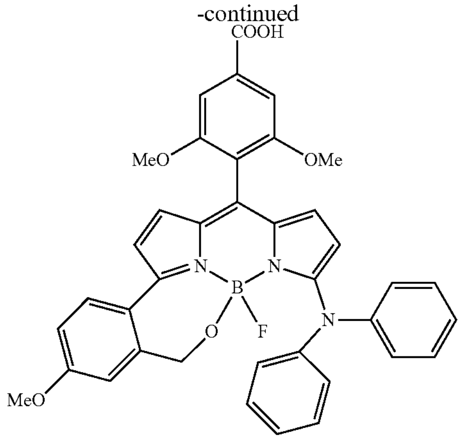
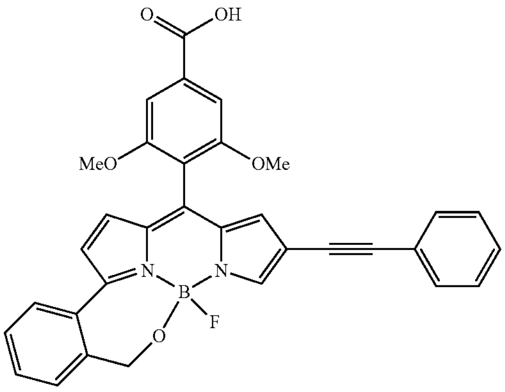
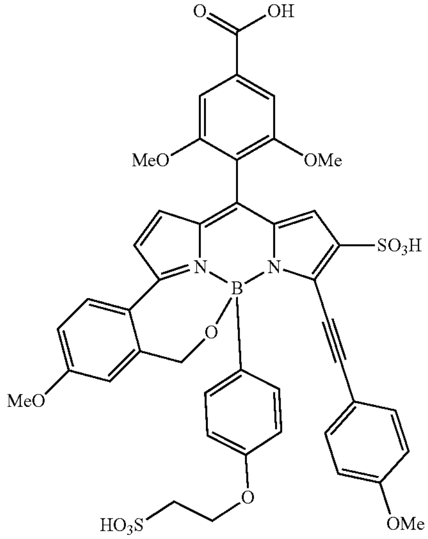
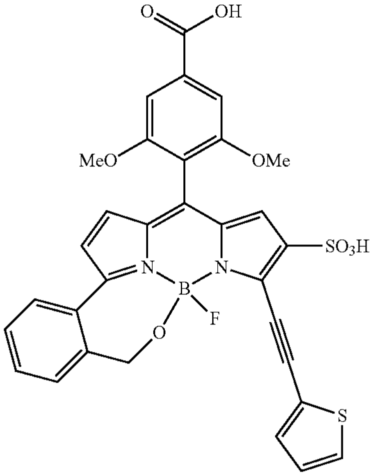
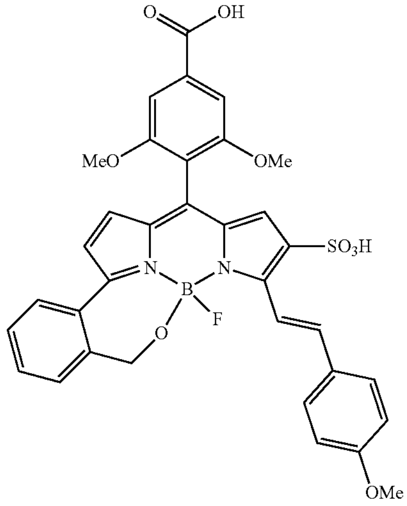

-continued
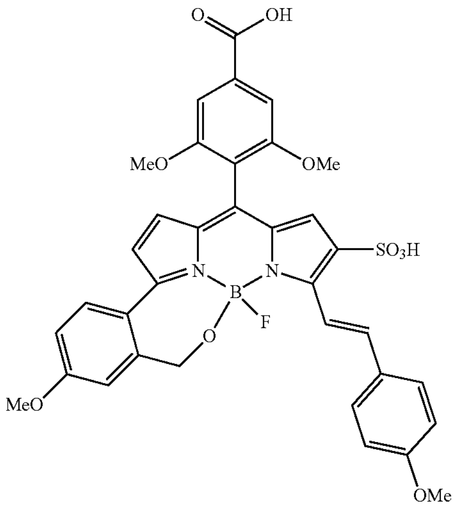
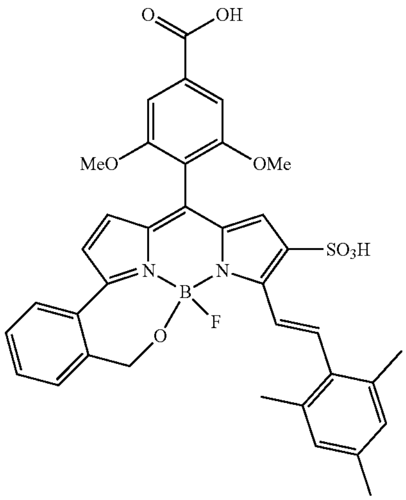
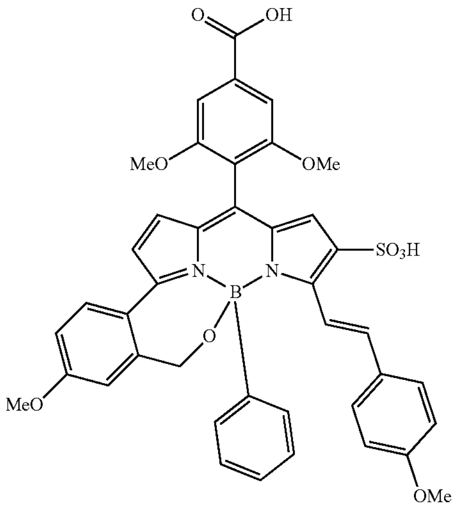
-continued
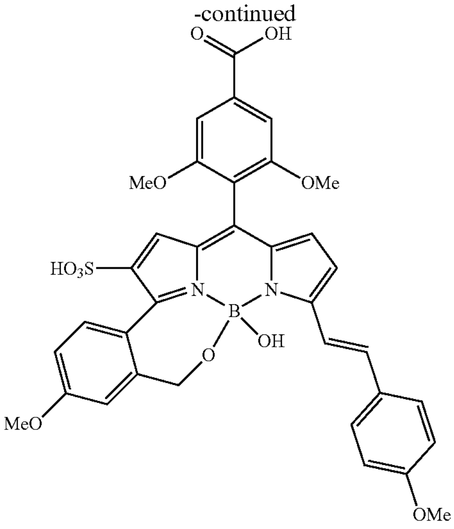
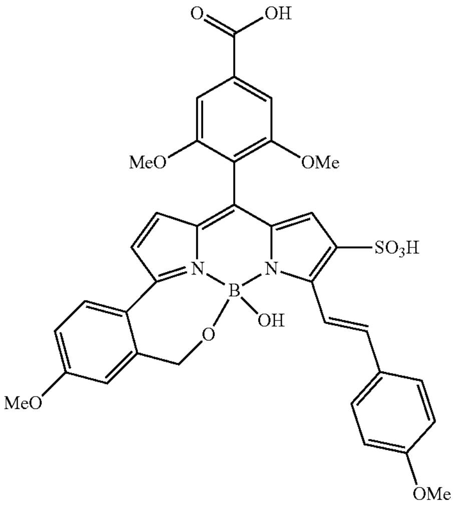
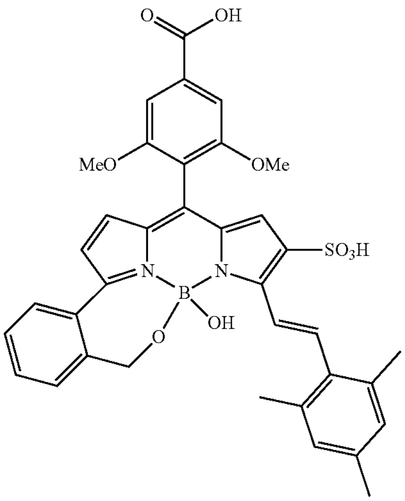

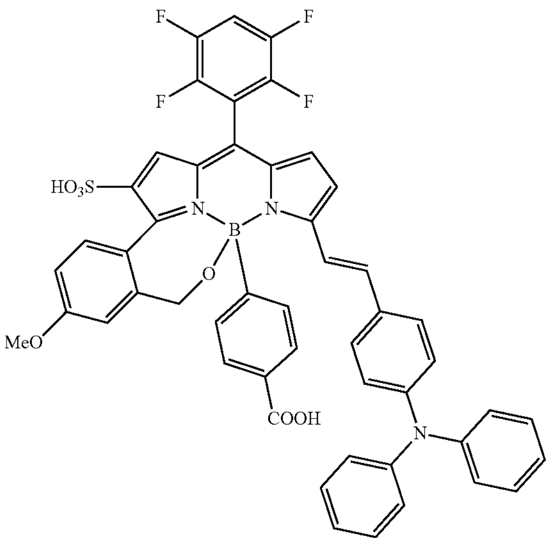
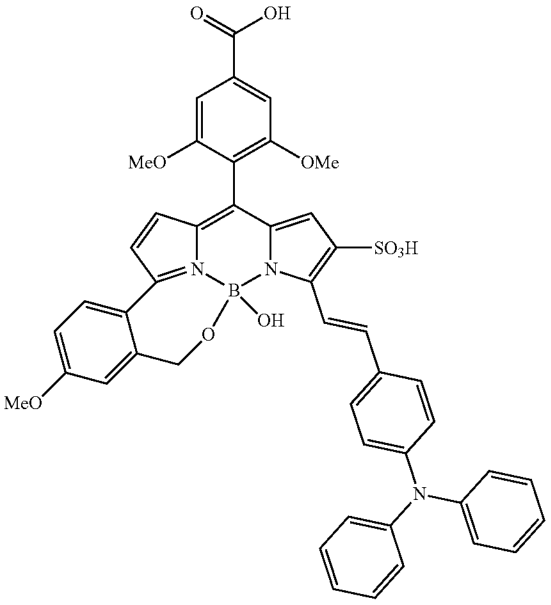
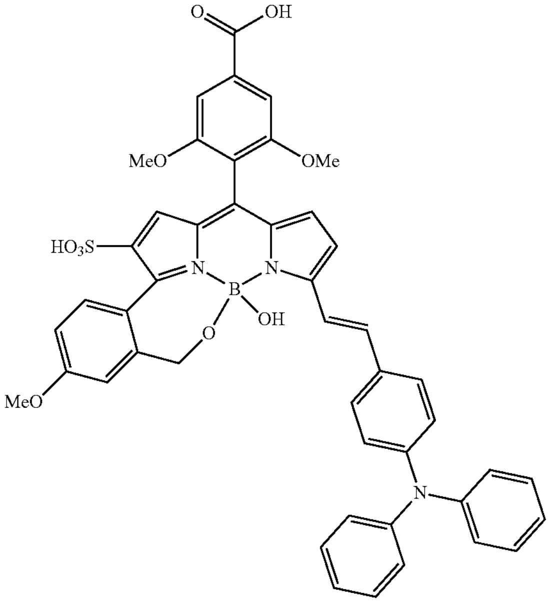
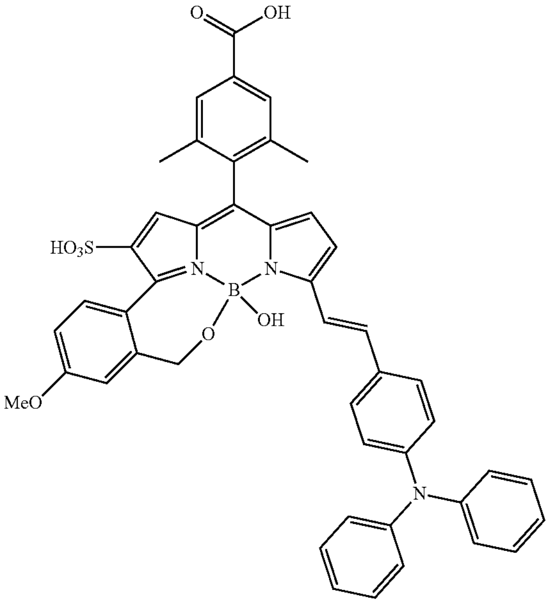

-continued
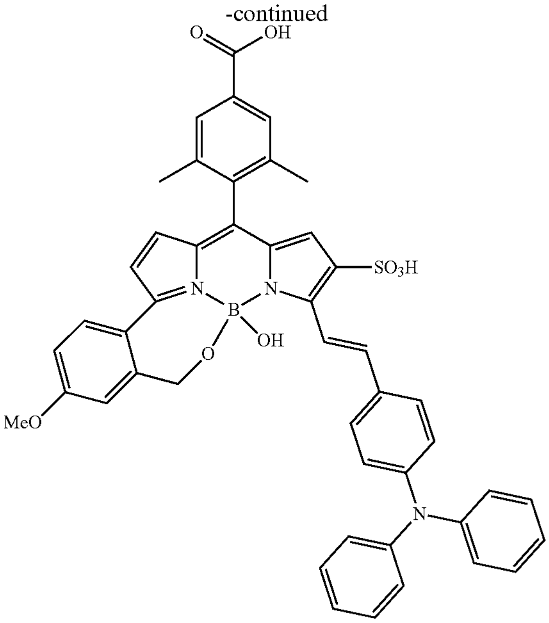
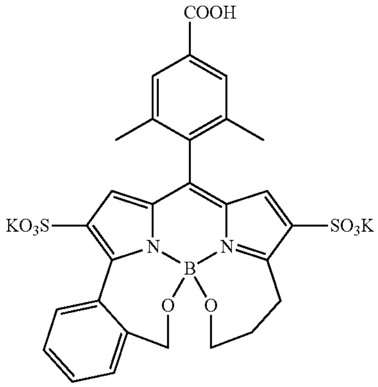
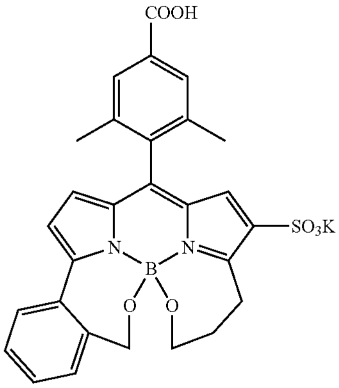
-continued
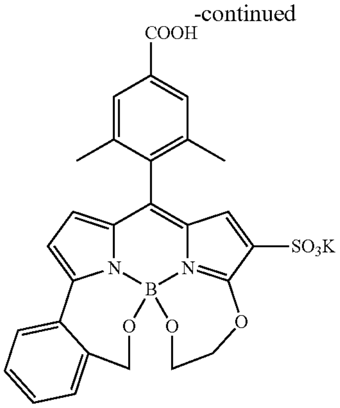
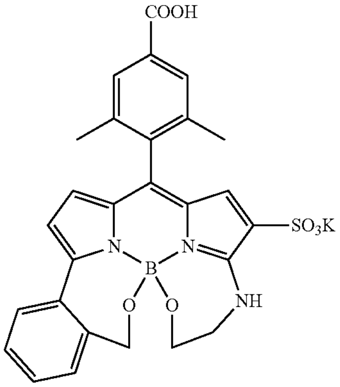
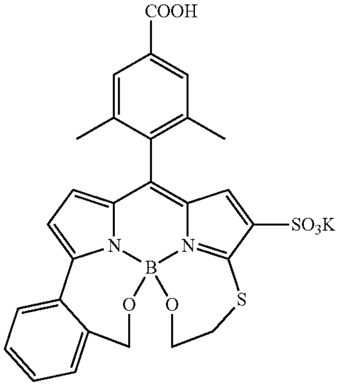
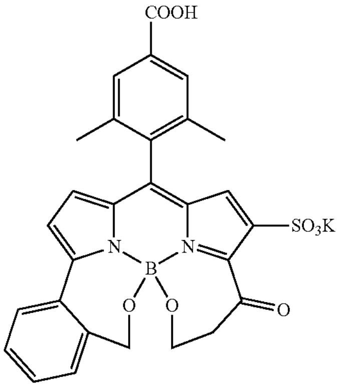

-continued
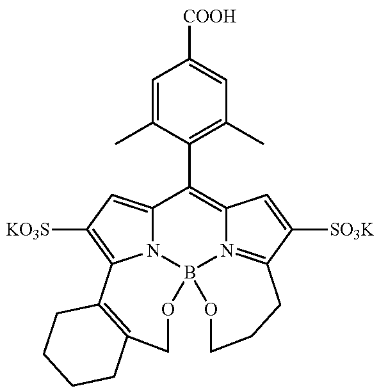
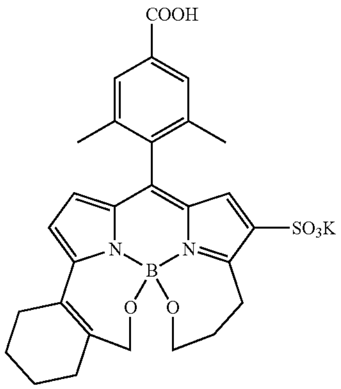
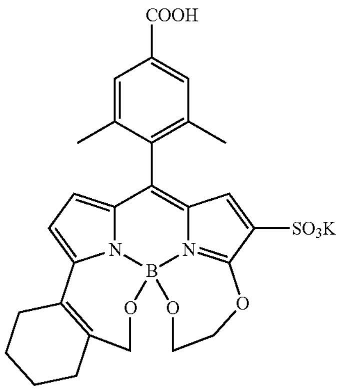
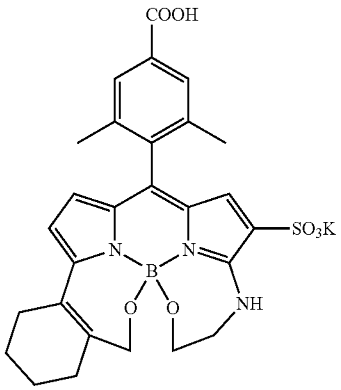
-continued
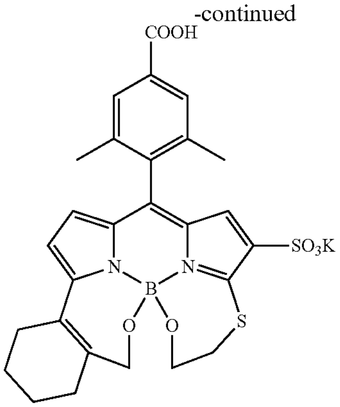
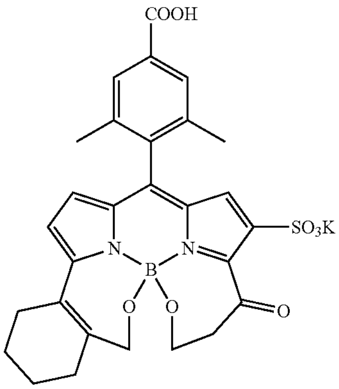
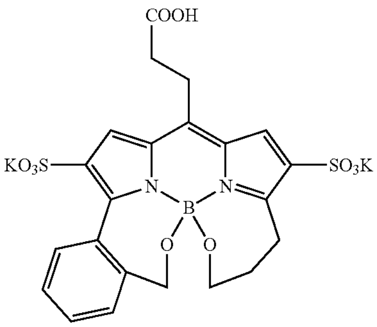
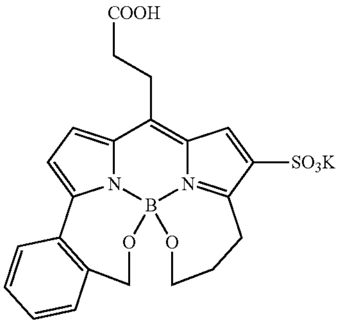

-continued

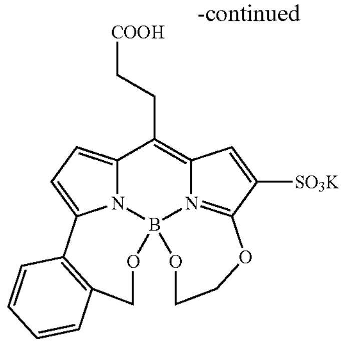

Among these specific examples of the fluorescent compound represented by Formula (1) or (4), compounds having a combination of groups which are explained as a preferred group for the $R^1$ to $R^7$, $L^1$, $L^2$, $Q^1$, $Q^2$, ring $\beta_1$, ring $\beta_2$, $L^3$ and $R^{111}$ are preferred. For example, compounds (1) to (24) described in Examples are preferable.

The fluorescent compound according to the embodiment of the present invention, which is represented by Formula (1) or Formula (4), can be synthesized by a known method. Examples of the known method include methods described in, J. Org. Chem., 2008, 73(5), 1963-1970, and J. Mater. Chem. B, 2014, 2, 1576 to 1583.

The fluorescent compound according to the embodiment of the present invention, which is represented by Formula (1) or Formula (4), has excellent hydrophilicity and thus can be used as a reagent for in vivo fluorescence imaging by being bonded to a biological substance such as a protein, a peptide, an amino acid, a nucleic acid, a sugar chain, and a lipid.

Furthermore, the fluorescent compound according to the embodiment of the present invention, which is represented by Formula (1) or Formula (4), has excellent light resistance even in a water-soluble solvent containing water (the water-soluble solvent is a solvent containing a relatively large number of oxygens). As a result, as compared with the case of using the conventional fluorescent compound, it is possible to observe a living body with high resolution for a long time.

That is, the fluorescent compound according to the embodiment of the present invention, which is represented by Formula (1) or Formula (4), includes a compound having a group capable of interacting (for example, physical adsorption and chemical bond) with a biological substance, and such a configuration is particularly preferable from the viewpoint of applying the fluorescent compound according to the embodiment of the present invention to in vivo fluorescence imaging.

Specifically, in the fluorescent compound according to the embodiment of the present invention, at least one of $R^1$ to $R^8$, $L^1$, $L^2$, $L^{11}$ to $L^{13}$, Q, $Q^1$, or $Q^2$ (in the fluorescent compound represented by Formula (1) or Formula (4), at least one of $R^1$ to $R^7$, $L^1$, $L^2$, $Q^1$, or $Q^2$) is preferably has a moiety bondable to a biological substance, and examples of the moiety bondable to a biological substance include the moiety described in the following <<Fluorescent labeled biological substance>>.

Specific examples of the compound having a group capable of interacting with a biological substance are shown below, but the present invention is not limited to these compounds. In the following specific examples, a group having a dissociative hydrogen atom such as a specific hydrophilic group Pi may adopt a salt structure by dissociating the dissociative hydrogen atom. In addition, m in the structural formula is an average number of repetitions and represents 0 to 10,000.

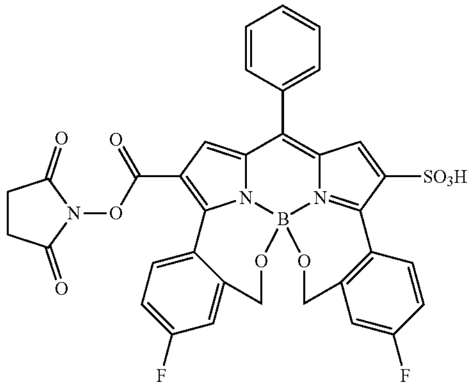

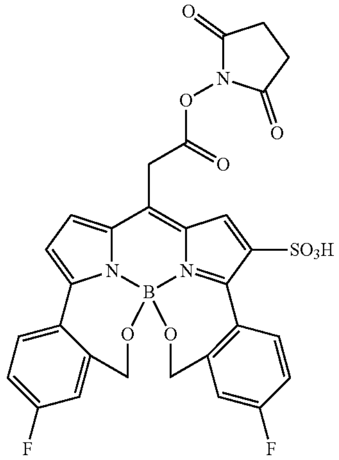

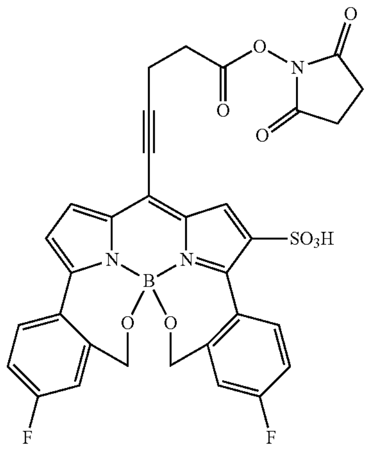

-continued
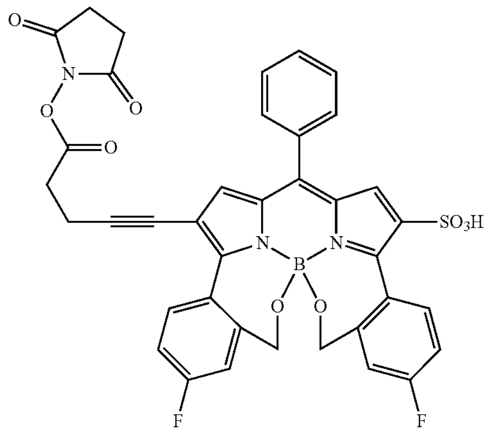
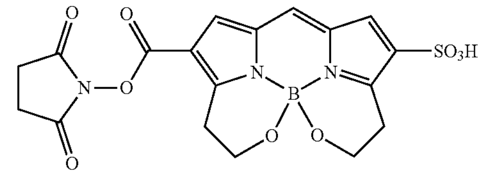
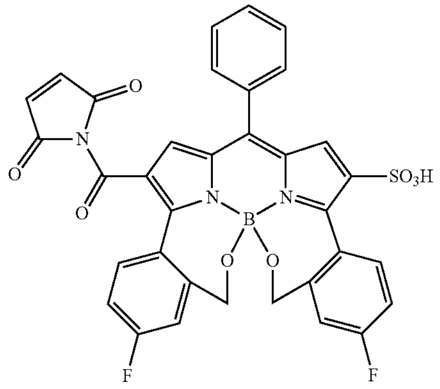
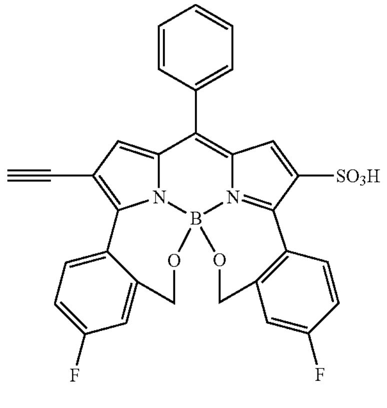
-continued
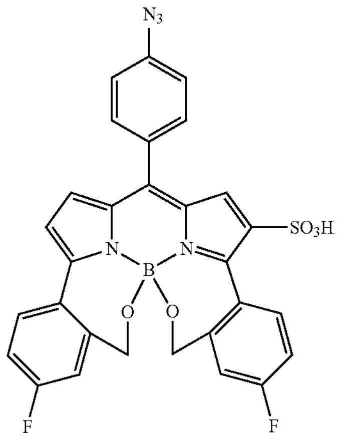
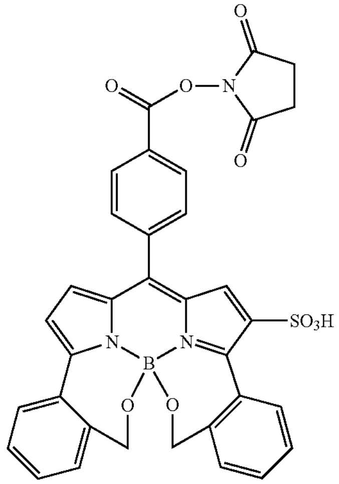
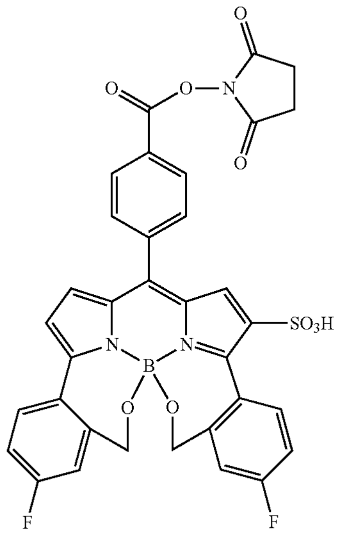

-continued
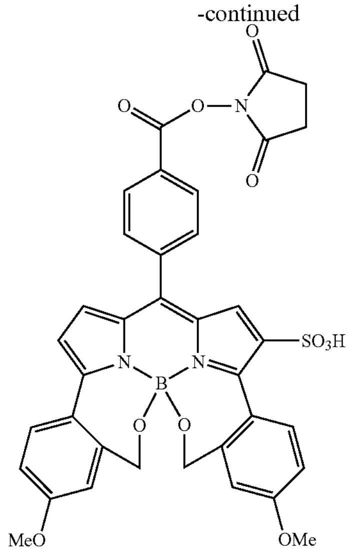
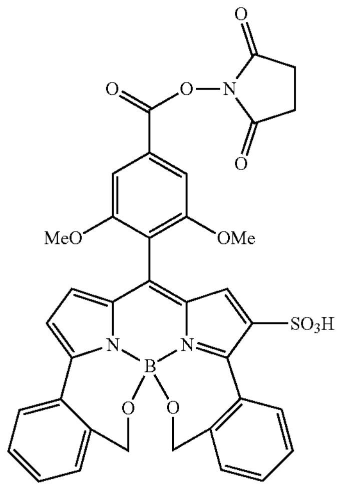
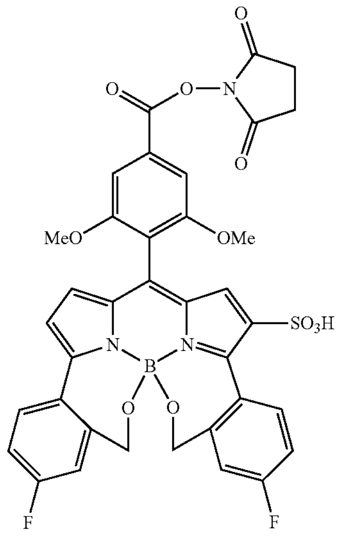
-continued
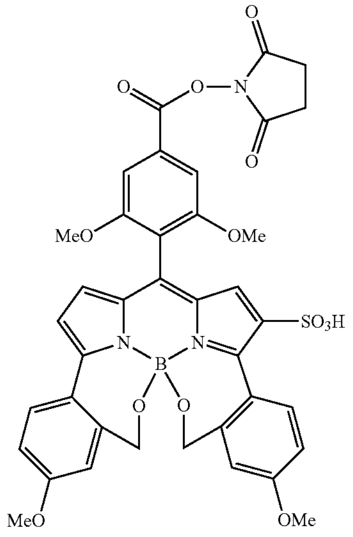
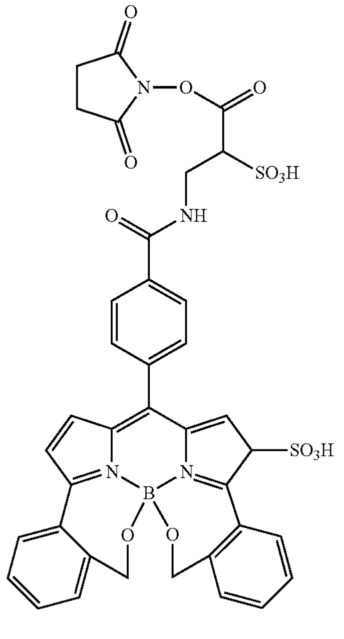
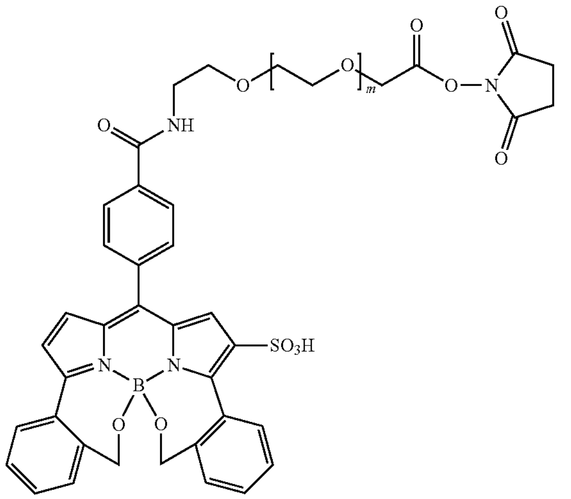

-continued

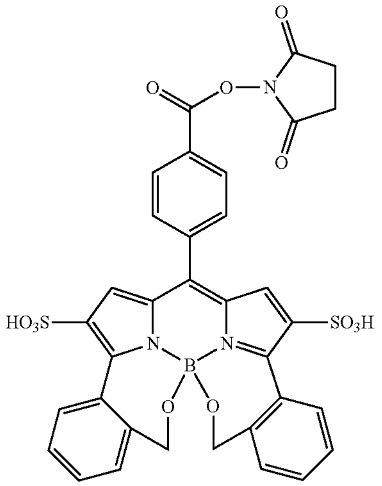

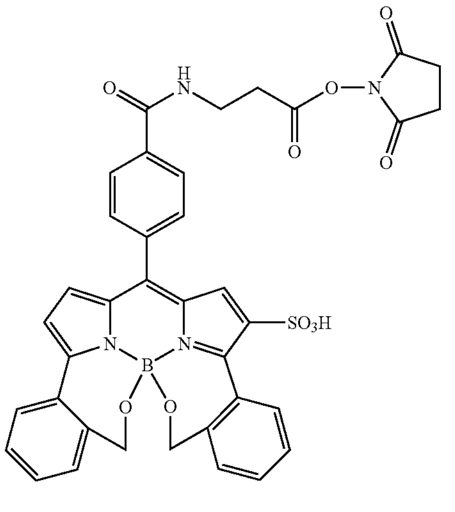

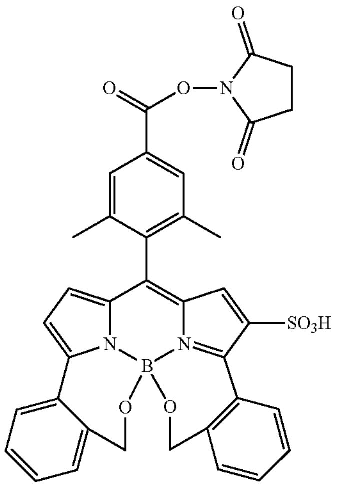

-continued

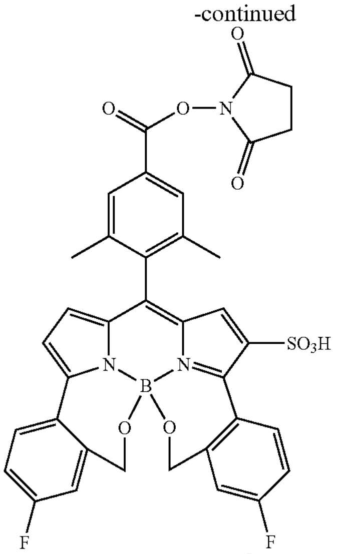

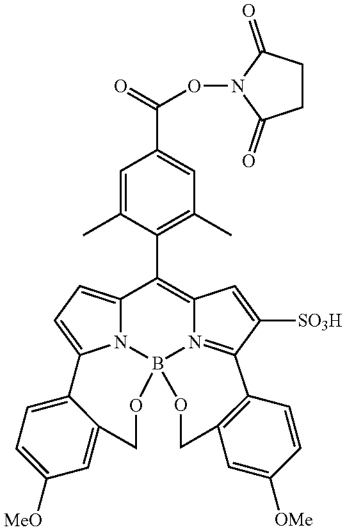

A compound having a group for acting (including adhesion) or bonding to a biological substance can be synthesized by a known method. For example, Bioconjugate Techniques (Third Edition, written by Greg T. Hermanson) can be referred to.

<<Fluorescent Labeled Biological Substance>>

The fluorescent labeled biological substance according to the embodiment of the present invention is a substance in which the fluorescent compound according to the embodiment of the present invention, which is represented by Formula (1) or Formula (4), is bonded to a biological substance. The bond between the fluorescent compound represented by Formula (1) or (4) and a biological substance may have a configuration in which the fluorescent compound represented by Formula (1) or (4) and the biological substance are directly bonded or a configuration of being linked via a linking group.

As the biological substance, a protein, a peptide, an amino acid, a nucleic acid, a sugar chain, and a lipid are preferably mentioned. As the protein, an antibody is preferably mentioned; as the lipid, a phospholipid is preferably mentioned; and as the lipid, fatty acid and sterol are preferably mentioned.

Among the above biological substances, the clinically useful substance is not particularly limited, but examples thereof include: immunoglobulins such as IgG, IgM, IgE, IgA, and IgD; plasma proteins such as complement, CRP, ferritin, $\alpha_1$ microglobulin, $\beta_2$ microglobulin, and antibodies thereof; tumor markers such as α-fetoprotein, carcinoembryonic antigen (CEA), prostate acid phosphatase (PAP), CA19-9, and CA-125, and antibodies thereof, hormones such as luteinizing hormone (LH), follicle-stimulating hormone (FSH), human ciliated gonadotrobin (hCG), estrogen, and insulin, and antibodies thereof, and infection-related substances of viruses such HIV and ATL, HBV-related antigens (HBs, HBe, and HBc), and antibodies thereof.

The examples thereof further include: bacteria such as *Corynebacterium diphteriae, Clostridium botulinum, mycoplasma*, and *Treponema pallidum*, and antibodies thereof, protozoa such as *Toxoplasma, Trichomonas, Leishmania, Trypanosoma*, and malaria parasites, and antibodies thereof, ES cells such as ELM3, HMI, KH2, v6.5, v17.2, v26.2 (derived from mice, 129, 129/SV, C57BL/6, and BALB/c), and antibodies thereof, antiepileptic drugs such as phenytoin and phenobarbital; cardiovascular drugs such as quinidine and digoxin; anti-asthma drugs such as theophylline; drugs such as antibiotics such as chloramphenicol and gentamicin, and antibodies thereof; and enzymes, extracellular toxins (for example, styrelidine O), and the like, and antibodies thereof. In addition, antibody fragments such as Fab'2, Fab, and Fv can also be used.

Examples of the specific configuration in which the fluorescent compound according to the embodiment of the present invention, which is represented by Formula (1) or Formula (4), (hereinafter, also abbreviated as the fluorescent compound (1) or (4)) and the biological substance interact with each other to be bonded include the configurations described below, i) Non-covalent bond (for example, hydrogen bond, ionic bond including chelate formation) or covalent bond between a peptide in the fluorescent compound (1) or (4) and a peptide in the biological substance, ii) Van der Waals force between a long-chain alkyl group in the fluorescent compound (1) or (4) and a lipid bilayer, a lipid, or the like in the biological substance, iii) an amide bond formed by reacting an N-hydroxysuccinimide ester (NHS ester) in the fluorescent compound (1) or (4) with an amino group in the biological substance, iv) a thioether bond formed by reacting a maleimide group in the fluorescent compound (1) or (4) with a sulfanyl group (—SH) in the biological substance, and v) a formation of a triazole ring, which is formed by Click reaction between an azido group in the fluorescent compound (1) or (4) and an acetylene group in the biological substance, or Click reaction between an acetylene group in the fluorescent compound (1) or (4) and an azido group in the biological substance.

However, as regulated in Formula (1) or Formula (4), the long-chain alkyl group in the fluorescent compound (1) or (4) described in the ii) does not include a linear alkyl group having 18 or more carbon atoms on the aryl group, in a case where X is $CR^5$, where $R^5$ is a group represented by Formula (A), $L^3$ is a single bond, and $R^{111}$ is an aryl group.

In addition to the configurations of the i) to v), the bond can be formed according to another configuration, for example, which is described in "Lucas C. D. de Rezende and Flavio da Silva Emery, A Review of the Synthetic Strategies for the Development of BODIPY Dyes for Conjugation with Proteins, Orbital: The Electronic Journal of Chemistry, 2013, Vol 5, No. 1, p. 62-83". Further, the method described in the same document can be appropriately referred to for the production of the fluorescent labeled biological substance according to the embodiment of the present invention.

| Reactive group in fluorescent compound | Example of fluorescent compound |
|---|---|
| NHS ester | 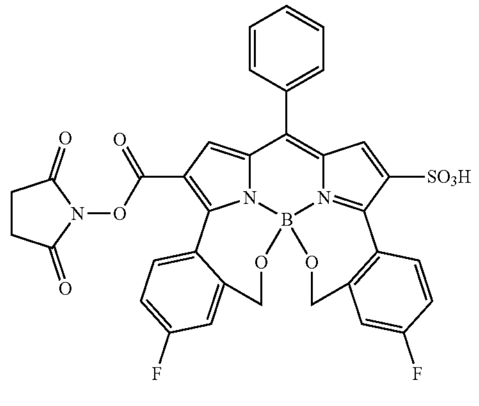 |

-continued
Malcimide
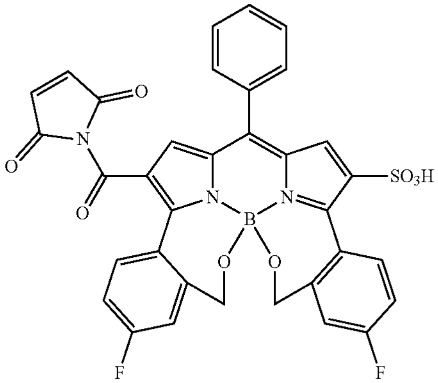
Azide
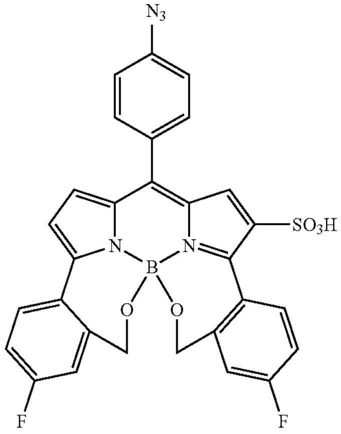
Acetylene
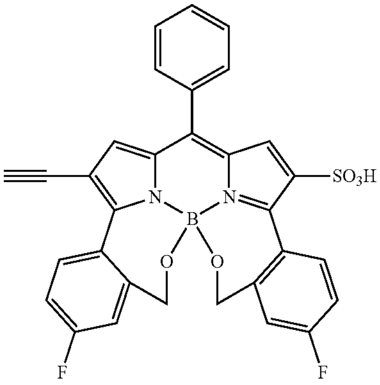
Peptide
(polyamino acid)
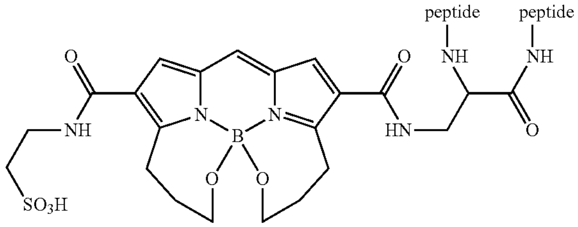

-continued
| | |
|---|---|
| Long chain alkyl | 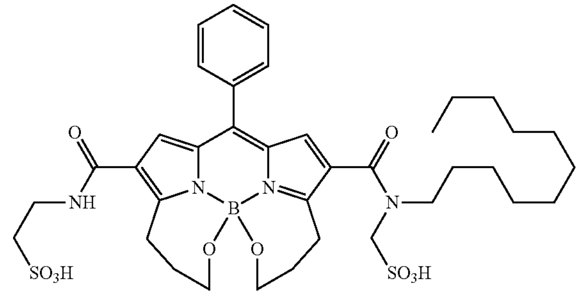 |
| Reactive group in biological substance | Product (bonding mode) |
|---|---|
| Amino group (antibody, etc.) | 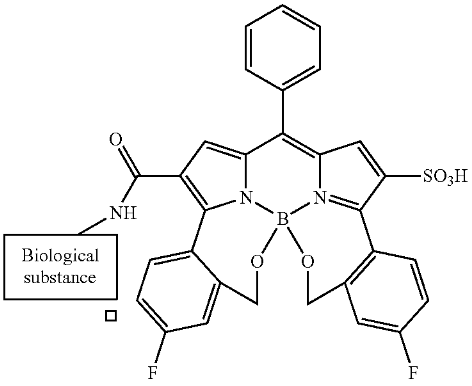 |
| Sulfanyl group (antibody, etc.) | 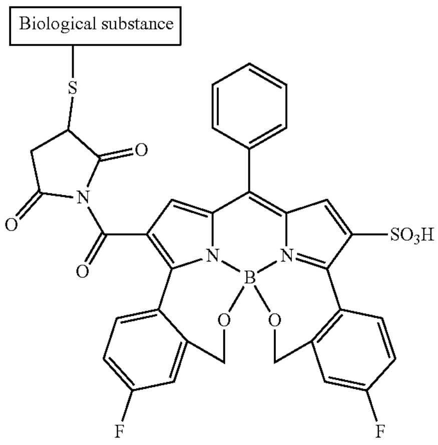 |

-continued

| | |
|---|---|
| Acetylene group (Click reaction) | 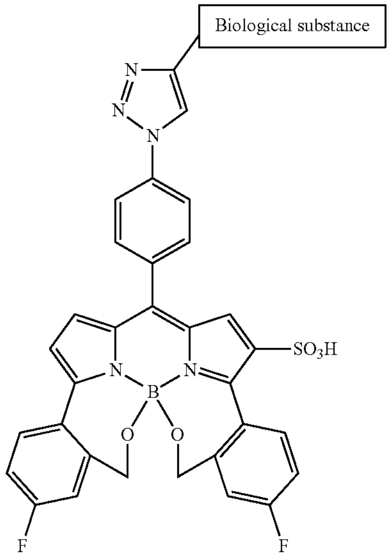 |
| Azide group (Click reaction) | 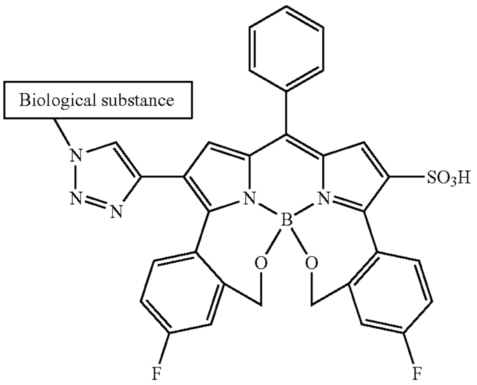 |
| Peptide bonding portion (antibody and others) | 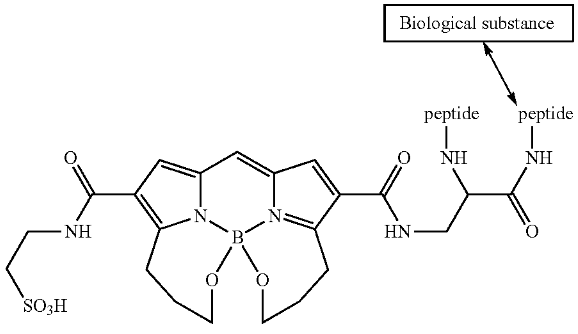 |
| Lipid bilayer Phospholipid, etc. | Van der Waals force |

The fluorescent labeled biological substance according to the embodiment of the present invention has excellent hydrophilicity and has excellent light resistance even in a water-soluble solvent containing water (the water-soluble solvent is a solvent containing a relatively large number of oxygens). As a result, as compared with the case of using the conventional fluorescent labeled biological substance having a dipyrromethene boron complex structure, such as a BODIPY (registered trademark) compound, it is possible to observe a living body with high resolution for a long time. Further, since the fluorescent labeled biological substance according to the embodiment of the present invention has excellent light resistance in a case of having a solution form dissolved in an aqueous medium such as physiological saline and a phosphate buffer solution, it also has excellent storage stability as the solution form.

<Reagent Containing Fluorescent Labeled Biological Substance>

In the reagent containing the fluorescent labeled biological substance according to the embodiment of the present invention, the form of the fluorescent labeled biological substance according to the embodiment of the present invention, for example, a solution form dissolved in an aqueous medium such as physiological saline and a phosphate buffer solution, and a solid form such as a fine particle powder or a lyophilized powder, is not particularly limited and can be appropriately selected depending on the purpose of use and the like.

For example, in a case where the fluorescent labeled biological substance according to the embodiment of the present invention is used as a reagent for in vivo fluorescence imaging, it can be used as a reagent containing the fluorescent labeled biological substance having any one of the forms described above.

<Application of Fluorescent Labeled Biological Substance>

The fluorescent labeled biological substance according to the embodiment of the present invention, obtained from the fluorescent compound according to the embodiment of the present invention, which is represented by Formula (1) or Formula (4), can stably detect fluorescence emitted from the fluorescent compound excited by light irradiation. Furthermore, it has sufficient hydrophilicity as a reagent for in vivo fluorescence imaging. Accordingly, the fluorescent labeled biological substance according to the embodiment of the present invention is suitable as, for example, a reagent for in vivo fluorescence imaging.

Cells stained by using the fluorescent labeled biological substance according to the embodiment of the present invention as a fluorescent dye can maintain the fluorescence intensity for a long time since the discoloring is highly inhibited. Accordingly, the fluorescent labeled biological substance according to the embodiment of the present invention can be suitably used in vivo fluorescence imaging which requires excellent light resistance, for example, a long-term observation of a biological substance such as the microscopic observation by time-lapse measurement, and an observation of a biological substance using high-resolution microscopes such as the confocal laser microscope and the super-resolution microscope such as the stimulated emission depletion microscope (STED microscope).

In vivo fluorescence imaging using the fluorescent labeled biological substance according to the embodiment of the present invention includes the following processes of (i) to (iii).

(i) A process of preparing a targeted biological substance (hereinafter, referred to as "target biological substance") and a fluorescent labeled biological substance according to the embodiment of the present invention in which a biological substance capable of bonding to the target biological substance is bonded to the fluorescent compound according to the embodiment of the present invention (ii) A process of bonding the target biological substance to the fluorescent labeled biological substance according to the embodiment of the present invention (iii) A process of irradiating a substance obtained by bonding the fluorescent labeled living body according to the embodiment of the present invention to the target biological substance with light having a range of the wavelength which is absorbed by the fluorescent labeled living body according to the embodiment of the present invention, and detecting the fluorescence emitted by the fluorescent labeled biological substance according to the embodiment of the present invention In the in vivo fluorescence imaging described above, examples of the biological substance capable of bonding to the target biological substance include the above-described biological substance in the fluorescent labeled biological substance according to the embodiment of the present invention. The biological substance can be appropriately selected depending on the target biological substance (test object), and a biological substance capable of specifically binding to the test object can be selected.

Examples of the target biological substance include a protein, which is a so-called disease marker. The disease marker is not particularly limited, and examples thereof include α-fetoprotein (AFP), PIVKA-II, BCA225, basic fetoprotein (BFP), CA15-3, CA19-9, CA72-4, CA125, CA130, CA602, CA54/61 (CA546), carcinoembryonic antigen (CEA), DUPAN-2, elastase 1, immunosuppressive acidic protein (IAP), NCC-ST-439, γ-seminoprotein (γ-Sm)), prostate specific antigen (PSA), prostatic acid phosphatase (PAP), nerve specific enolase (NSE), Ibai amyloid β, tau, squamous cell carcinoma associated antigen (SCC antigen), sialyl LeX-i antigen (SLX), SPan-1, tissue polypeptide antigen (TPA), sialyl Tn antigen (STN), cytokeratin (CYFRA) pepsinogen (PG), C-reactive protein (CRP), serum amyloid A protein (SAA), myoglobin, creatine kinase (CK), troponin T, and ventricular muscle myosin light chain I.

Examples of the bacterium among the above-described target biological substances include a bacterium to be subjected to a cellular and microbiological test, which are not particularly limited. Specific examples thereof include *Escherichia coli, Salmonella, Legionella*, and bacteria causing problems in public health.

The virus antigen among the above-described target biological substances is not particularly limited, and examples thereof include hepatitis virus antigens such as hepatitis C and B virus antigens, p24 protein antigen of HIV virus, and pp65 protein antigen of cytomegalovirus (CMV), and E6 and E7 proteins of papillomavirus (HPV).

In the above (i), the target biological substance is not particularly limited and can be prepared according to a conventional method.

In addition, the fluorescent labeled biological substance according to the embodiment of the present invention is not particularly limited and can be prepared by bonding a biological substance capable of binding to a target biological substance to the fluorescent compound according to the embodiment of the present invention, according to a conventional method. As the configuration of the bond and the reaction for forming the bond, the configuration in which the bond is formed by interaction and the reaction which are described in <<Fluorescent labeled biological substance>> according to the embodiment of the present invention are mentioned.

In the above (ii), the fluorescent labeled biological substance according to the embodiment of the present invention may be directly bonded to the target biological substance or may be bonded via another biological substance which is different from the fluorescent labeled biological substance according to the embodiment of the present invention and the target biological substance. In vivo fluorescence imaging using the fluorescent labeled biological substance according to the embodiment of the present invention is not particularly limited, and examples thereof include fluorescent cell staining. The fluorescent cell staining includes a direct method in which a fluorescent labeled antibody is used as a primary antibody and an indirect method in which a primary antibody is reacted with a secondary antibody that is used as a fluorescent labeled antibody. The fluorescent labeled biological substance according to the embodiment of the present invention can be used as a fluorescent labeled antibody in both the direct method and the indirect method but is preferably used as a fluorescent labeled antibody in the indirect method.

The binding of the fluorescent labeled biological substance according to the embodiment of the present invention to the target biological substance is not particularly limited and can be performed according to a conventional method.

In the above (iii), the wavelength for exciting the fluorescent labeled living body according to the embodiment of the present invention is not particularly limited as long as the wavelength is an emission wavelength (exitation light) capable of exciting the fluorescent labeled living body according to the embodiment of the present invention. Generally, the wavelength for excitation is preferably 300 to 1,000 nm and more preferably 400 to 800 nm.

The fluorescence excitation light source used in the present invention is not particularly limited as long as it emits an emission wavelength (exitation light) capable of exciting the fluorescent labeled living body according to the embodiment of the present invention, and various laser light sources can be used. Examples of the laser light source include a He—Ne laser, a $CO_2$ laser, an Ar laser, a Kr laser, a He—Cd laser, an excimer laser, a gas laser such as nitrogen laser, a ruby laser, a yttrium-aluminum-garnet (YAG) laser, a solid-state laser such as glass laser, a dye laser, and a semiconductor laser. In addition, various optical filters can be used to obtain a preferred excitation wavelength or detect only fluorescence.

Other matters in the above (i) to (iii) are not particularly limited and can be appropriately selected depending on conditions such as a method, a reagent, and an apparatus, which are usually used.

In the in vivo fluorescence imaging using the fluorescent labeled living body according to the embodiment of the present invention, the discoloring of the substance obtained by bonding the fluorescent labeled living body according to the embodiment of the present invention to the target biological substance is highly inhibited, whereby a biological substance can be observed while maintaining the fluorescence intensity for a long time. Further, even in a case where a high resolution microscope or a super resolution microscope is used, observation can be performed while maintaining the fluorescence intensity.

Further, in addition to the above, the fluorescent labeled biological substance according to the embodiment of the present invention can be suitably used even in the long-term storage of stained cells, by appropriately adjusting the storage conditions.

—Substituent Group T—

In the present invention, the preferred substituents include those selected from the following substituent group T.

In addition, in the present specification, in a case where it is simply described as a substituent, the substituent refers to the substituent group T, and in a case where an individual group, for example, an alkyl group is only described, a corresponding group in the substituent group T is preferably applied.

Further, in the present specification, in a case where an alkyl group is described separately from a cyclic (cyclo) alkyl group, the alkyl group is used to include a linear alkyl group and a branched alkyl group. On the other hand, in a case where an alkyl group is not described separately from a cyclic alkyl group, and unless otherwise specified, the alkyl group is used to include a linear alkyl group, a branched alkyl group, and a cycloalkyl group. This also applies to groups (alkoxy group, alkylthio group, alkenyloxy group, and the like) containing a group capable of having a cyclic structure (alkyl group, alkenyl group, alkynyl group, and the like) and compounds containing a group capable of having a cyclic structure. In a case where a group is capable of forming a cyclic skeleton, the lower limit of the number of atoms of the group forming the cyclic skeleton is 3 or more and preferably 5 or more, regardless of the lower limit of the number of atoms specifically described below for the group that can adopt this structure, In the following description of the substituent group T, a group having a linear or branched structure and a group having a cyclic structure, such as an alkyl group and a cycloalkyl group, are sometimes described separately for clarity.

The groups included in the substituent group T include the following groups:

an alkyl group (preferably having 1 to 30 carbon atoms, more preferably 1 to 20 carbon atoms, still more preferably 1 to 12 carbon atoms, still more preferably 1 to 8 carbon atoms, still more preferably 1 to 6 carbon atoms, and particularly preferably 1 to 3 carbon atoms); an alkenyl group (preferably having 2 to 30 carbon atoms, more preferably 2 to 20 carbon atoms, still more preferably 2 to 12 carbon atoms, still more preferably 2 to 6 carbon atoms, and even still more preferably 2 to 4 carbon atoms); an alkynyl group (preferably having 2 to 30 carbon atoms, still more preferably 2 to 20 carbon atoms, still more preferably 2 to 12 carbon atoms, still more preferably 2 to 6 carbon atoms, and even still more preferably 2 to 4 carbon atoms); a cycloalkyl group (preferably having 3 to 20 carbon atoms); a cycloalkenyl group (preferably having 5 to 20 carbon atoms); an aryl group (The aryl group may be a monocyclic group or a condensed ring group (preferably a group in which 2 to 6 rings are condensed). In a case of a condensed ring group, the condensed ring group consists of a 5- to 7-membered ring or the like. The aryl group preferably has 6 to 40 carbon atoms, more preferably 6 to 30 carbon atoms, still more preferably 6 to 26 carbon atoms, and particularly preferably 6 to 10 carbon atoms.); a heterocycle group (The heterocycle group has at least one nitrogen atom, an oxygen atom, a sulfur atom, a phosphorus atom, a silicon atom, or selenium atom as a ring-constituting atom, and may be a monocyclic ring or a condensed ring (preferably a group in which 2 to 6 rings are condensed. In a case of a monocyclic group, the monocyclic ring is preferably a 5- to 7-membered ring and more preferably a 5- or 6-membered ring. The heterocycle group preferably has 2 to 40 carbon atoms and more preferably 2 to 20 carbon atoms. The heterocycle group includes an aromatic heterocycle group (heteroaryl group) and an aliphatic heterocycle group (aliphatic heterocyclic group); an alkoxy group (preferably having 1 to 20 carbon atoms and more preferably 1 to 12 carbon atoms), an alkenyloxy group (preferably having 2 to 20 carbon atoms and more preferably 2 to 12 carbon atoms); an alkynyloxy group (preferably having 2 to 20 carbon atoms and more preferably 2 to 12 carbon atoms; a cycloalkyloxy group (preferably having 3 to 20 carbon atoms); an aryloxy group (preferably having 6 to 40 carbon atoms, more preferably 6 to 26 carbon atoms, and still more preferably 6 to 14 carbon atoms; a heterocyclic oxy group (preferably having 2 to 20 carbon atoms);

an alkoxycarbonyl group (preferably having 2 to 20 carbon atoms); a cycloalkoxycarbonyl group (preferably having 4 to 20 carbon atoms); an aryloxycarbonyl group (preferably having 6 to 20 carbon atoms); an amino group (The amino group preferably has 0 to 20 carbon atoms and includes an unsubstituted amino group (—$NH_2$), a (mono- or di-)alkylamino group, a (mono- or di-)alkenylamino group, a (mono- or di-) alkynylamino group, a (mono- or di-)cycloalkylamino group, a (mono- or di-)cycloalkenylamino group, a (mono- or di-)arylamino group, and a (mono- or di-) heterocyclic amino group. Each of the above groups with which the unsubstituted amino group is substituted has the same meaning as the corresponding group of the substituent group T.); a sulfamoyl group (preferably having 0 to 20 carbon atoms, and preferably an alkyl, cycloalkyl, or aryl sulfamoyl group); an acyl group (preferably having 1 to 20 carbon atoms and more preferably 2 to 15 carbon atoms); an acyloxy group (preferably having 1 to 20 carbon atoms); a carbamoyl group (preferably having 1 to 20 carbon atoms and preferably an alkyl, cycloalkyl, or aryl carbamoyl group);

an acylamino group (preferably having 1 to 20 carbon atoms); a sulfonamide group (preferably having 0 to 20 carbon atoms and preferably an alkyl, cycloalkyl, or aryl sulfonamide group); an alkylthio group (preferably having 1 to 20 carbon atoms and more preferably 1 to 12 carbon atoms); a cycloalkylthio group (preferably having 3 to 20 carbon atoms); an arylthio group (preferably having 6 to 40 carbon atoms, more preferably 6 to 26 carbon atoms and still more preferably 6 to 14 carbon atoms); a heterocyclic thio group (preferably having 2 to 20 carbon atoms); an alkyl, cycloalkyl, or aryl sulfonyl group (preferably having 1 to 20 carbon atoms);

a silyl group (preferably having 1 to 30 carbon atoms and more preferably 1 to 20 carbon atoms, and preferably substituted with an alkyl, aryl, alkoxy, or aryloxy); a silyloxy group (preferably having 1 to 20 carbon atoms and preferably substituted with an alkyl, aryl, alkoxy, or aryloxy); a hydroxy group; a cyano group; a nitro group; a halogen atom (for example, a fluorine atom, a chlorine atom, a bromine atom or an iodine atom); an oxygen atom (specifically replacing >$CH_2$ which constitutes a ring with >C═O); a carboxy group (—$CO_2H$), a phosphono group [—$PO(OH)_2$], a phosphoryl group [—O—$PO(OH)_2$], a sulfo group (—$SO_3H$), a boric acid group [—$B(OH)_2$], an onio group (including an ammonio group including a cyclic ammonio, a sulfonio group, and a phosphonio group, and preferably having 0 to 30 carbon atoms and more preferably 1 to 20 carbon atoms); a sulfanyl group (—SH); an amino acid residue; and a polyamino acid residue.

Further, the groups included in the substituent group T include: a carboxy group; a phosphono group; a sulfo group; an onio group; an amino acid residue; and the above-described alkyl group, alkenyl group, alkynyl group, cycloalkyl group, cycloalkenyl group, aryl group, heterocycle group, alkoxy group, alkenyloxy group, alkynyloxy group, cycloalkyloxy group, aryloxy group, heterocyclic oxy group, alkoxycarbonyl group, cycloalkoxycarbonyl group, aryloxycarbonyl group, amino group, sulfamoyl group, acyl group, acyloxy group, carbamoyl group, acylamino group, sulfonamide group, alkylthio group, cycloalkylthio group, arylthio group, heterocyclic thio group, and an alkyl, cycloalkyl, or aryl sulfonyl group, which have a polyamino acid residue as a substituent.

The substituent selected from the substituent group T is more preferably an alkyl group, an alkenyl group, a cycloalkyl group, an aryl group, a heterocycle group, an alkoxy group, a cycloalkoxy group, an aryloxy group, an alkoxycarbonyl group, a cycloalkoxycarbonyl group, an amino group, an acylamino group, a cyano group or a halogen atom, and particularly preferably an alkyl group, an alkenyl group, an aryl group, a heterocycle group, an alkoxy group, an alkoxycarbonyl group, an amino group, an acylamino group, or a cyano group.

The substituent selected from the substituent group T also includes a group formed by combining a plurality of the above groups, unless otherwise specified. For example, in a case where a compound, a substituent, or the like contains an alkyl group, an alkenyl group, or the like, the alkyl group, the alkenyl group, or the like may be substituted or unsubstituted. In addition, in a case where a compound, a substituent, or the like contains an aryl group, a heterocycle group, or the like, the aryl group, the heterocycle group, or the like may be a monocyclic ring or a condensed ring, and may be substituted or unsubstituted.

EXAMPLES

Hereinafter, the present invention will be described in more detail based on Examples, but the present invention is not limited thereto.

Compounds (1) to (24) and comparative compounds (1) and (2) used in Examples and Comparative Examples are shown below. It is noted that [ ] in the structural formula of the compound (14) indicates a repeating structure.

Compound (1)

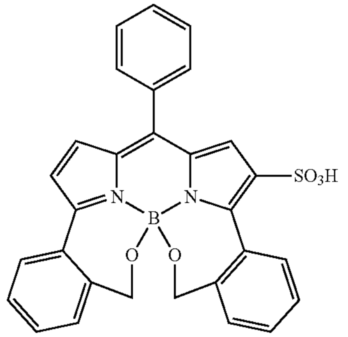

Compound (2)

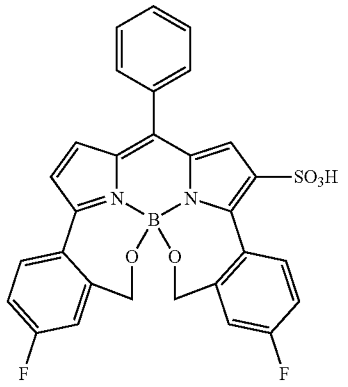

-continued
Compound (3)
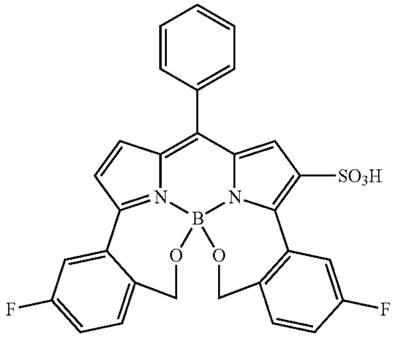
Compound (4)
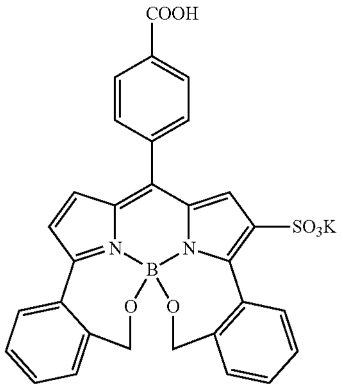
Compound (5)
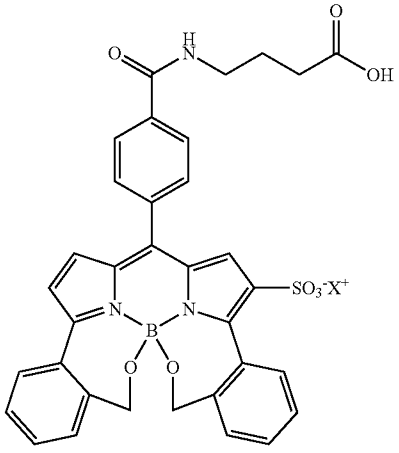
$X^+ = K^+$,
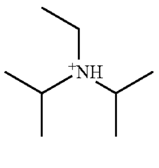
-continued
Compound (6)
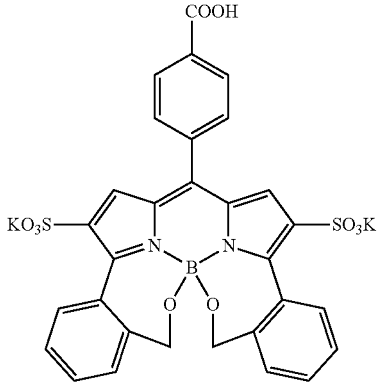
Compound (7)
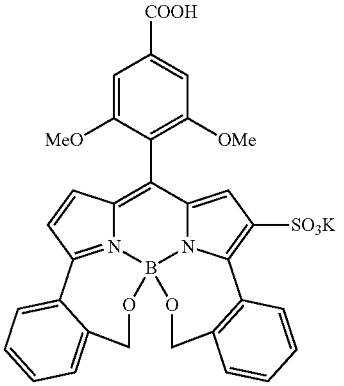
Compound (8)
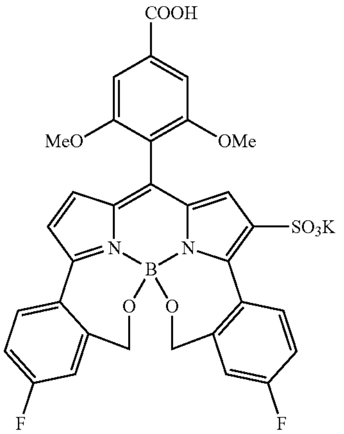
Compound (9)
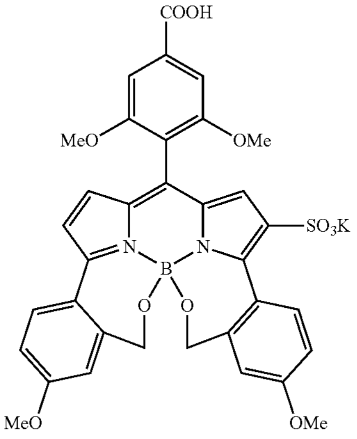

-continued
Compound (10)
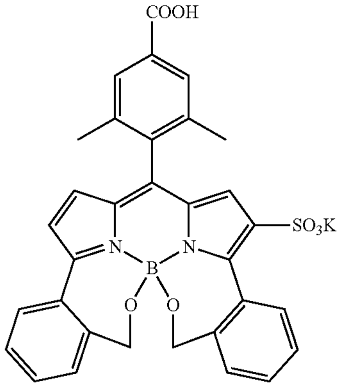
Compound (11)
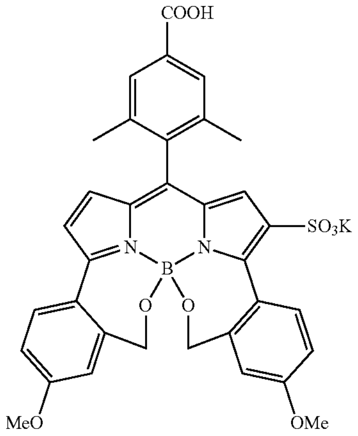
Compound (12)
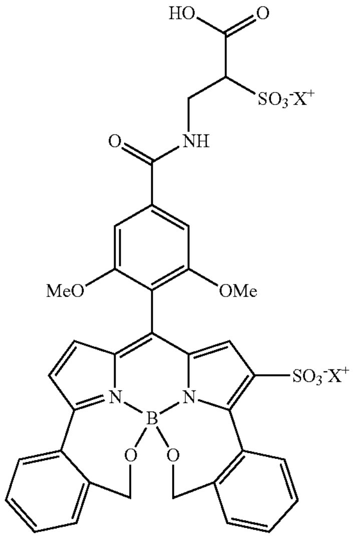
$X^+ = K^+$,
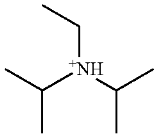
-continued
Compound (13)
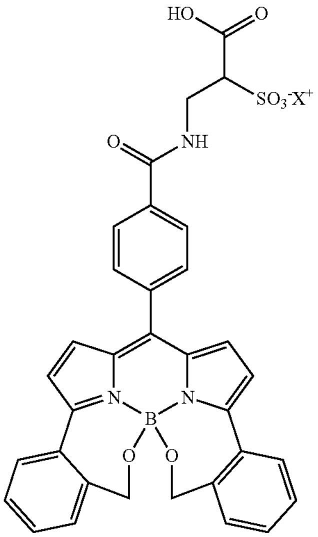
$X^+ =$
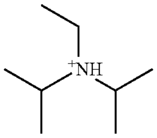
Compound (14)
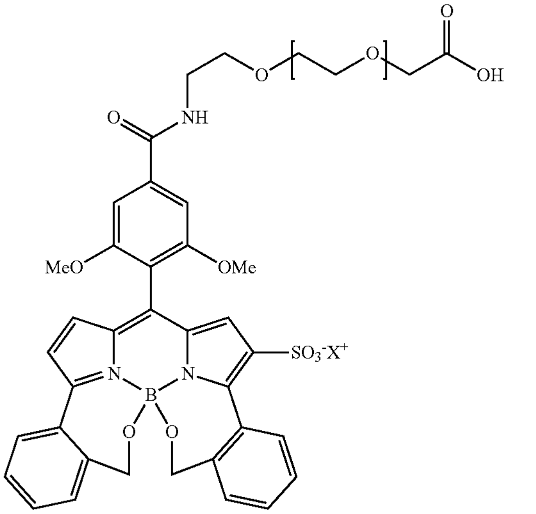
$X^+ = K^+$,
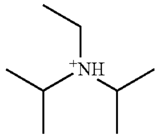

-continued
Compound (15)
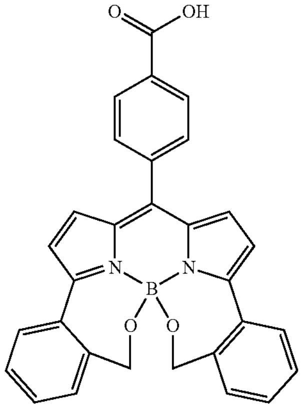
Compound (16)
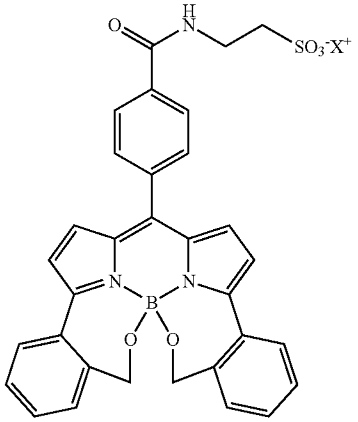
$X^+$ =
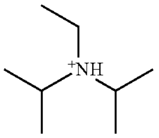
Compound (17)
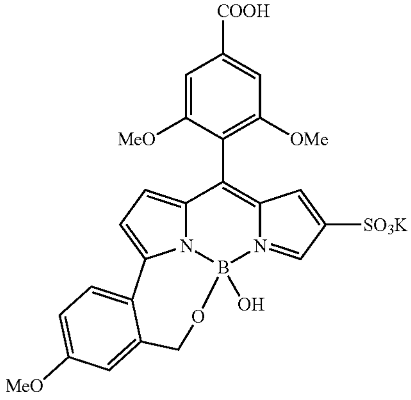
-continued
Compound (18)
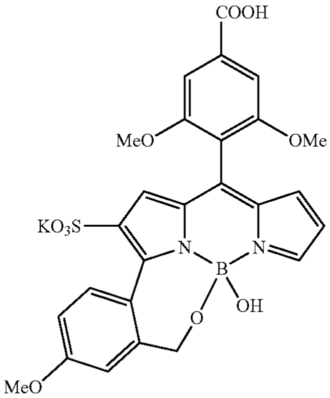
Compound (19)
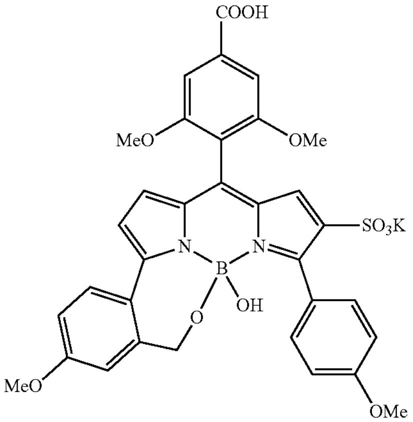
Compound (20)
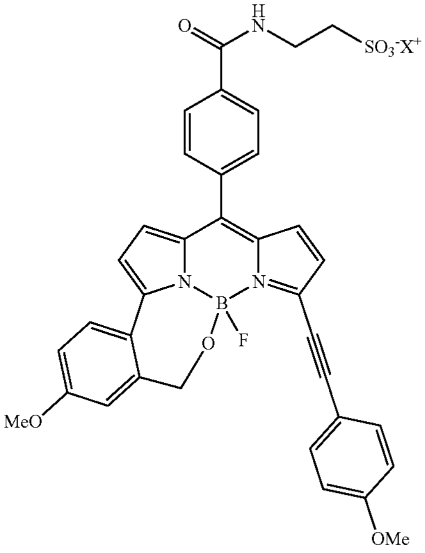
$X^+$ =
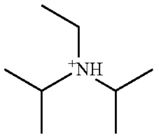

-continued

Compound (21)

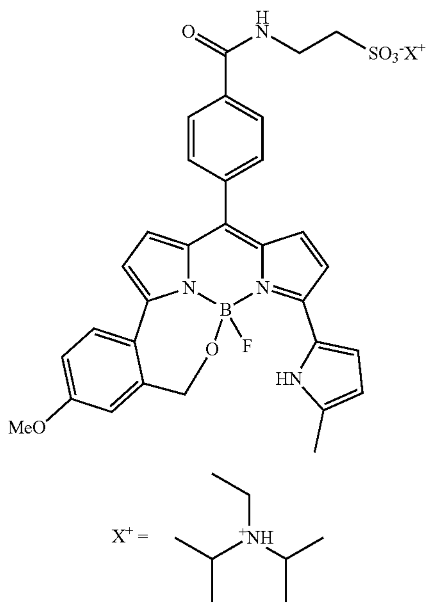

Comparative compound (1)

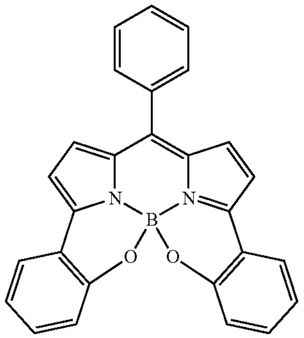

Comparative compound (2)

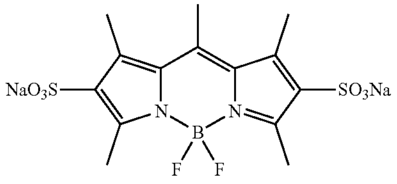

Compound (22)

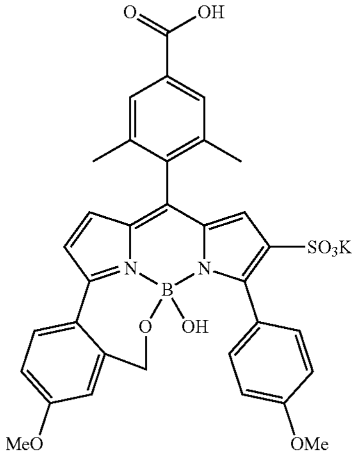

-continued

Compound (23)

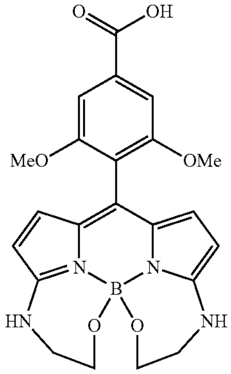

Compound (24)

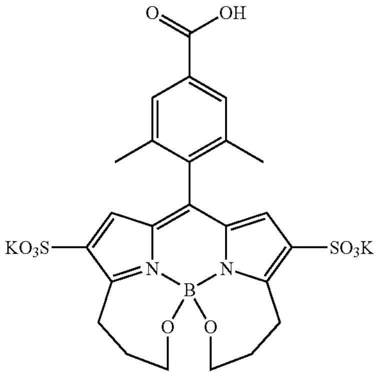

The comparative compound (1) is the compound A described in paragraph [0052] of WO2013/035303A.

The comparative compound (2) is BODIPY (registered trademark) 496/512 (manufactured by Thermo Fisher Scientific, Inc., trade name).

The methods for synthesizing the compounds (1) to (24) and labeled antibodies (1) to (12) used in each Example are described in detail below, but the starting materials, the dye intermediates and, the synthetic routes are not limited thereto.

Unless otherwise specified, as the carrier in the silica gel column chromatography, SNAP KP-Sil Cartridge (manufactured by Biotage, LLC) and High-Flash column W001, W002, W003, W004, or W005 [manufactured by Yamazen Corporation] were used.

As NH silica, SNAP KP-NH Cartridge (manufactured by Biotage, LLC) was used. The mixing ratio in the eluent is based on a volume ratio. For example, “chloroform:methanol=90:10 to 50:50” means that the an eluent of “chloroform:methanol=90:10” is changed to an eluent of “chloroform:methanol=50:50”.

For preparative thin layer silica gel chromatography, PLC glass plate silica gel $F_{60}$ (manufactured by Merck KGaA) was used. As NH silica, PLC05 Plates NH [manufactured by Fuji Silysia Chemical Ltd.] was used.

Representative conditions are as follows.

Column: BEHC 181.7 m, 2.1×30 mm, manufactured by Waters Corporation

Solvent: A liquid: 0.1% formic acid-water

B liquid: 0.1% formic acid-acetonitrile

Gradient cycle: 0.00 min (A liquid/B liquid=95/5), 2.00 min (A liquid/B liquid=5/95), 3.00 min (A liquid/B liquid=5/95), 3.01 min (A liquid/B liquid=100/0), 3.80 min (A liquid/B liquid=100/0)

Flow rate: 0.5 ml/min

Column temperature: room temperature

Detection wavelength: 254 nm

In the present invention, room temperature (r. t.) means 25° C.

In addition, the retention time (RT) was measured using SQD (manufactured by Waters Corporation) and indicated in minutes (min).

The description in each Synthesis Example is specifically as follows.

RT (min): Retention time (minutes)

The MS spectrum was measured by ACQUITY SQD LC/MS System [manufactured by Waters Corporation, ionization method: electrospray Ionization (ESI)] or LCMS-2010EV [manufactured by Shimadzu Corporation, ionization method: an ionization method simultaneously performing ESI and atmospheric pressure chemical ionization (APCI)].

MS means MS (ESI m/z):$[M+H]^+$, unless otherwise specified.

Initiator Sixty (manufactured by Biotage, LLC) was used as a microwave reactor.

Unless otherwise specified, the fluorescent compound, comparative compound, and labeled antibody used in each Example were those stored under the light-shielded conditions in a case where not used immediately after preparation. In addition, the commercially available comparative compound and reference labeled antibody were stored under the light-shielded conditions after purchase until use.

[Synthesis of Compound]

The abbreviations used in the synthesis of each compound described below indicate the following compounds.

CPME: cyclopentyl methyl ether

DDQ: 2,3-dichloro-5,6-dicyano-1,4-benzoquinone

DCC: dicyclohexylcarbodiimide

HATU: 1-[bis(dimethylamino)methylene]-1H-1,2,3-triazolo[4,5-b]pyridinium 3-oxide hexafluorophosphate NBS: N-bromosuccinimide NHS: N-hydroxysuccinimide GABA: γ-aminobutyric acid $PdCl_2$ (dtbpf): [1,1'-bis(di-tert-butylphosphino)ferrocene] palladium(II) dichloride RuPhos: 2-dicyclohexylphosphino-2',6'-diisopropoxybiphenyl TFA: trifluoroacetic acid DIPEA: diisopropylethylamine DCM: dichloromethane DMAP: 4-dimethylaminopyridine DMF: N,N-dimethylformamide DMSO: dimethyl sulfoxide PBS: phosphate buffered saline THF: tetrahydrofuran Anti-IgG: anti-mouse IgG antibody Ac: acetyl group Boc or BOC: tert-butoxycarbonyl group Bu: butyl group Me: methyl group Et: ethyl group PEG: polyethylene glycol iPr: isopropyl group TMS: trimethylsilyl group Synthesis Example 1

A compound (1) was synthesized based on the following scheme.

1) Synthesis of Compound (1-C)

The following compound (1-A), compound (1-B), and compound (1-C) were each synthesized according to the methods described in Chem. Eur. J. 2016, 22, 93-96, and Org. Process Res. Dev. 2015, 19, 1774-1783.

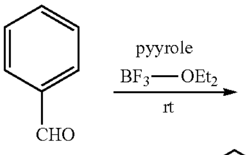

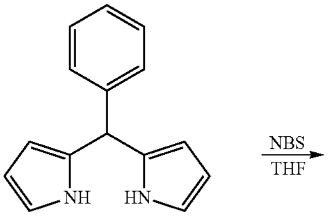

Compound (1-A)

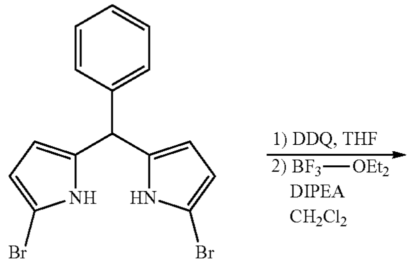

Compound (1-B)

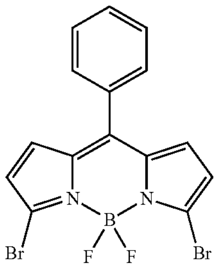

Compound (1-C)

2) Synthesis of Compound (1)

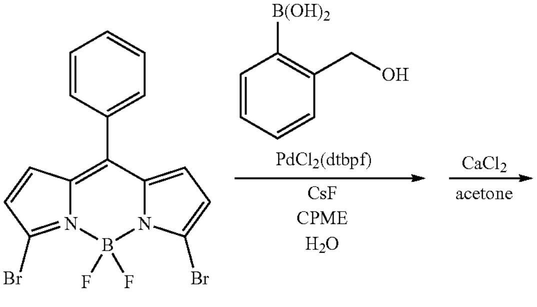

Compound (1-C)

-continued

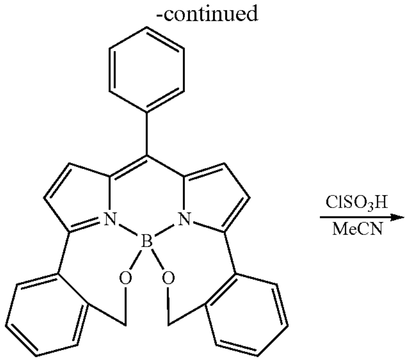

Compound (1-D)

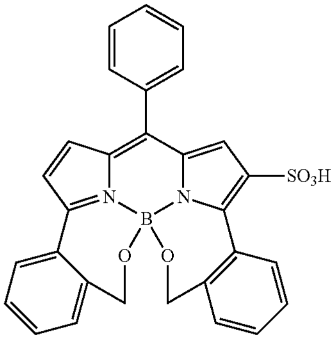

Compound (1)

2-1) Synthesis of Compound (1-D)

To 11 mL of a CPME solution of 112 mg of the compound (1-C), 0.02 mL of water, 76 mg of 2-(hydroxymethyl) phenylboronic acid [manufactured by FUJIFILM Wako Pure Chemical Corporation], 16 mg of $PdCl_2$ (dtbpf) [manufactured by Tokyo Chemical Industry Co., Ltd.)], and cesium fluoride (152 mg) (manufactured by FUJIFILM Wako Pure Chemical Corporation) were added, and the resultant mixture was stirred with heating under reflux for 90 minutes. After the reaction solution was cooled to room temperature, saturated aqueous sodium hydrogen carbonate was added to the reaction solution, followed by extraction with ethyl acetate three times, and the solvent was removed by evaporation under reduced pressure. The obtained residue was purified by being subjected to silica gel column chromatography (hexane:ethyl acetate=100:0 to 50:50), and the solvent was removed by evaporation under reduced pressure.

The obtained product was made into a solution in 20 mL of acetone solution, 90 mg of calcium chloride was added thereto, and the resultant mixture was stirred at 160° C. for 30 minutes in a microwave reactor. Then, the reaction solution was directly purified by silica gel column chromatography (ethyl acetate only), and the solvent was removed by evaporation under reduced pressure to obtain 31 mg of the compound (1-D) (reddish brown solid).

MS (ESI m/z): 441 (M+H)

RT (min): 1.83

2-2) Synthesis of Compound (1)

3 μL of chlorosulfonic acid [manufactured by FUJIFILM Wako Pure Chemical Corporation] was added to 2 mL of an acetonitrile solution containing 4.5 mg of the compound (1-D), and the resultant mixture was stirred at room temperature for 5 minutes. Then, the reaction solution was directly purified by preparative thin layer silica gel chromatography (methanol:chloroform=20:80) to obtain 1 mg of the compound (1) (reddish brown solid).

MS (ESI m/z): 521 (M+H)

RT (min): 1.19

Synthesis Example 2

A compound (2) was synthesized based on the following scheme.

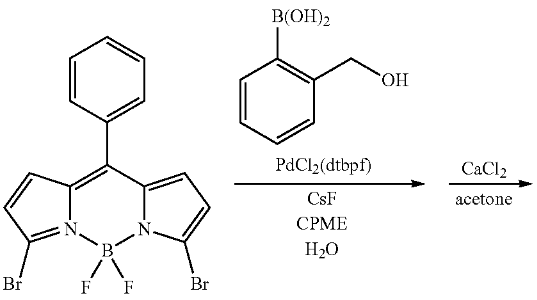

Compound (1-C)

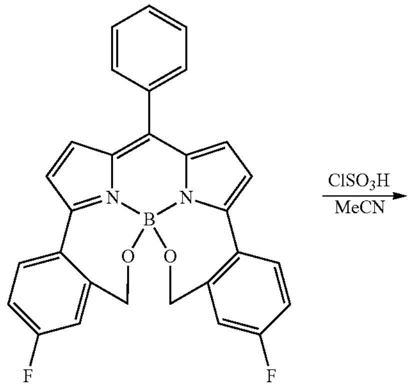

Compound (2-A)

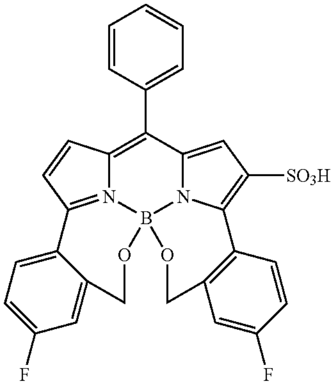

Compound (2)

1 mg of the compound (2) (reddish brown solid) was obtained in the same manner as in the method for synthesizing the compound (1), except that 2-(hydroxymethyl) phenylboronic acid was changed to 4-fluoro-2-(hydroxymethyl)phenylboronic acid [manufactured by Combi-Blocks Inc.] in the method for synthesizing the compound (1).

MS (ESI m/z): 557 (M+H)

RT (min): 1.28

Synthesis Example 3

A compound (3) was synthesized based on the following scheme.

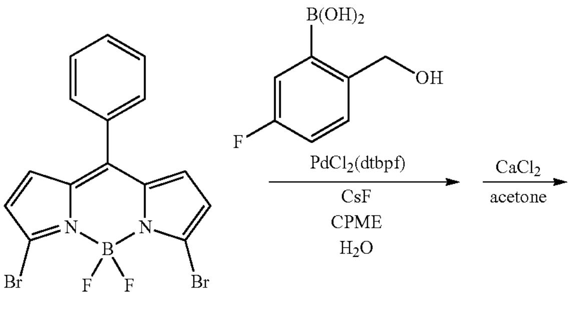

Compound (1-C)

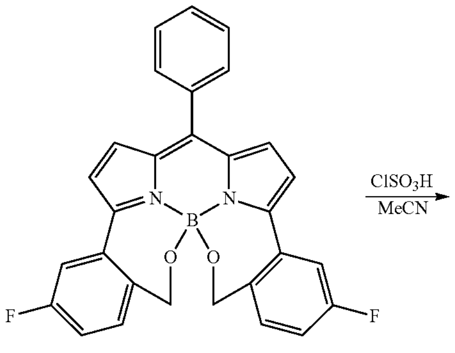

Compound (3-A)

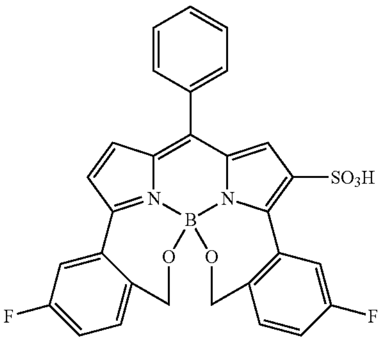

Compound (3)

1 mg of the compound (3) (reddish brown solid) was obtained in the same manner as in the method for synthesizing the compound (1), except that 2-(hydroxymethyl) phenylboronic acid was changed to 5-fluoro-2-(hydroxymethyl)phenylboronic acid [Luminescence Technology Corp.] in the method for synthesizing the compound (1).

MS (ESI m/z): 557 (M+H)

RT (min): 1.28

Synthesis Example 4

A compound (4) and a labeled antibody (1) were synthesized based on the following schemes.

1) Synthesis of Compound (4)

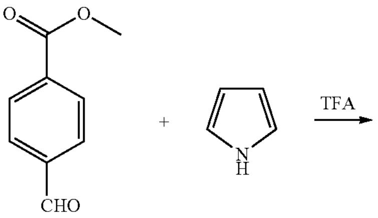

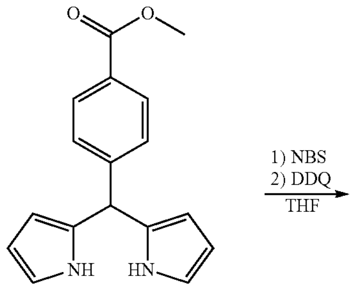

Compound (4-A)

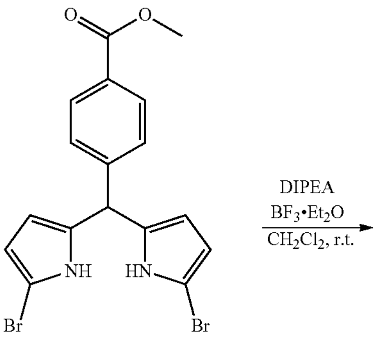

Compound (4-B)

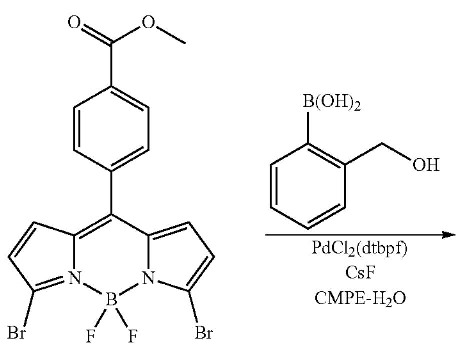

Compound (4-C)

-continued
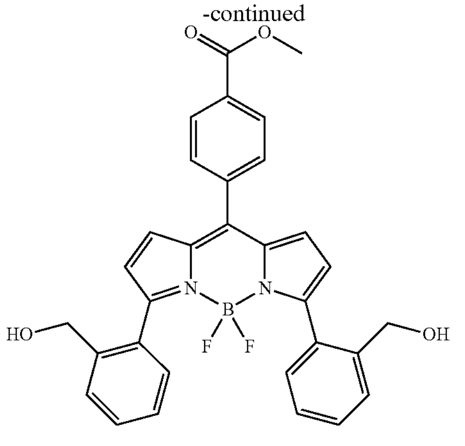
Compound (4-D)
+
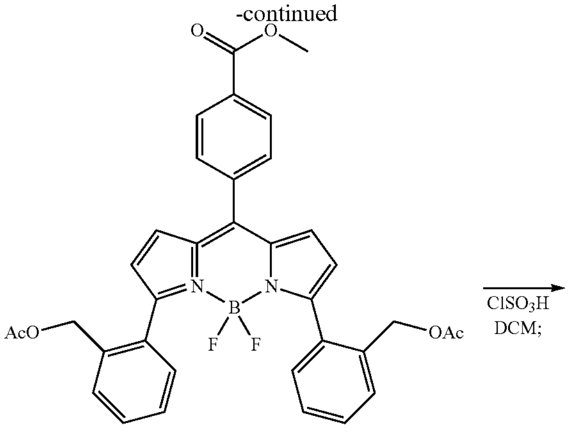
Compound (4-E)
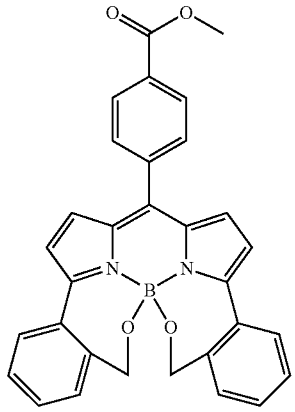
Compound (15-A)
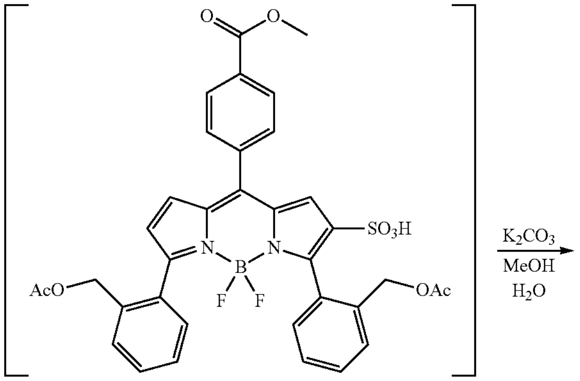
Compound (4-E)
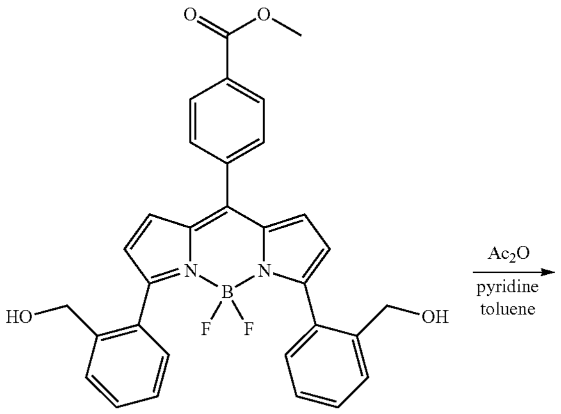
Compound (4-D)
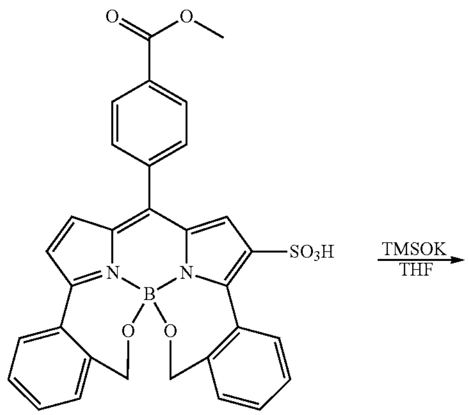
Compound (4-F)

-continued

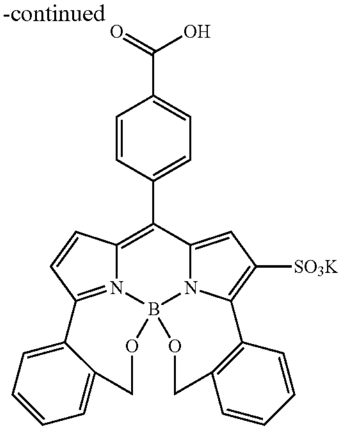

Compound (4)

5 g of methyl p-formylbenzoate and 36 g of pyrrole were put into a 300 ml three-necked flask and subjected to nitrogen purge. The internal temperature was adjusted to 10° C. in an ice bath, and 0.115 ml of trifluoroacetic acid was added dropwise with stirring. Then, the reaction solution was returned to room temperature and stirred for 2 hours. The reaction solution was purified by silica gel column chromatography (eluent: ethyl acetate/hexane=0/100 to 50/50 with gradient), and then 60 ml of hexane and 3 ml of isopropanol were added to the purified product and stirred. The precipitate was filtrated for separation, washed with hexane, and then dried to obtain 4.7 g of the compound (4-A).

The compound (4-A) (4.7 g) and tetrahydrofuran (80 ml) were added to a 500 ml three-necked flask, and the resultant mixture was cooled to −60° C. or lower in an acetone-dry ice bath while stirring in the nitrogen atmosphere. A solution prepared by dissolving 6.3 g of N-bromosuccinimide in 60 ml of tetrahydrofuran was dropwise added thereto and reacted for minutes, and subsequently, a solution obtained by dissolving 4.19 g of 2,3-dichloro-5,6-dicyano-1,4-benzoquinone in 60 ml of tetrahydrofuran was dropwise added thereto and reacted for 70 minutes. Then, tetrahydrofuran was removed by evaporation using a rotary evaporator for concentration, whereby a crude product was obtained. The crude product was dissolved in dichloromethane and purified by silica gel column chromatography using ethyl acetate/hexane=0/100 to 40/60 as an eluent to obtain 4.0 g of the compound (4-B).

4.0 g of the compound (4-B) and 100 ml of dichloromethane were added to a 500 ml three-necked flask, and the resultant mixture was cooled to 0° C. in an ice bath sprinkled with salt while stirring in the nitrogen atmosphere. 5.6 ml of N,N-diisopropylethylamine was added thereto, and after 10 minutes 6.3 ml of a boron trifluoride-diethyl ether complex was added thereto, and the resultant mixture was reacted at 0° C. for 30 minutes. Then, 100 ml of a saturated aqueous solution of sodium hydrogen carbonate was dropwise added thereto, and the resultant mixture was stirred. The organic layer was extracted and concentrated with a rotary evaporator. The concentrated organic layer was dissolved in a minimum amount of dichloromethane and purified by silica gel column chromatography using ethyl acetate/hexane=0/100 to 100/0 as an eluent. The purified product was dissolved in a minimum amount of dichloromethane, methanol was added thereto, the dichloromethane was removed by evaporation with a rotary evaporator under reduced pressure, and then the precipitate was filtrated. The filtrated precipitate was washed with methanol and dried to obtain 3.0 g of the compound (4-C).

1.73 g of the compound (4-C), 239 ml of CPME, 0.4 ml of water, 3.26 g of cesium fluoride, 1.82 g of o-(hydroxymethyl)phenylboronic acid were added to a 500 ml three-necked flask, and the resultant mixture was degassed and subjected to nitrogen purge while stirring. Then, 300 mg of $PdCl_2$ (dtbpf) was added thereto, and the resultant mixture was stirred at an external temperature of 120° C. for 1 hour. After cooling, the mixture was filtrated through Celite, and a liquid separation operation was performed with ethyl acetate/distilled water. The organic layer was concentrated under reduced pressure and purified by silica gel column chromatography using ethyl acetate/hexane=0/100 to 100/0 as an eluent to obtain 0.58 g of the compound (4-D) and 0.15 g of the compound (5-A).

0.50 g of the compound (4-D), 9 ml of toluene, and 0.2 ml of pyridine were put into a 300 ml three-necked flask. 0.2 ml of acetic anhydride was dropwise added thereto with stirring in the nitrogen atmosphere, and then the resultant mixture was stirred at an external temperature of 140° C. for 4 hours. The reaction solution was returned to room temperature, 0.1 ml of acetic acid and 9 ml of distilled water were added thereto, and after stirring the resultant mixture for 30 minutes, the organic layer was extracted by a liquid separation operation. The organic layer was purified by silica gel column chromatography using ethyl acetate/hexane=0/100 to 50/50 as an eluent to obtain 0.32 g of the compound (4-E).

The compound (4-E) (50 mg) and dichloromethane (8 ml) were put into a 100 ml three-necked flask and subjected to nitrogen purge while stirring. 0.013 ml of chlorosulfonic acid was added thereto with stirring, and the resultant mixture was reacted at room temperature. Then, 0.111 g of potassium carbonate, 0.8 ml of methanol, and 4 ml of distilled water were added thereto, and the resultant mixture was reacted at room temperature. The reaction solvent was removed by evaporation under reduced pressure, and the obtained residue was purified by reverse-phase column chromatography (SNAP Column Ultra C18, manufactured by Biotage, LLC) using acetonitrile/water=0/100 to 25/75 as an eluent to obtain 30 mg of the compound (4-F).

30 mg of the compound (4-F) and 1 ml of tetrahydrofuran (containing a stabilizer) were put into a 50 ml egg-plant shaped flask, 23 mg of potassium trimethylsilanolate was added thereto with stirring in the nitrogen atmosphere, and the resultant mixture was reacted at room temperature for 1.5 hours. After adding 2 ml of distilled water, the reaction solution was purified by reverse-phase column chromatography (SNAP Column Ultra C18, manufactured by Biotage, LLC) using acetonitrile/water=0/100 to 25/75 as an eluent to obtain 5 mg of the compound (4).

MS (ESI m/z): 565 (M−K+2H)

RT (min): 1.07

2) Synthesis of Labeled Antibody (1)

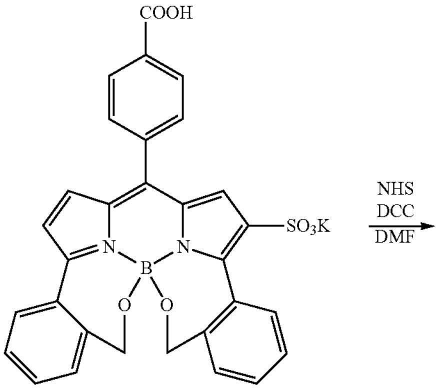

Compound (4)

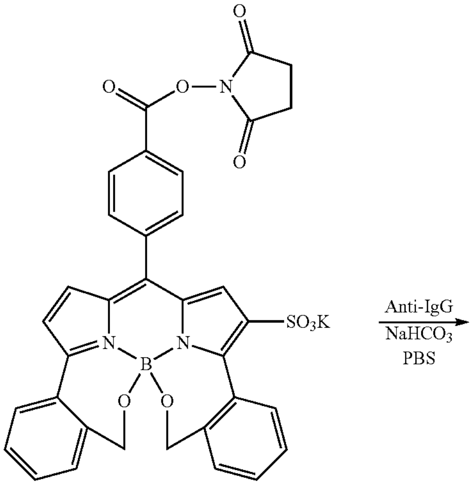

Compound (4-NHS)

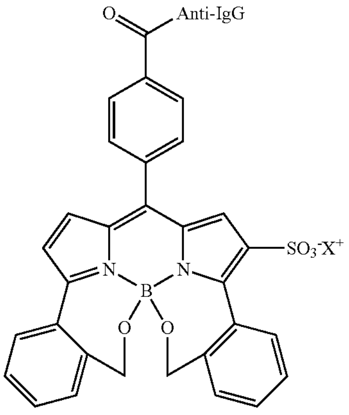

Labeled antibody (1)

$X^+ = K^+, Na^+$

To 1 mL of a DMF solution containing 6 mg of the compound (4), 3 mg of N-hydroxysuccinimide [manufactured by FUJIFILM Wako Pure Chemical Corporation] and 12 mg of dicyclohexylcarbodiimide [manufactured by FUJIFILM Wako Pure Chemical Corporation] were added, and the resultant mixture was stirred at room temperature for 14 hours. Subsequently, the reaction solution was directly purified by reverse-phase silica column chromatography [SNAP12 column Ultra C18, manufactured by Biotage, LLC](acetonitrile:water=0:100 to 20:80), and the fraction was collected and freeze-dried, thereby obtaining 3 mg of the compound (4-NHS) (reddish brown solid).

MS (ESI m/z): 662 (M+H)

To 400 μL of anti-mouse IgG antibody [host: goat, 2.4 mg/mL, catalog number: 115-005-003, manufactured by Jackson ImmunoResearch Inc.], 10 μL of an aqueous solution of 0.2M sodium hydrogen carbonate solution and 3.2 μL of a DMSO solution containing the compound (4-NHS) at a concentration of 20 mM were added, and the resultant mixture was stirred and allowed to be left at room temperature for 1 hour. Subsequently, the reaction solution was directly applied onto a Sephadex G-25 column [catalog number: 17085101, manufactured by GE Healthcare] and purified by using PBS [pH=7.4, manufactured by FUJIFILM Wako Pure Chemical Corporation], thereby obtaining the labeled antibody (1).

Synthesis Example 5

A compound (5) and a labeled antibody (2) were synthesized based on the following schemes.

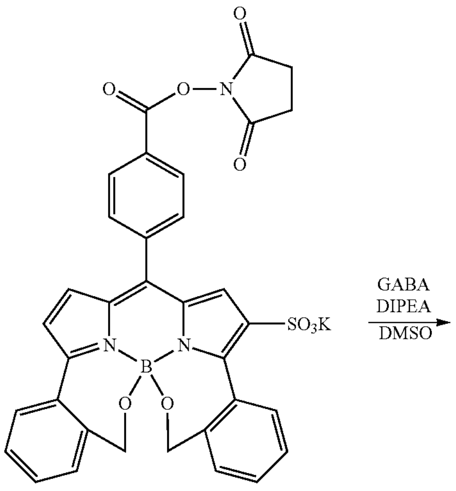

Compound (4-NHS)

-continued

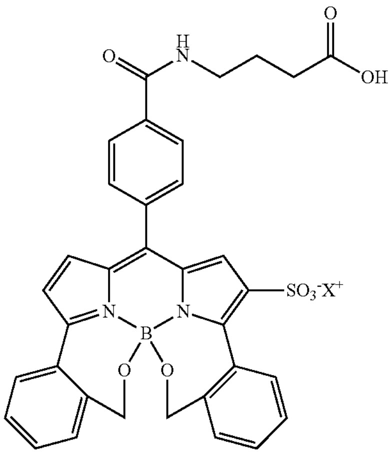

Compound (5)

$X^+ = K^+$,

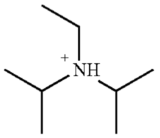

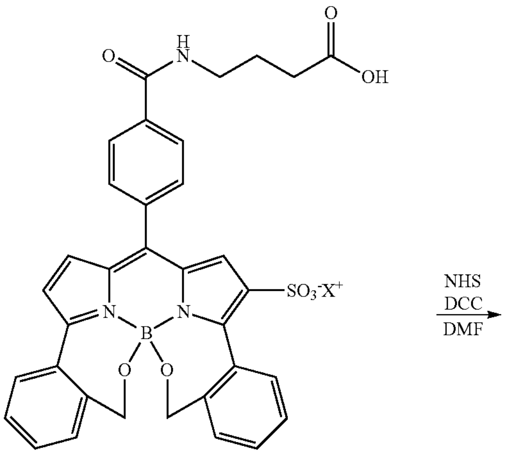

Compound (5)

-continued

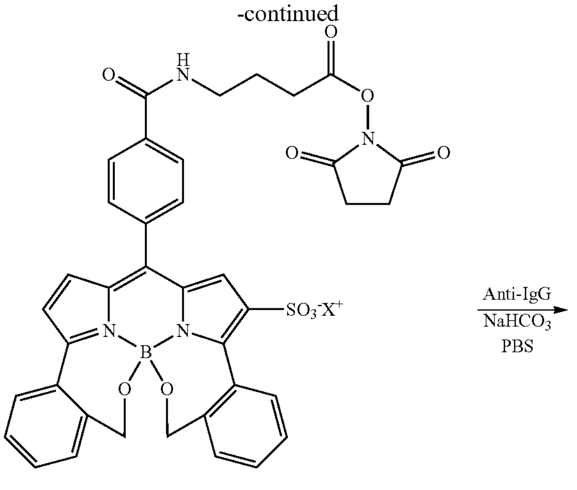

Compound (5-NHS)

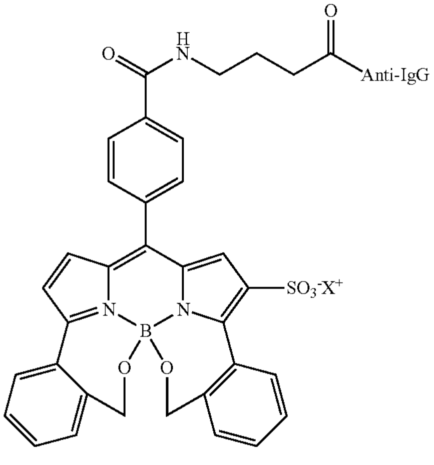

Labeled antibody (2)

$X^+ = K^+, Na^+$,

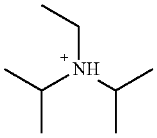

To 43 μL of a DMSO solution containing 3 mg of the compound (4-NHS), 2 μL of diisopropylethylamine (manufactured by FUJIFILM Wako Pure Chemical Corporation) and 1 mg of 7-aminobutyric acid (manufactured by FUJIFILM Wako Pure Chemical Corporation) were added, and the resultant mixture was stirred at room temperature for 3.5 hours. Subsequently, the reaction solution was directly purified by reverse-phase silica column chromatography [SNAP12 column Ultra C18, (manufactured by Biotage, LLC](acetonitrile:water=0:100 to 20:80), and the fraction was collected and freeze-dried, thereby obtaining 2 mg of the compound (5) (reddish brown solid).

MS (ESI m/z): 650 (M−2X+3H)

1 mg of the compound (5-NHS) (reddish brown solid) was obtained in the same manner as in the method of synthesizing the compound (4-NHS), except that the compound (4) was changed to the compound (5).

MS (ESI m/z): 747 (M−X+2H)

The labeled antibody (2) was obtained in the same manner as in the method of synthesizing the labeled antibody (1), except that the compound (4-NHS) was changed to the compound (5-NHS).

Synthesis Example 6

A compound (6) and a labeled antibody (3) were synthesized based on the following schemes.

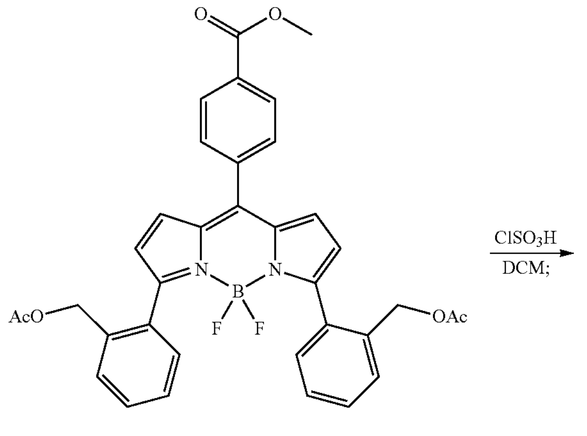

Compound (4-E)

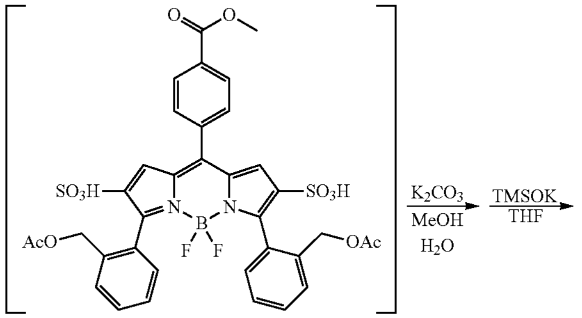

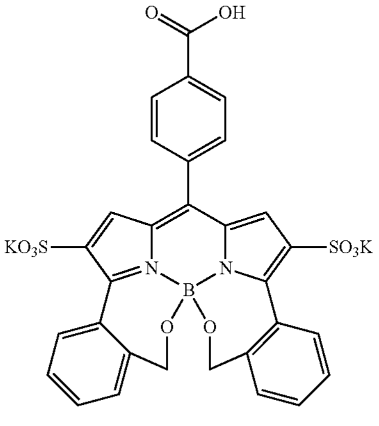

Compound (6)

-continued

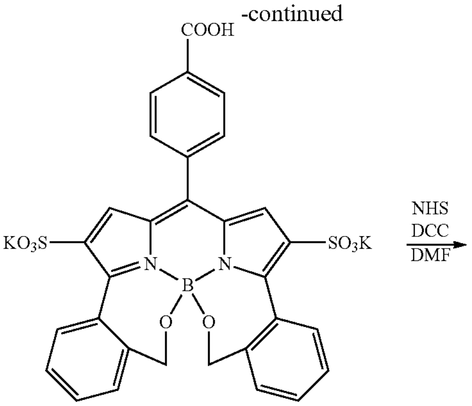

Compound (6)

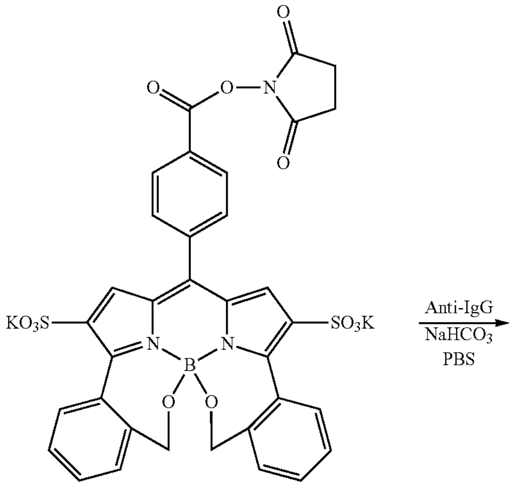

Compound (6-NHS)

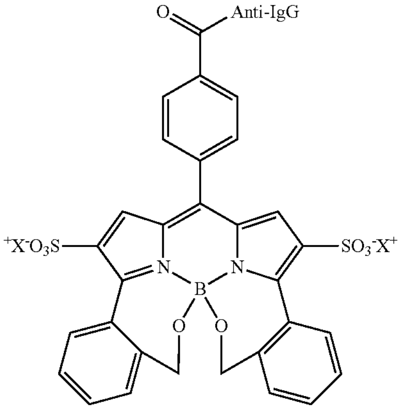

Labeled antibody (3)

$X^+ = K^+, Na^+$ 0.3 mg of the compound (6) (reddish brown solid) was obtained in the same manner as in the method of synthesizing the compound (4) from the compound (4-E), except that the amount of chlorosulfonic acid was changed from 0.013 ml to 0.026 ml and acetonitrile/water=25/75 in the eluent of reversed-phase column chromatography was changed to acetonitrile/water=10/90.

MS (ESI m/z): 645 (M−2K+3H)

0.1 mg of the compound (6-NHS) (reddish brown solid) was obtained in the same manner as in the method of synthesizing the compound (4-NHS), except that the compound (4) was changed to the compound (6).

MS (ESI m/z): 780 (M−2K+3H)

The labeled antibody (3) was obtained in the same manner as in the method of synthesizing the labeled antibody (1), except that the compound (4-NHS) was changed to the compound (6-NHS).

Synthesis Example 7

A compound (7) and a labeled antibody (4) were synthesized based on the following schemes.

1) Synthesis of Compound (7)

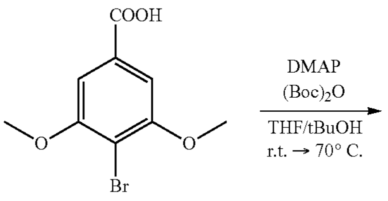

Compound (7-A)

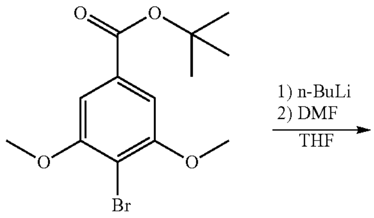

Compound (7-B)

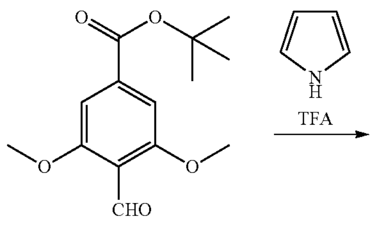

Compound (7-C)

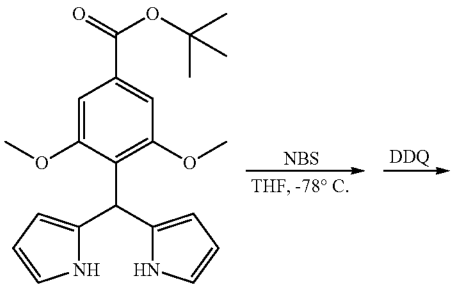

Compound (7-D)

-continued

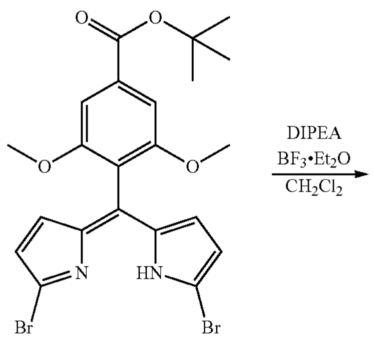

Compound (7-E)

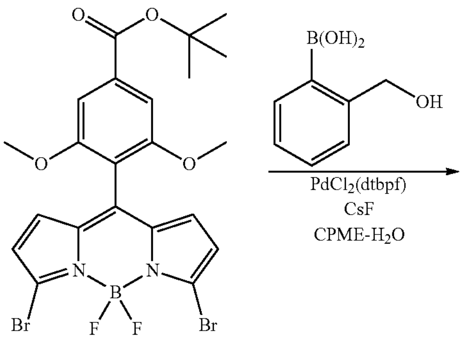

Compound (7-F)

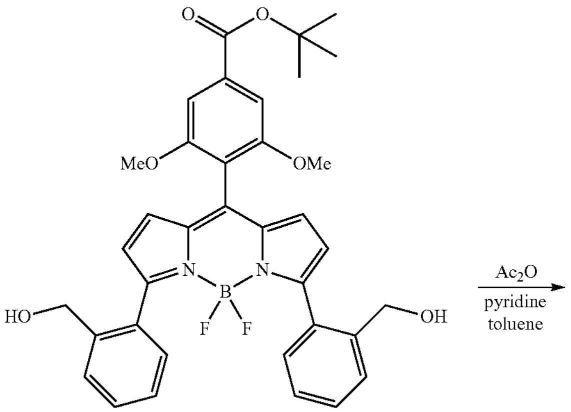

Compound (7-G)

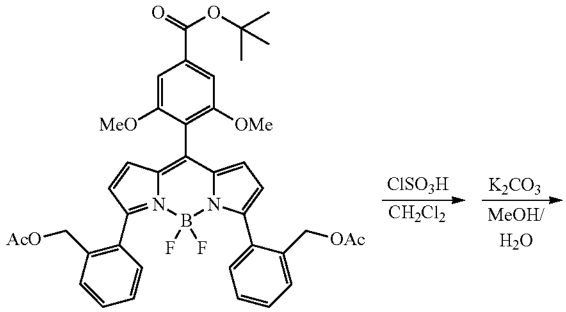

Compound (7-H)

-continued

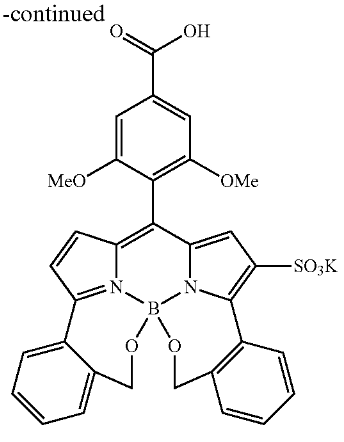

Compound (7)

A 1 L three-necked flask was subjected to nitrogen purge, 25 g of the compound (7-A), 17.55 g of DMAP, 125 ml of THF (extremely dehydrated, containing stabilizer), and 125 ml of t-butanol were added thereto, and 41.3 g of di-tert-butyl bicarbonate was dropwise added thereto while stirring at room temperature. After stirring for 4 hours, the mixture was allowed to be left overnight, then warmed to 70° C. and stirred with heating for 1 hour. After returning to room temperature, the solvent was removed by evaporation for concentration under reduced pressure. After adding 188 ml of ethanol and 15.4 g of imidazole, the resultant mixture was stirred for 3 hours. Then, the solvent was removed by evaporation under reduced pressure, 200 ml of hexane and 265 ml of ethyl acetate were added to the mixture, and then the resultant mixture was stirred at room temperature for 20 minutes. The precipitate was filtrated for separation and washed with 240 ml of a mixed solution of ethyl acetate/hexane=1/2 to obtain 50 g of a crude product. The crude product was dissolved in 50 ml of dichloromethane, 95 ml of hexane was added thereto, and the solution of the crude product was purified by silica gel column chromatography using ethyl acetate/hexane=0/100 to 5/95 to 15/85 as an eluent to obtain 18.2 g of the compound (7-B).

A 1 L three-necked flask was subjected to nitrogen purge, 18.23 g of the compound (7-B) and 414 ml of THF (extremely dehydrated, containing stabilizer) were added thereto, and the resultant mixture was cooled with stirring to −60° C. or lower using a dry ice-acetone bath. 36 ml of n-butyllithium was slowly added dropwise thereto, the reaction was performed for 30 minutes, 9 ml of DMF (extremely dehydrated) was slowly added dropwise thereto and stirred for 10 minutes, and then the temperature was raised to 0° C. to 10° C. and stirred for 2 hours. 200 ml of a saturated aqueous solution of ammonium chloride was dropwise added thereto, the resultant mixture was stirred for 30 minutes, and then 10 ml of a 30% aqueous hydrochloric acid was added dropwise. The resultant mixture was transferred to a 1 L liquid separating funnel, a small amount of ethyl acetate and an aqueous solution of 25% sodium chloride were added thereto to perform a liquid separation operation, and then magnesium sulfate was added to the separated solution, followed by drying and natural filtration. The solvent of the filtrated solution was removed by evaporation under reduced pressure to obtain 19.11 g of a crude product. The solution was prepared by adding 30 ml of dichloromethane and 30 ml of hexane and purified by silica gel column chromatography using ethyl acetate/hexane=0/100 to 10/90 to 20/80 as an eluent to obtain 12.25 g of the compound (7-C).

The compound (7-H) was synthesized in the same manner as in the method of synthesizing the compound (4-E), except that methyl p-formylbenzoate was changed to the compound (7-C). In addition, the compound (7) was synthesized by changing the compound (4-E) to compound (7-H), in the method of synthesizing the compound (4-E) from the compound (4-F).

MS (ESI m/z): 623 (M−K)

2) Synthesis of Labeled Antibody (4)

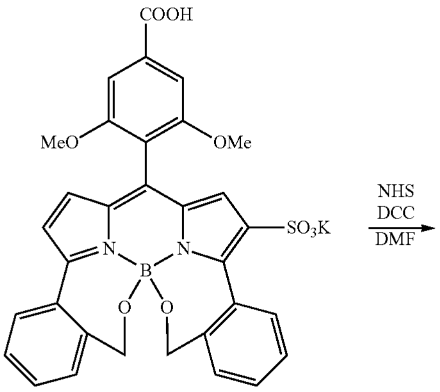

Compound (7)

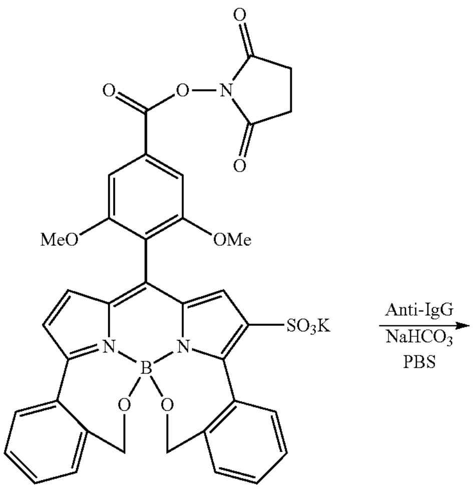

Compound (7-NHS)

-continued

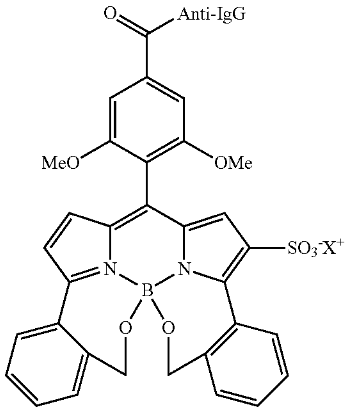

Labeled antibody (4)

$X^+ = K^+, Na^+$ 28 mg of the compound (7-NHS) (reddish brown solid) was obtained in the same manner as in the method of synthesizing the compound (4-NHS), except that the compound (4) was changed to the compound (7).

MS (ESI m/z): 722 (M−K+2H)

The labeled antibody (4) was obtained in the same manner as in the method of synthesizing the labeled antibody (1), except that the compound (4-NHS) was changed to the compound (7-NHS).

Synthesis Example 8

A compound (8) and a labeled antibody (5) were synthesized based on the following schemes.

-continued

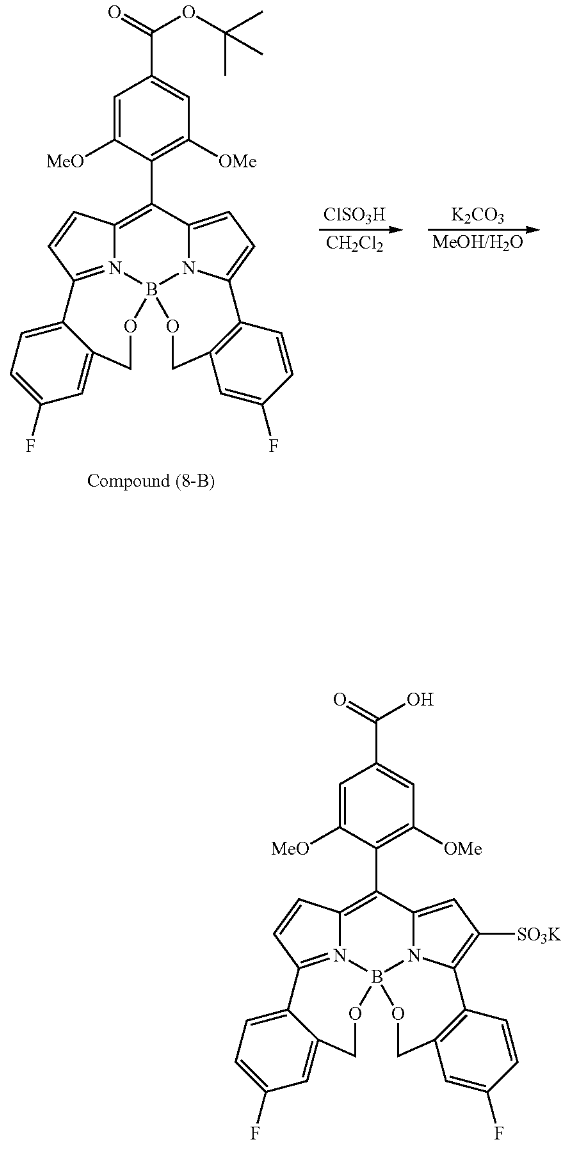

Compound (8-B)

Compound (8)

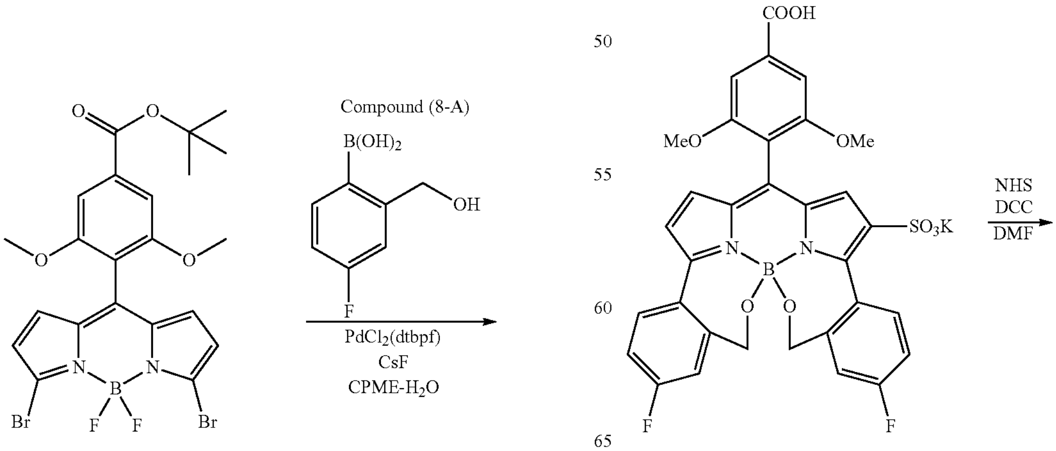

Compound (8-A)

Compound (7-F)

Compound (8)

-continued

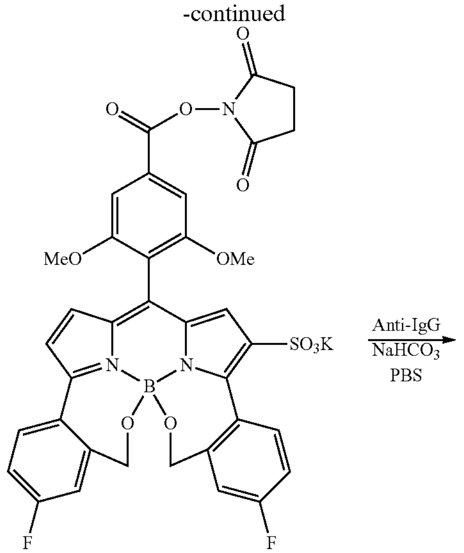

Compound (8-NHS)

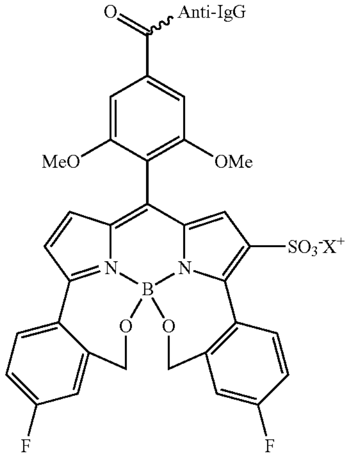

Labeled antibody (5)

$X^+ = K^+, Na^+$

The compound (8) was synthesized in the same manner as in the method of synthesizing the compound (7) from the compound (7-F), except that o-(hydroxymethyl)phenylboronic acid was changed to compound (8-A).

MS (ESI m/z): 659 (M−K)

20 mg of the compound (8-NHS) (reddish brown solid) was obtained in the same manner as in the method of synthesizing the compound (4-NHS), except that the compound (4) was changed to the compound (8).

MS (ESI m/z): 758 (M−K+2H)

The labeled antibody (5) was obtained in the same manner as in the method of synthesizing the labeled antibody (1), except that the compound (4-NHS) was changed to the compound (8-NHS).

Synthesis Example 9

A compound (9) and a labeled antibody (6) were synthesized based on the following schemes.

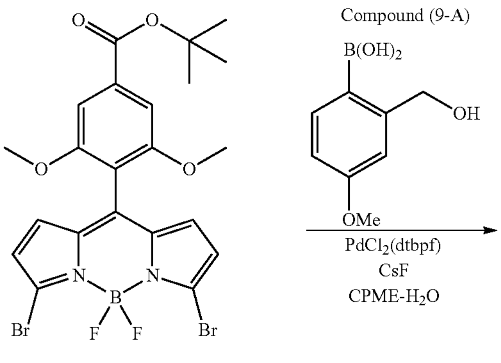

Compound (7-F)

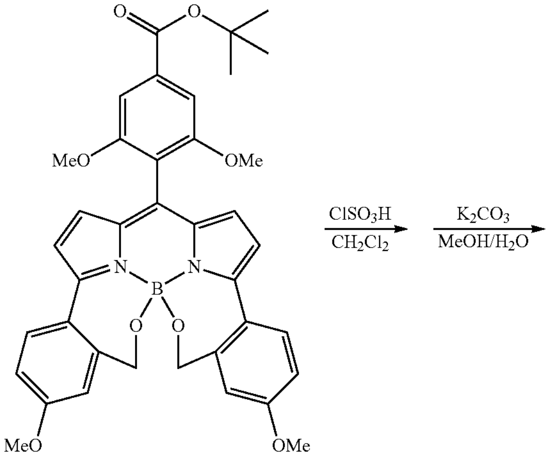

Compound (9-B)

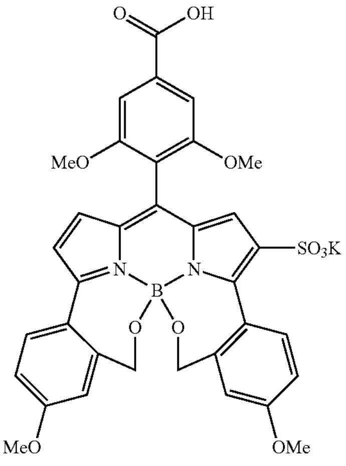

Compound (9)

-continued

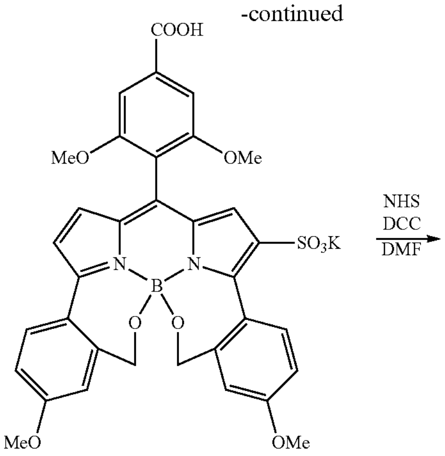

Compound (9)

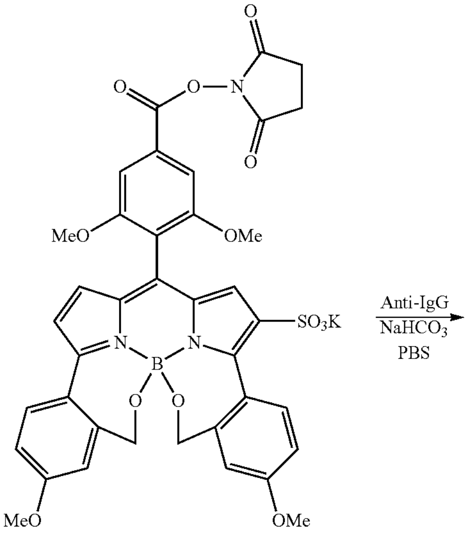

Compound (9-NHS)

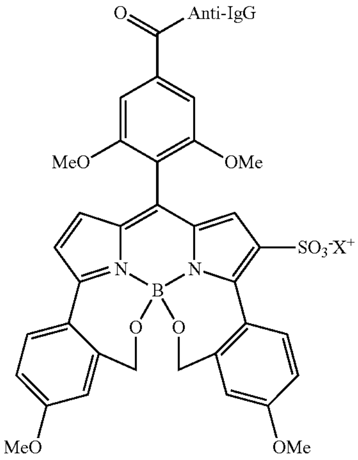

Labeled antibody (6)

$X^+ = K^+, Na^+$

The compound (9) was synthesized in the same manner as in the method of synthesizing the compound (7) from the compound (7-F), except that o-(hydroxymethyl)phenylboronic acid was changed to the compound (9-A).

MS (ESI m/z): 683 (M−K)

3 mg of the compound (9-NHS) (reddish brown solid) was obtained in the same manner as in the method of synthesizing the compound (4-NHS), except that the compound (4) was changed to the compound (9).

MS (ESI m/z): 782 (M−K+2H)

The labeled antibody (6) was obtained in the same manner as in the method of synthesizing the labeled antibody (1), except that the compound (4-NHS) was changed to the compound (9-NHS).

Synthesis Example 10

A compound (10) and a labeled antibody (7) were synthesized based on the following schemes.

1) Synthesis of Compound (10)

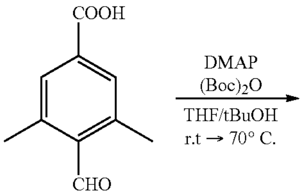

Compound (10-A)

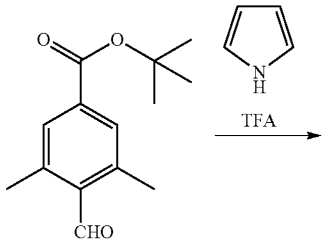

Compound (10-B)

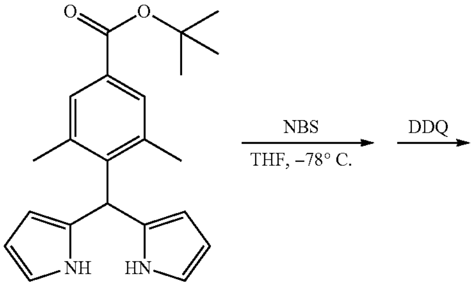

Compound (10-C)

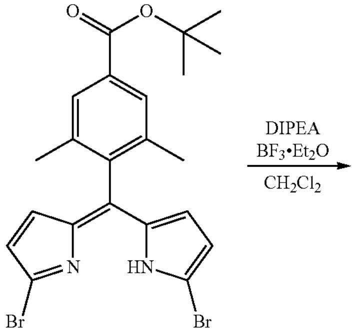

Compound (10-D)

-continued

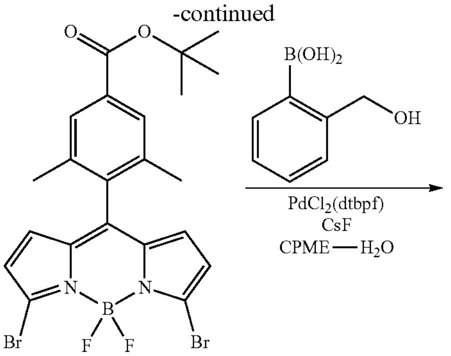

Compound (10-E)

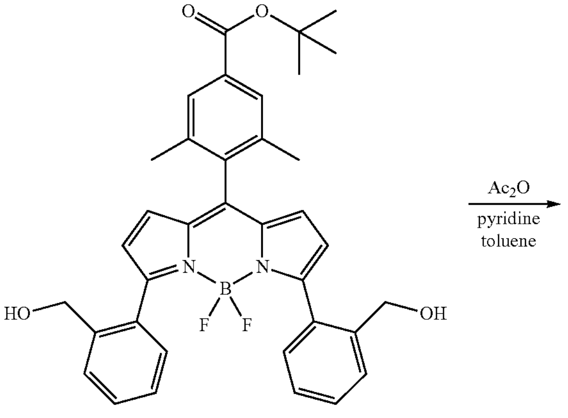

Compound (10-F)

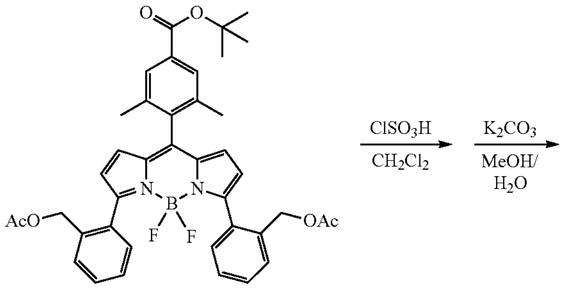

Compound (10-G)

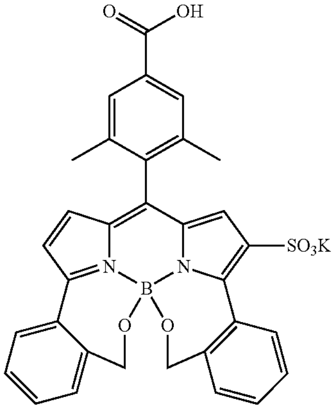

Compound (10)

The compound (10-B) was synthesized in the same manner as in the method of synthesizing the compound (7-B), except that the compound (7-A) was changed to the compound (10-A).

The compound (10) was synthesized in the same manner as in the method of synthesizing the compound (7) from the compound (7-C), except that the compound (7-C) was changed to the compound (10-B).

MS (ESI m/z): 591 (M−K)

2) Synthesis of Labeled Antibody (7)

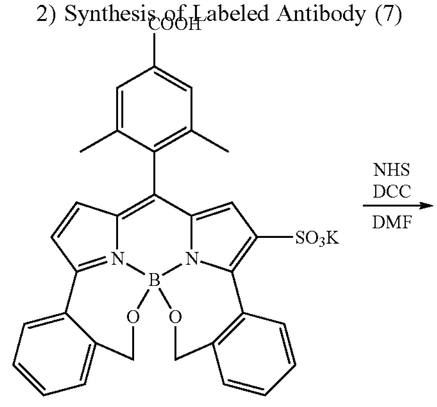

Compound (10)

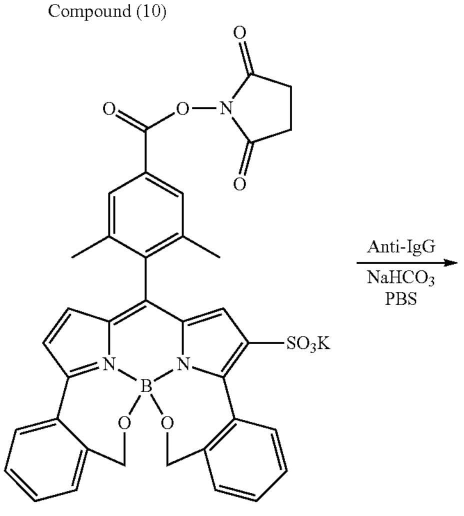

Compound (10-NHS)

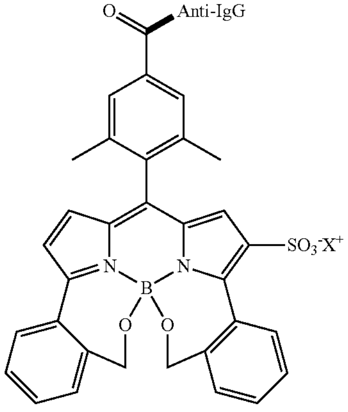

$X^+ = K^+, Na^+$

Labeled antibody (7)

13 mg of the compound (10-NHS) (reddish brown solid) was obtained in the same manner as in the method of synthesizing the compound (4-NHS), except that the compound (4) was changed to the compound (10).

MS (ESI m/z): 690 (M−K+2H)

The labeled antibody (7) was obtained in the same manner as in the method of synthesizing the labeled antibody (1), except that the compound (4-NHS) was changed to the compound (10-NHS).

Synthesis Example 11

A compound (11) and a labeled antibody (8) were synthesized based on the following schemes.

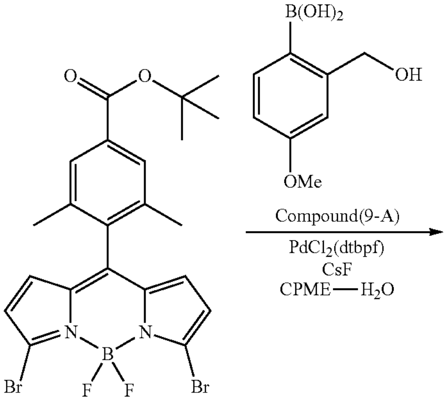

Compound (10-E)

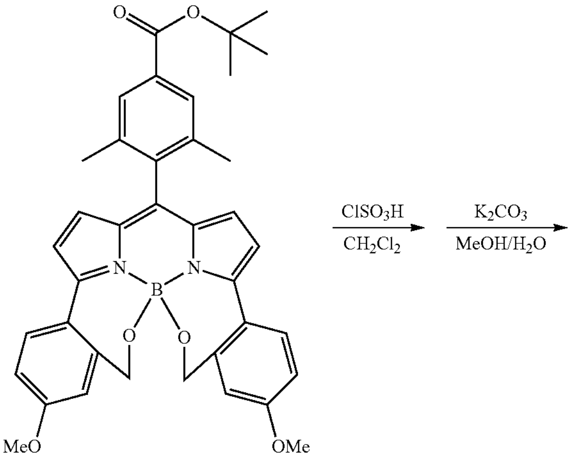

Compound (11-A)

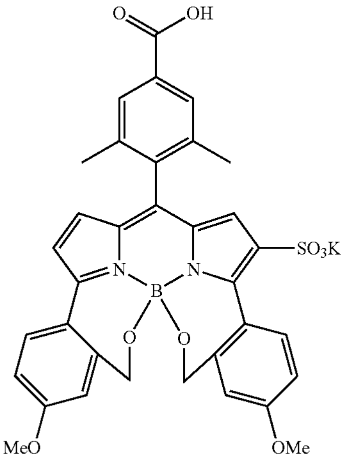

Compound (11)

-continued

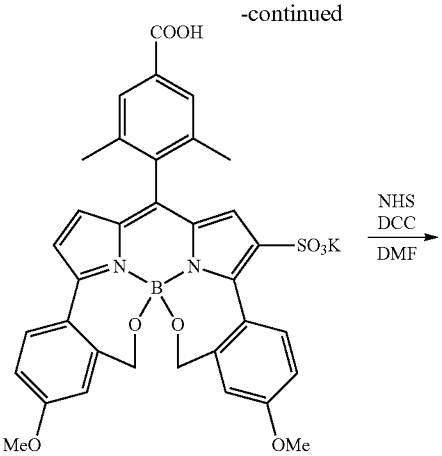

Compound (11)

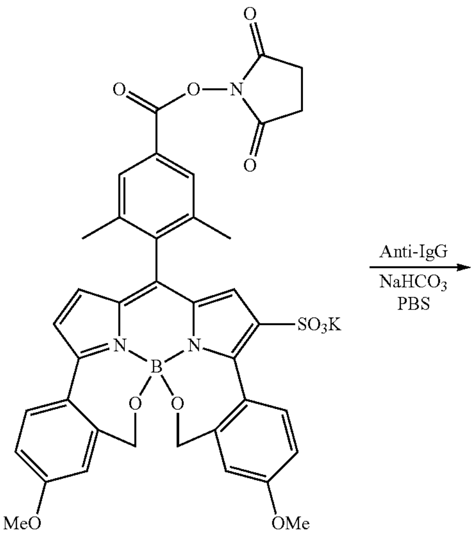

Compound (11-NHS)

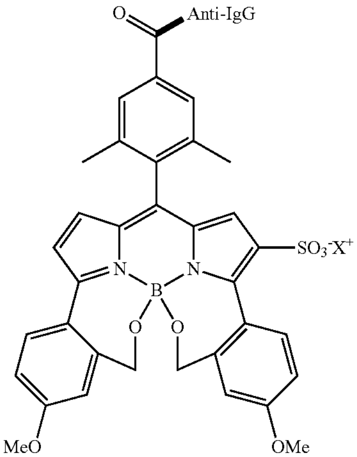

$X^+ = K^+, Na^+$

Labeled antibody (8)

The compound (11) was synthesized in the same manner as in the method of synthesizing the compound (9), except that the compound (7-F) was changed to the compound (10-E).

MS (ESI m/z): 651 (M−K)

3 mg of the compound (11-NHS) (reddish brown solid) was obtained in the same manner as in the method of synthesizing the compound (4-NHS), except that the compound (4) was changed to the compound (11).

MS (ESI m/z): 750 (M−K+2H)

The labeled antibody (8) was obtained in the same manner as in the method of synthesizing the labeled antibody (1), except that the compound (4-NHS) was changed to the compound (11-NHS).

Synthesis Example 12

A compound (12) and a labeled antibody (9) were synthesized based on the following schemes.

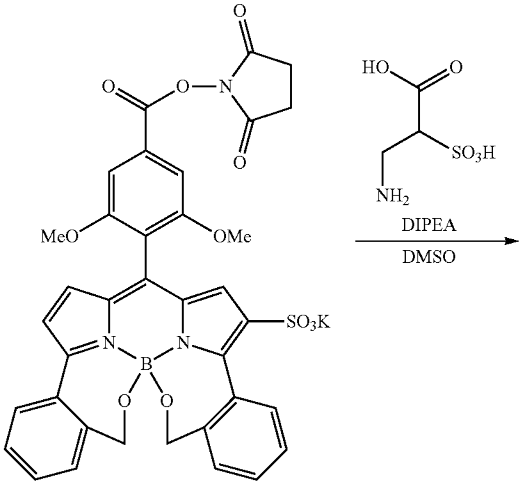

Compound (7-NHS)

-continued

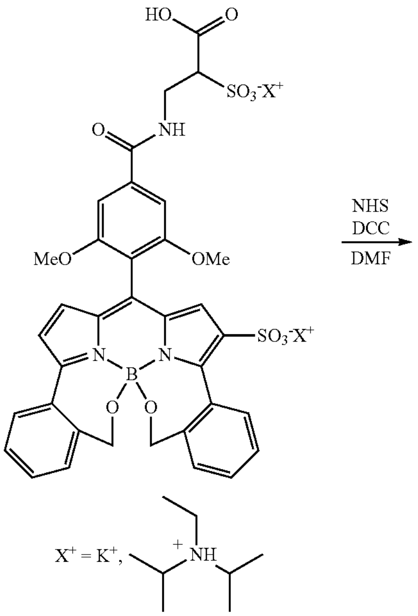

Compound (12)

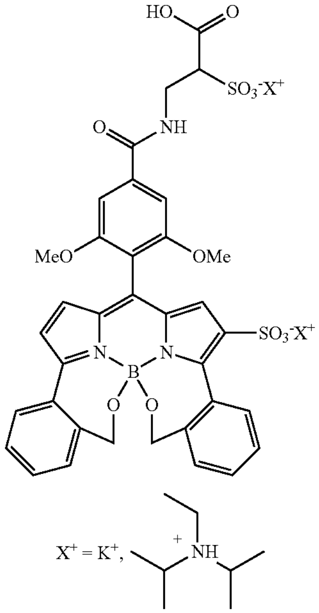

Compound (12)

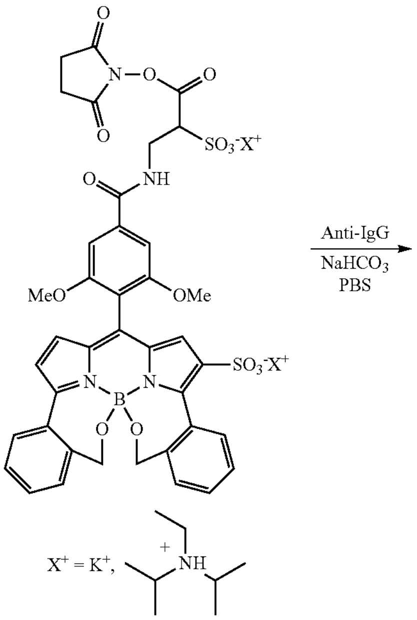

Compound (12-NHS)

-continued

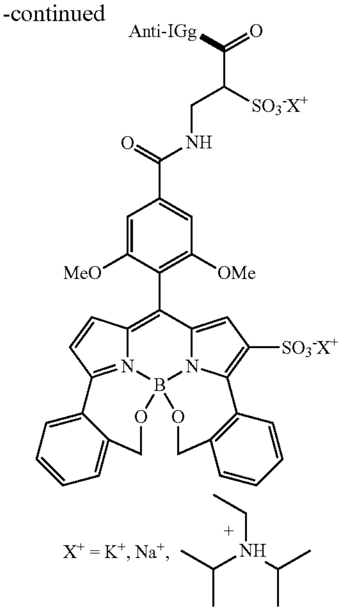

Labeled antibody (9)

2 mg of the compound (12) (reddish brown solid) was obtained in the same manner as in the method of synthesizing the compound (5), except that the compound (4-NHS) and γ-aminobutyric acid were respectively changed to the compound (7-NHS) and α-sulfo-β-alanine.

MS (ESI m/z): 776 (M−X+2H)

0.4 mg of the compound (12-NHS) (reddish brown solid) was obtained in the same manner as in the method of synthesizing the compound (4-NHS), except that the compound (4) was changed to the compound (12).

MS (ESI m/z): 873 (M−2X+3H)

The labeled antibody (9) was obtained in the same manner as in the method of synthesizing the labeled antibody (1), except that the compound (4-NHS) was changed to the compound (12-NHS).

Synthesis Example 13

A compound (13) and a labeled antibody (10) were synthesized based on the following schemes.

-continued

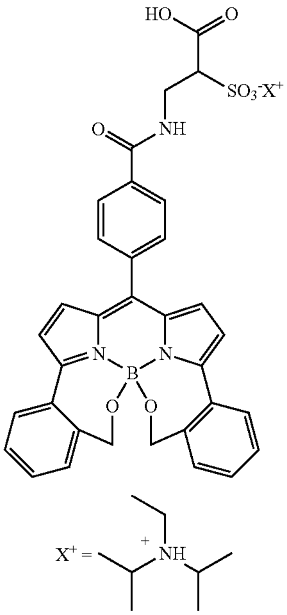

Compound (13)

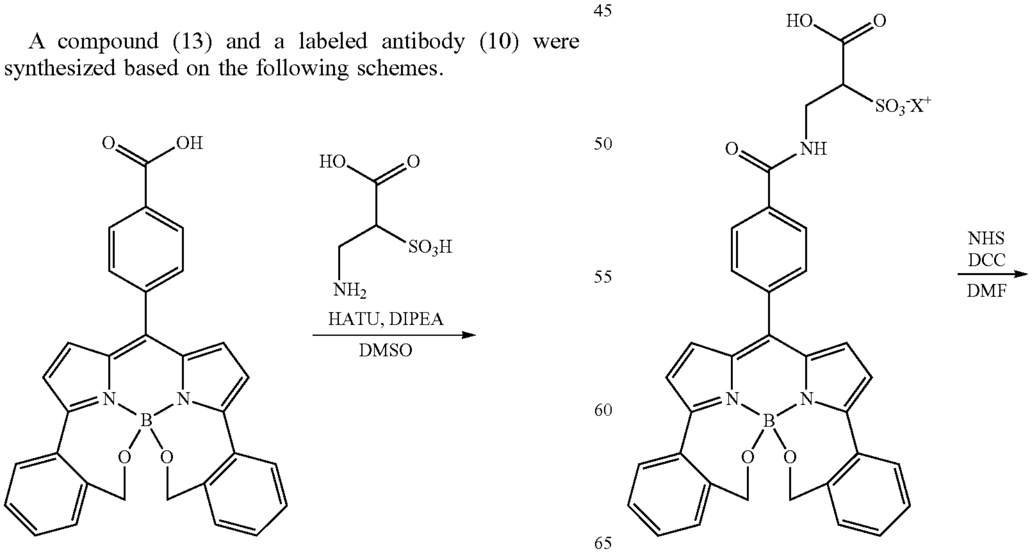

Compound (15)

Compound (13)

-continued

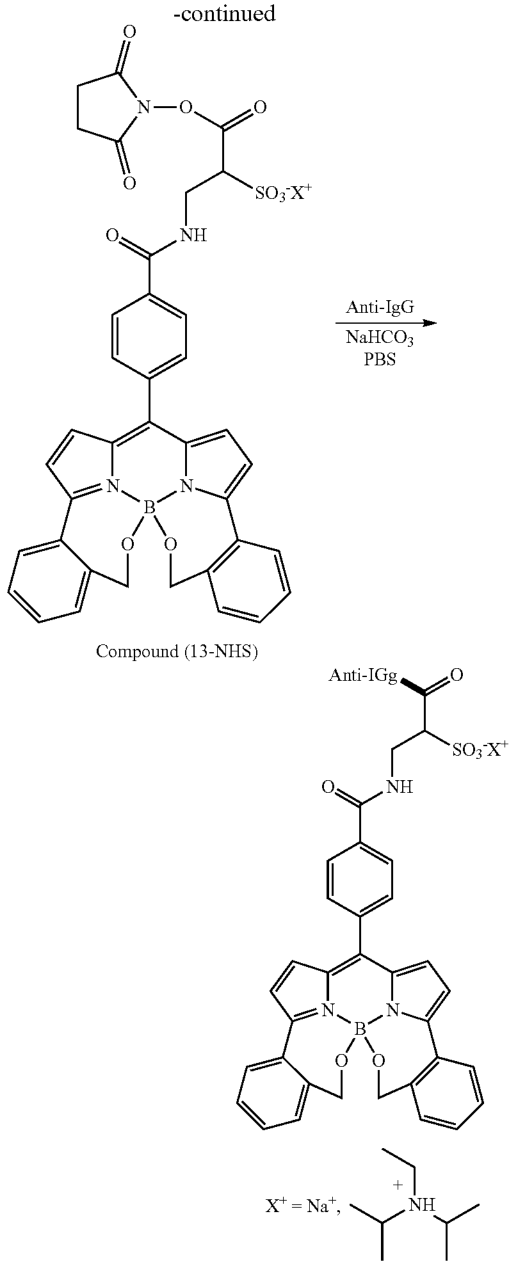

Compound (13-NHS)

$X^+ = Na^+$,

Labeled antibody (10)

To 40 μL of DMSO solution containing 3 mg of the compound (15), 5 mg of 1-[bis(dimethylamino)methylene]-1H-1,2,3-triazolo[4,5-b]pyridinium 3-oxide hexafluorophosphate [manufactured by FUJIFILM Wako Pure Chemical Corporation], 2 L of diisopropylethylamine [manufactured by FUJIFILM Wako Pure Chemical Corporation], 1 mg of α-sulfo-β-alanine [manufactured by FUJIFILM Wako Pure Chemical Corporation] were added, and the resultant mixture was stirred at room temperature for 12 hours. Subsequently, the reaction solution was directly purified by reverse-phase silica column chromatography [SNAP12 column Ultra C18, (manufactured by Biotage, LLC] (acetonitrile:water=0:100 to 20:80), and the fraction was collected and freeze-dried, thereby obtaining 2 mg of the compound (13) (reddish brown solid).

MS (ESI m/z): 776 (M−X+2H)

1 mg of the compound (13-NHS) (reddish brown solid) was obtained in the same manner as in the method of synthesizing the compound (4-NHS), except that the compound (4) was changed to the compound (13).

MS (ESI m/z): 733 (M−X+2H)

The labeled antibody (10) was obtained in the same manner as in the method of synthesizing the labeled antibody (1), except that the compound (4-NHS) was changed to the compound (13-NHS).

Synthesis Example 14

A compound (14) was synthesized based on the following scheme.

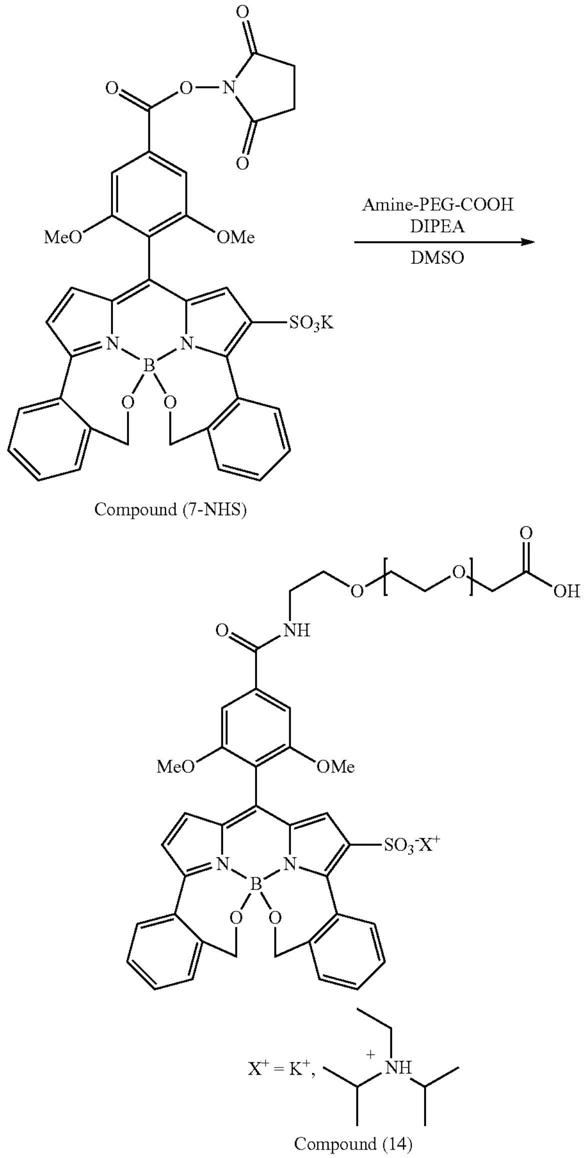

Compound (7-NHS)

$X^+ = K^+$,

Compound (14)

4 mg of the compound (14) (reddish brown oil) was obtained in the same manner as in the method of synthesizing the compound (5), except that the compound (4-NHS) and γ-aminobutyric acid were respectively changed to the compound (7-NHS) and (poly(ethylene glycol) 2-aminoethyl ether) acetic acid [number-average molecular weight=1,100, catalog number: 757861, manufactured by Sigma-Aldrich Co. LLC].

MS (ESI m/z): 1959 (M−X+2H), 1915 (M−X+2H), 1871 (M−X+2H), 1827 (M−X+2H), 1783 (M−X+2H), 1739 (M−X+2H).

(From left, n=28, 27, 26, 25, 24, 23)

Synthesis Example 15

A compound (15) was synthesized based on the following scheme.

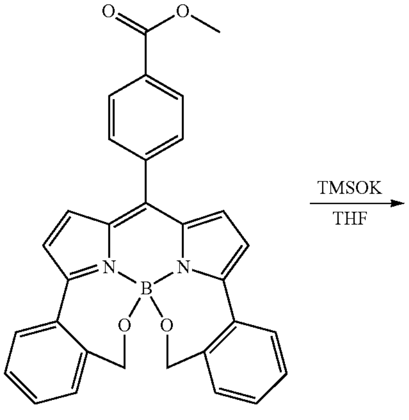

Compound (15-A)

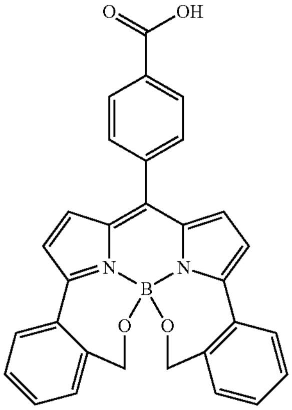

Compound (15)

The compound (15) was synthesized in the same manner as in the method of synthesizing the compound (4) from the compound (4-F), except that the compound (4-F) was changed to the compound (15-A).

MS (ESI m/z): 485 (M+H)

Synthesis Example 16

A compound (16) was synthesized based on the following scheme.

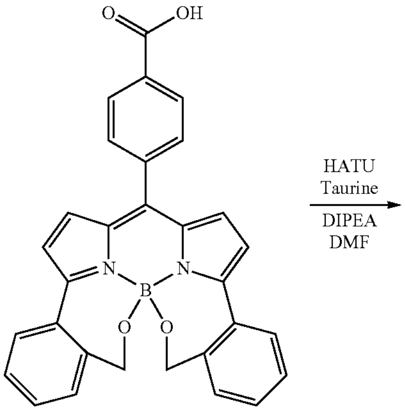

Compound (15)

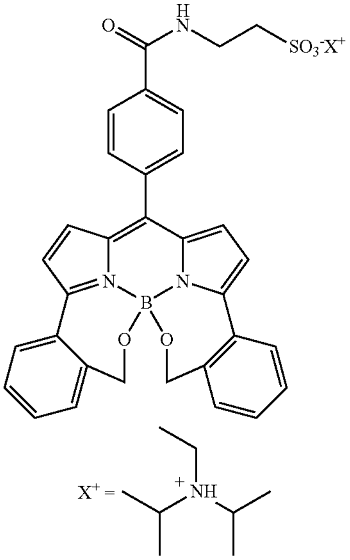

Compound (16)

8 mg of the compound (15), 6 mg of taurine, and 0.5 ml of DMF (extremely dehydrated) were put into a 50 ml eggplant-shaped flask, and stirring was performed in the nitrogen atmosphere. 14 mg of HATU and 14 μL of DIPEA were added thereto, and stirring was performed for a while at room temperature.

MS (ESI m/z): 592 (M−X+2H)

Synthesis Example 17

A compound (17) and a compound (18) were synthesized based on the following schemes.

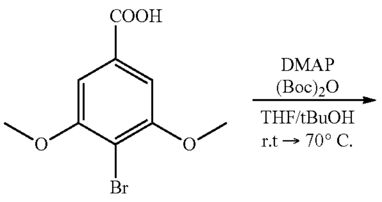

Compound (7-A)

-continued

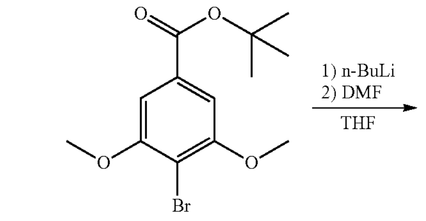

Compound (7-B)

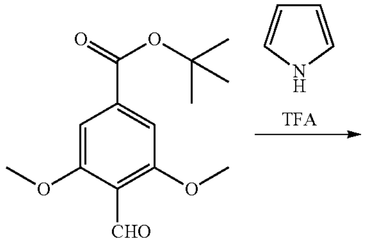

Compound (7-C)

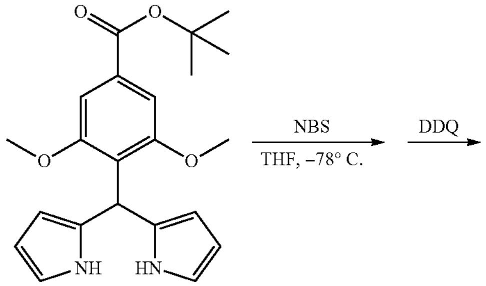

Compound (7-D)

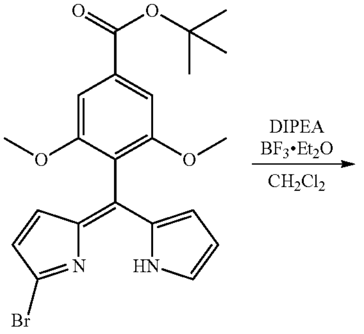

Compound (17-A)

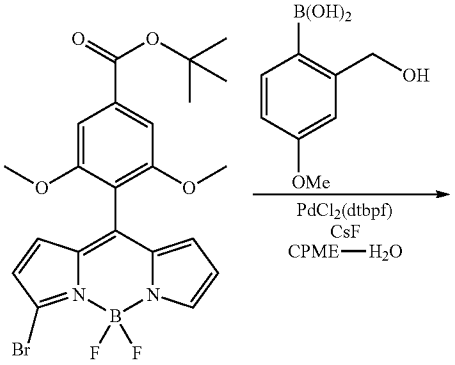

Compound (17-B)

-continued

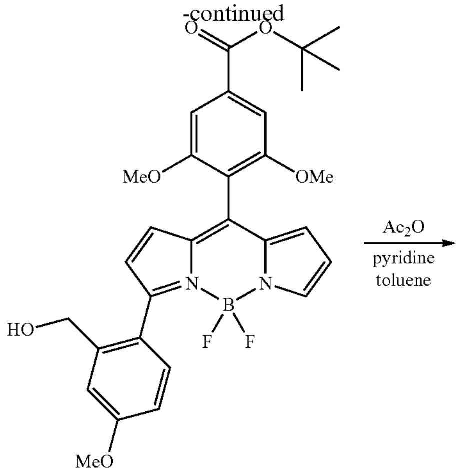

Compound (17-C)

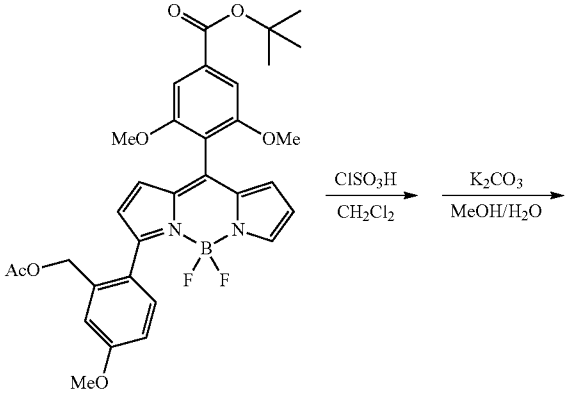

Compound (17-D)

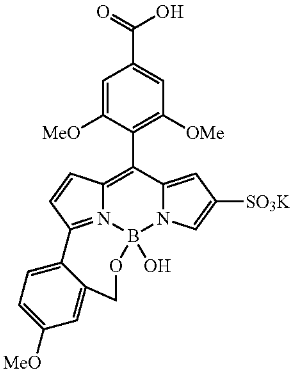

Compound (17)

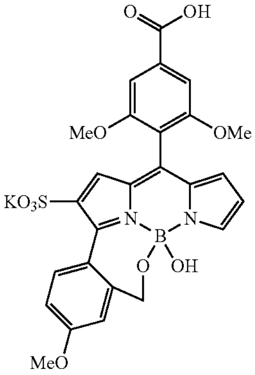

Compound (18)

The compound (17-A) was synthesized in the same manner as in the method of synthesizing the compound (7-E), except that equivalents of NBS and DDQ were respectively changed to the halves of those in the synthesis of the compound (7-E).

The compound (17) and the compound (18) were synthesized in the same manner as in the method of synthesizing the compound (7) from the compound (7-E), except that the compound (7-E) was changed to the compound (17-A) and equivalents of the reagents used until the synthesis of the compound (7) were respectively changed to the halves of those in the synthesis of the compound (7) from the compound (7-E).

MS (ESI m/z): 565 (M−K)

Synthesis Example 18
A compound (19) and a labeled antibody (11) were synthesized based on the following schemes.
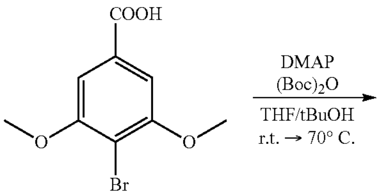
Compound (7-A)
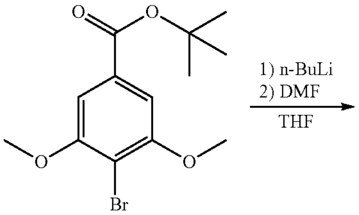
Compound (7-B)
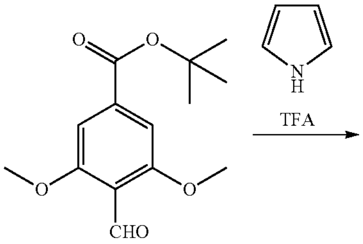
Compound (7-C)
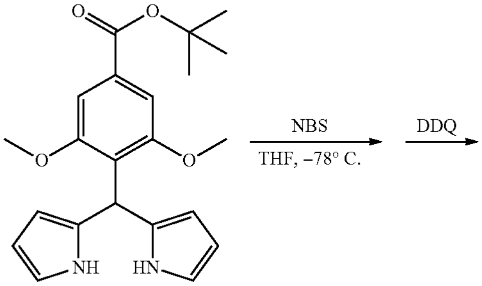
Compound (7-D)
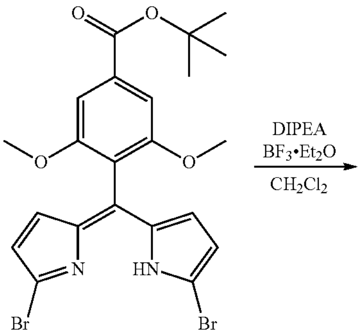
Compound (7-E)
-continued
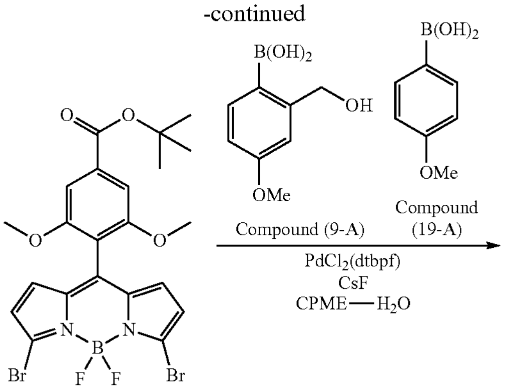
Compound (7-F)
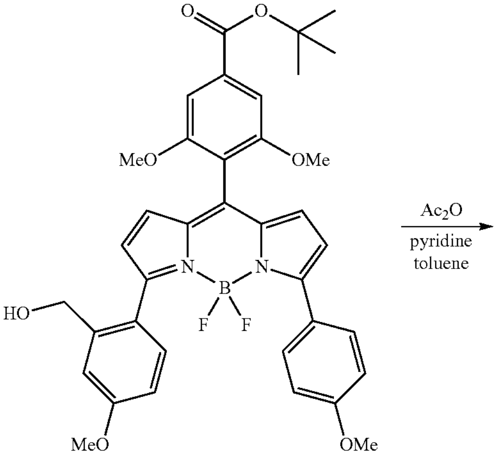
Compound (19-B)
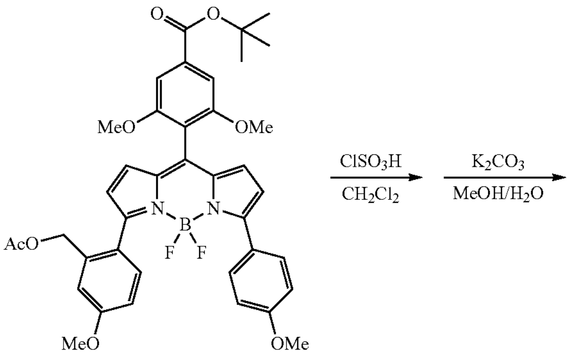
Compound (19-C)

-continued

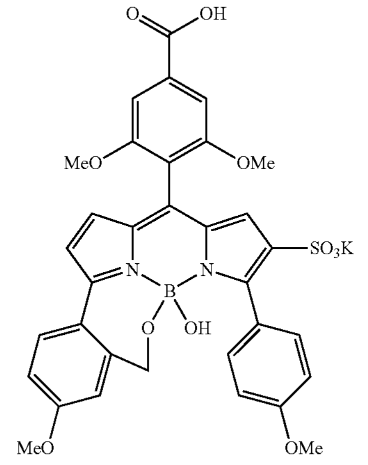

Compound (19)

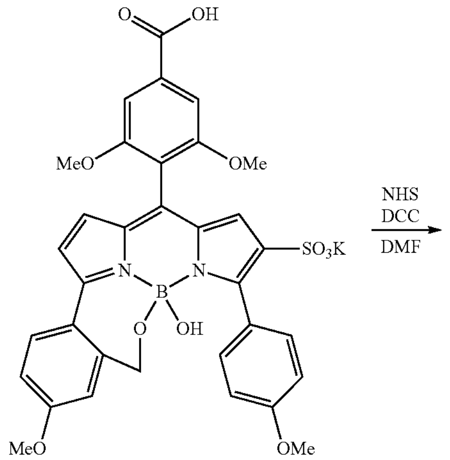

Compound (19)

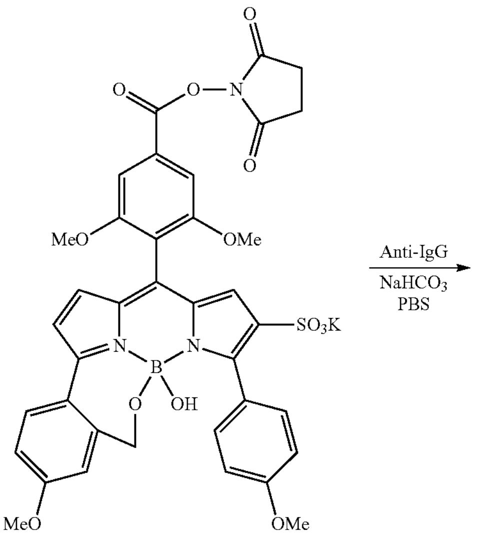

Compound (19-NHS)

-continued

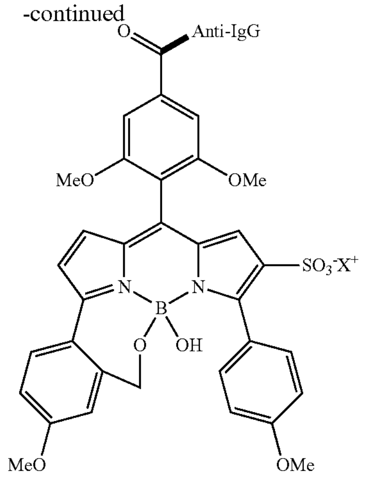

$X^+ = K^+, Na^+$

Labeled antibody (19)

The compound (19-B) was synthesized in the same manner as in the method of synthesizing the compound (7-G) from compound (7-F), except that the half equivalent of the compound (9-A) and the half equivalent of the compound (19-A) were used instead of o-(hydroxymethyl)phenylboronic acid.

The compound (19) was synthesized in the same manner as in the method of synthesizing the compound (7) from the compound (7-G), except that the compound (19-B) was used instead of the compound (7-G).

MS (ESI m/z): 671 (M−K)

0.4 mg of the compound (19-NHS) (reddish brown solid) was obtained in the same manner as in the method of synthesizing the compound (4-NHS), except that the compound (4) was changed to the compound (19).

MS (ESI m/z): 768 (M−1)

The labeled antibody (11) was obtained in the same manner as in the method of synthesizing the labeled antibody (1), except that the compound (4-NHS) was changed to the compound (19-NHS).

Synthesis Example 19

A compound (20) was synthesized based on the following scheme.

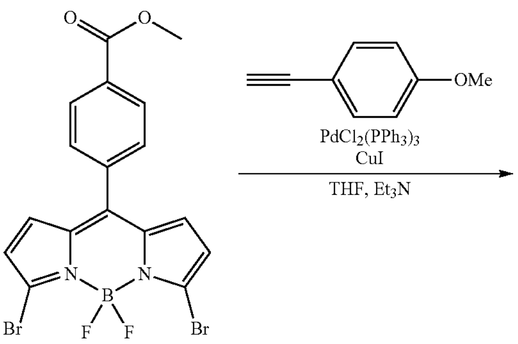

Compound (4-C)

-continued
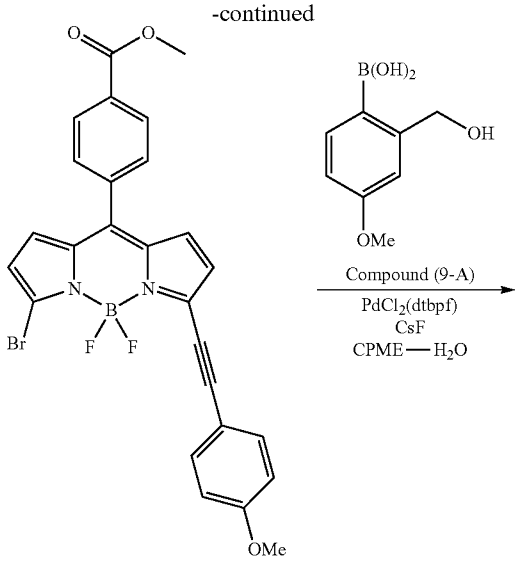
Compound (20-A)
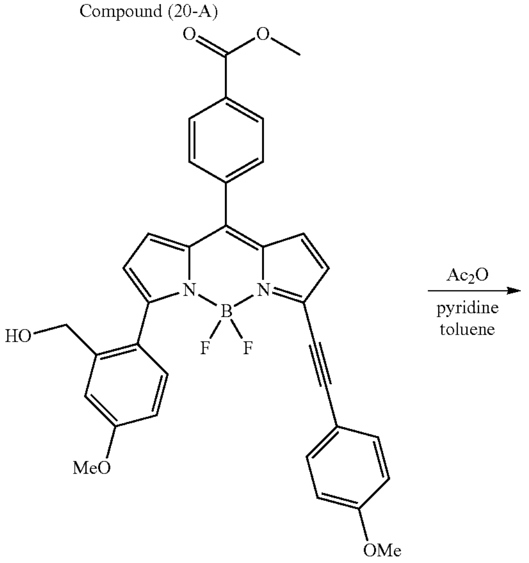
Compound (20-B)
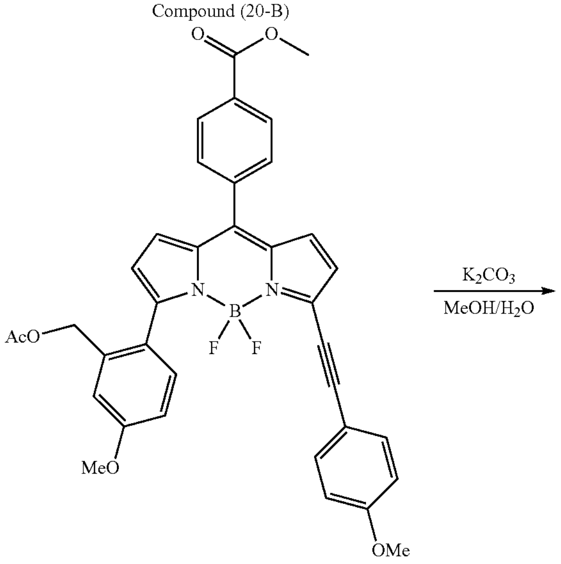
Compound (20-C)
-continued
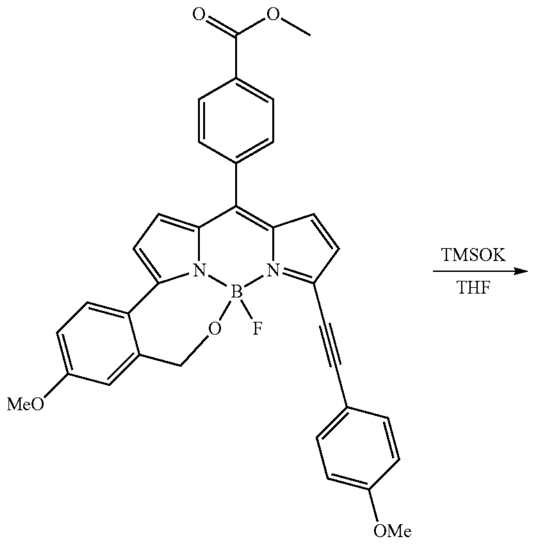
Compound (20-D)
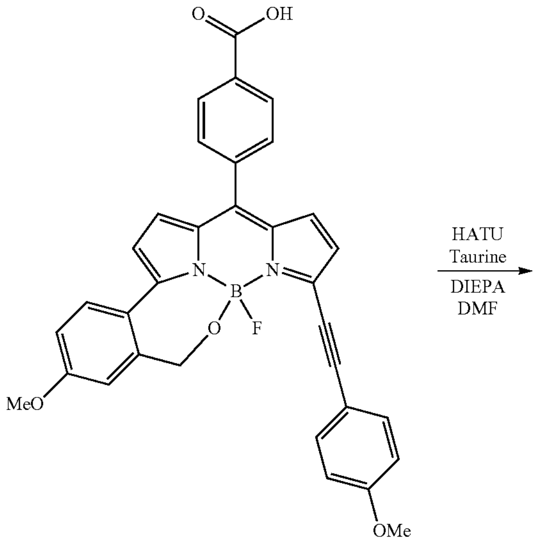
Compound (20-E)

-continued

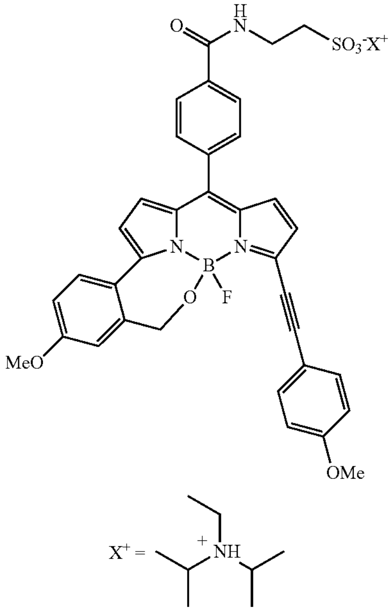

Compound (20)

0.5 g of the compound (4-C), 25 ml of THF, 2 ml of triethylamine, 0.137 g of ethynylanisole, 7 mg of copper iodide, and 11 mg of dichlorobis(triphenylphosphine) palladium (II) were put into a 100 ml three-necked flask and subjected to nitrogen purge, and then the reaction was performed at an external temperature of 75° C. for 1 hour. After the reaction, the solvent was removed by evaporation, the reaction product was purified by silica gel column chromatography using ethylacetate/hexane=0/100 to 50/50 as an eluent to obtain 0.40 g of the compound (20-A).

The compound (20-C) was synthesized in the same manner as in the method of synthesizing the compound (15), except that the compound (15-A) was replaced with the compound (20-B).

The compound (20-D) was synthesized in the same manner as in the method of synthesizing the compound (7-H) from the compound (7-F), except that the compound (7-F) was replaced with the compound (20-A). The compound (20) was synthesized by replacing the compound (15-A) with the compound (20-D) in the method of synthesizing compound (16) from compound (15-A).

MS (ESI m/z): 664 (M−X)

Synthesis Example 20

A compound (21) was synthesized based on the following scheme.

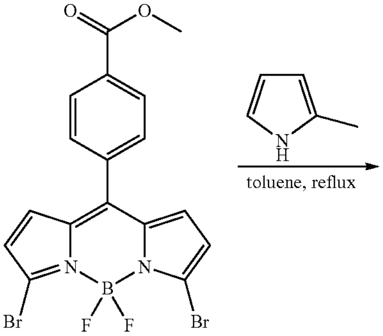

Compound (4-C)

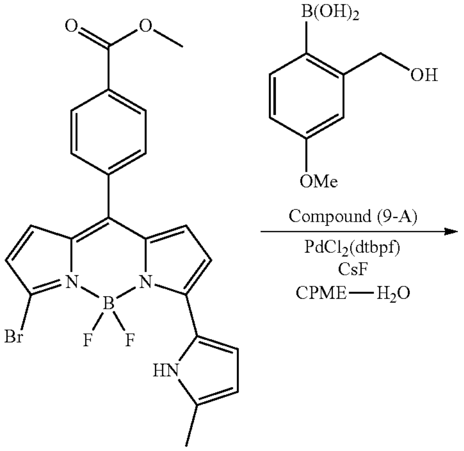

Compound (21-A)

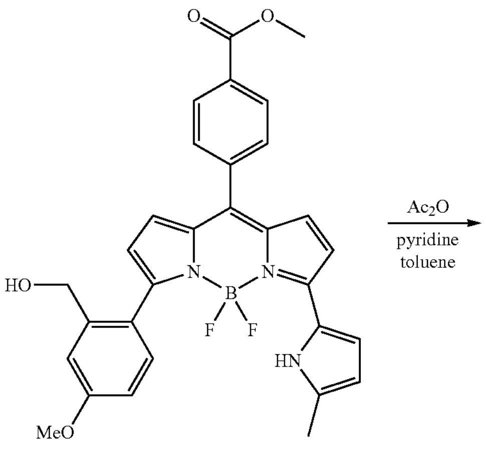

Compound (21-B)

-continued

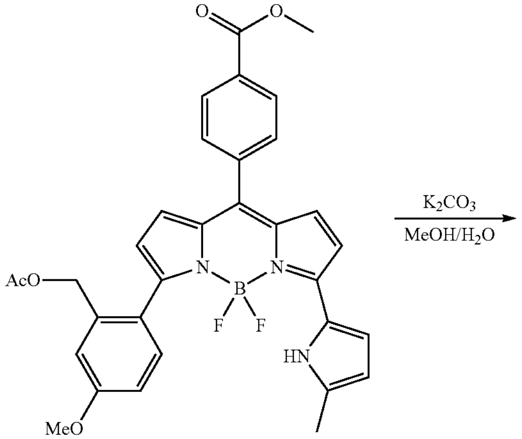

Compound (21-B)

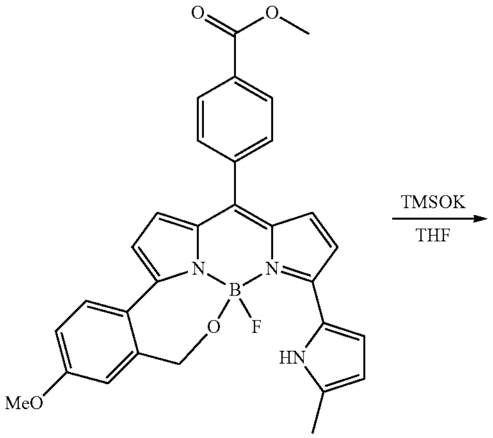

Compound (21-C)

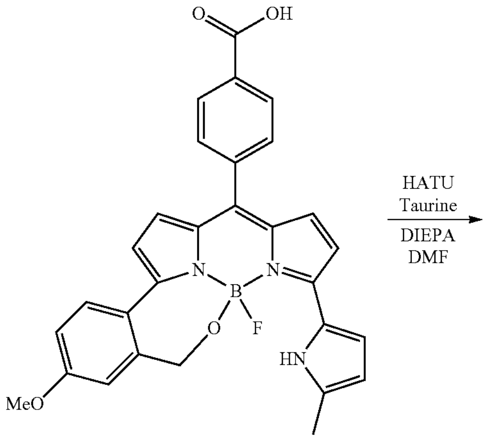

Compound (21-D)

-continued

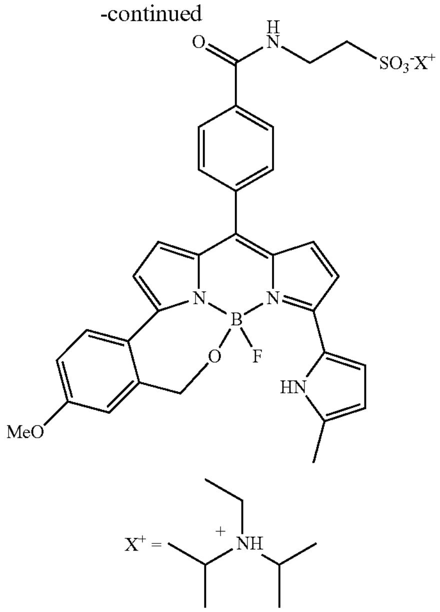

Compound (21)

0.5 g of the compound (4-C), 0.126 g of 2-methyl-1H-pyrrole, and 5 ml of toluene were put into a 100 ml three-necked flask and subjected to nitrogen purge, the resultant mixture was reacted at an external temperature of 130° C. for 2.5 hours. After returning to room temperature, the reaction product was purified by silica gel column chromatography using ethyl acetate/hexane=0/100 to 50/50 as an eluent to obtain 0.30 g of the compound (21-A).

The compound (21) was synthesized in the same manner as in the method of synthesizing the compound (20), except that the compound (20-A) was replaced with the compound (21-A).

MS (ESI m/z): 613 (M−X)

Synthesis Example 21

A compound (22) was synthesized based on the following scheme.

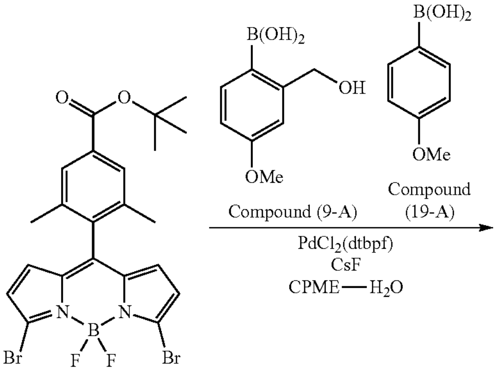

Compound (10-E)

-continued

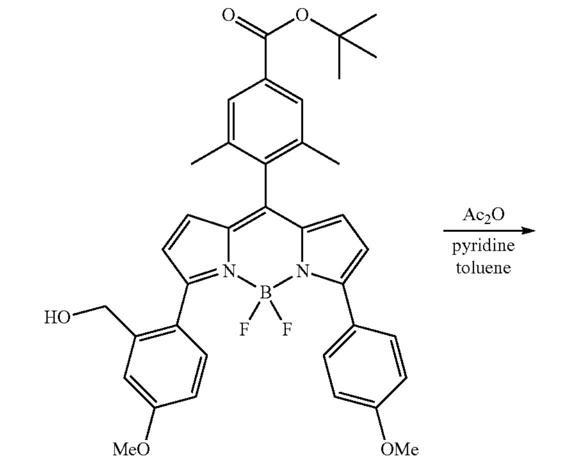

Compound (22-D)

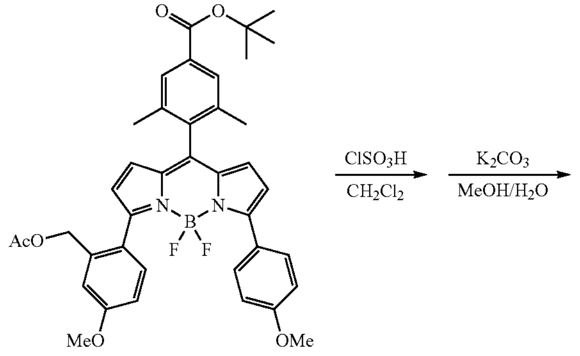

Compound (22-E)

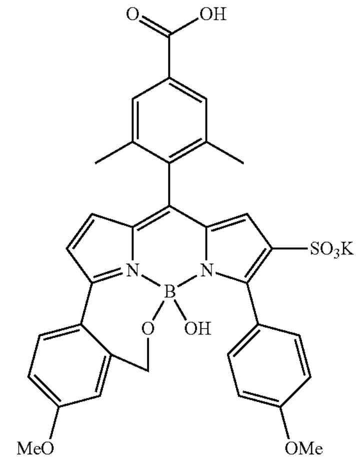

Compound (22)

The compound (22) was synthesized in the same manner as in the method for synthesizing the compound (19) from the compound (7-F), except that the compound (10-E) was used instead of the compound (7-F).

MS (ESI m/z): 639 (M−K)

Synthesis Example 22

A compound (23) was synthesized based on the following scheme.

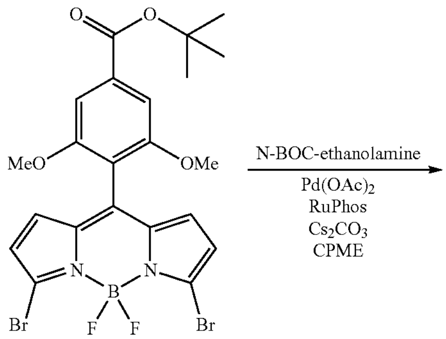

Compound (7-F)

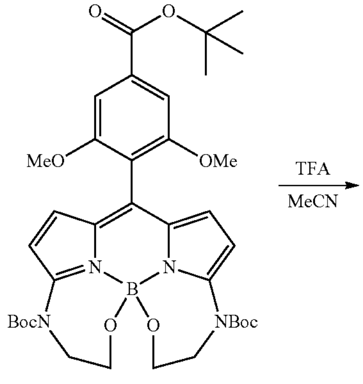

Compound (23-A)

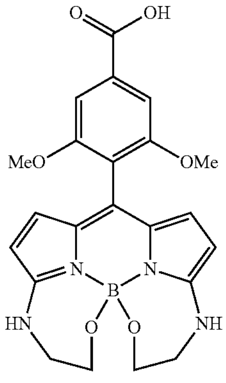

Compound (23)

29 mg of the compound (7-F), 26 mg of N-BOC-ethanolamine [manufactured by FUJIFILM Wako Pure Chemical Corporation], 9 mg of RuPhos [manufactured by Sigma-Aldrich Co. LLC], 2 mg of palladium acetate [manufactured by FUJIFILM Wako Pure Chemical Corporation], 65 mg of cesium carbonate [manufactured by FUJIFILM Wako Pure Chemical Corporation], and 0.5 ml of cyclopentyl methyl ether [manufactured by FUJIFILM Wako Pure Chemical Corporation] were added in a 2 ml pressure resistance test tube, and the resultant mixture was stirred with heating in a microwave reactor [manufactured by Biotage, LLC] at 120° C. for 20 minutes. The reaction solution was purified by preparative thin layer silica gel column chromatography (ethyl acetate/hexane=50/50), extracted with ethyl acetate, and then the solvent was removed by evaporation under reduced pressure, thereby obtaining 0.3 mg of the compound (23-A).

MS (ESI m/z): 707 (M+K)

0.3 mg of the compound (23-A), 0.02 ml of trifluoroacetic acid [manufactured by FUJIFILM Wako Pure Chemical Corporation], and 0.02 ml of acetonitrile [manufactured by FUJIFILM Wako Pure Chemical Corporation] were added in a 5 ml eggplant-shaped flask, and the resultant mixture was stirred at room temperature for 5 minutes. The reaction solution was purified by preparative thin layer silica gel column chromatography (chloroform/methanol=80/20), extracted with ethyl acetate, and then the solvent was removed by evaporation under reduced pressure, thereby obtaining the compound (23) (weighing was impossible due to the extremely small amount of the obtained compound).

MS (ESI m/z): 451 (M+K)

Synthesis Example 23

A compound (24) and a labeled antibody (12) were synthesized based on the following schemes.

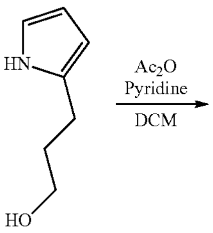

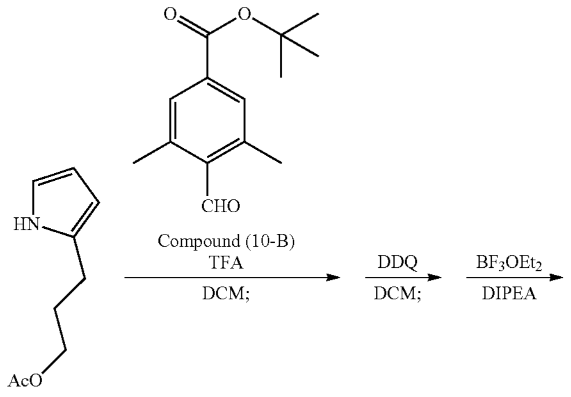

Compound (10-B)

Compound (24-A)

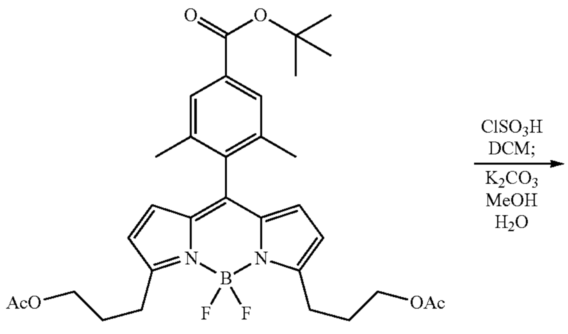

Compound (24-B)

-continued

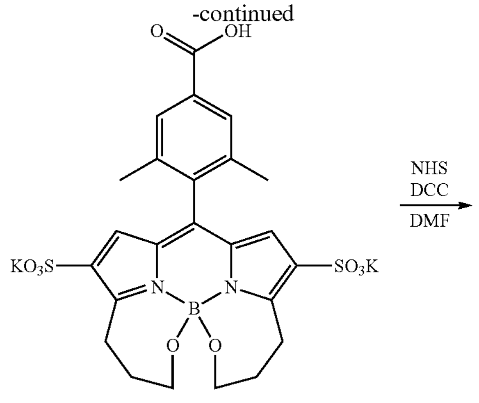

Compound (24)

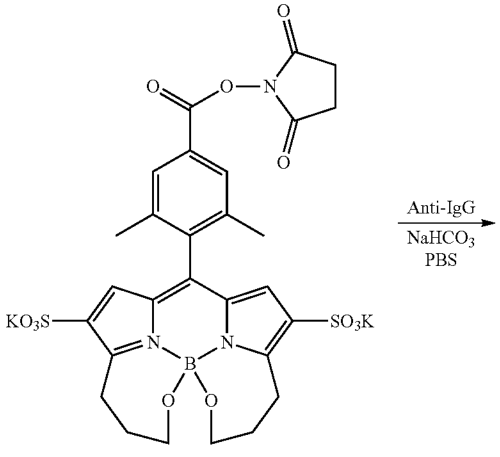

Compound (24-NHS)

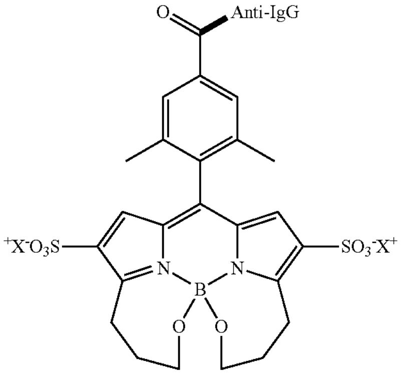

$X = K^+, Na^+$

Labeled antibody (12)

0.93 g of 3-(1H-pyrrol-2-yl)propan-1-ol [manufactured by Enamine Ltd.], 0.77 ml of acetic anhydride [manufactured by FUJIFILM Wako Pure Chemical Corporation], 0.72 ml of pyridine [manufactured by FUJIFILM Wako Pure Chemical Corporation], and 7.4 ml of methylene chloride [manufactured by FUJIFILM Wako Pure Chemical Corporation] were added in a 50 ml eggplant-shaped flask, and the resultant mixture was stirred at room temperature for 1 hour. The reaction solution was purified by silica gel column chromatography (ethyl acetate/hexane=0/100 to 20/80), and the solvent was removed by evaporation under reduced pressure, thereby obtaining 0.63 g of a milky white solid of the compound (24-A).

MS (ESI m/z): 168 (M+K)

264 mg of the compound (24-A), 148 mg of the compound (10-B), 0.005 ml of trifluoroacetic acid [manufactured by FUJIFILM Wako Pure Chemical Corporation], and 0.63 ml of methylene chloride [manufactured by FUJIFILM Wako Pure Chemical Corporation] were added in a 50 ml eggplant flask, and the resultant mixture was stirred at room temperature for 10 minutes. Subsequently, the reaction solution was cooled to 0 C and diluted with 5.7 ml of methylene chloride [manufactured by FUJIFILM Wako Pure Chemical Corporation], 229 mg of 2,3-dichloro-5,6-dicyano-p-benzoquinone [manufactured by FUJIFILM Wako Pure Chemical Corporation] was added thereto, and the resultant mixture was stirred at 0° C. for 15 minutes. Subsequently, 0.87 ml of a trifluoroborane-diethyl ether complex [manufactured by FUJIFILM Wako Pure Chemical Corporation] and 0.77 ml of diisopropylethylamine [manufactured by FUJIFILM Wako Pure Chemical Corporation] were added thereto, and the resultant mixture was stirred at room temperature for 10 minutes. After adding saturated aqueous sodium hydrogen carbonate, the mixture was extracted 4 times with methylene chloride, and the solvent was removed by evaporation under reduced pressure. The residue was purified by silica gel column chromatography (ethyl acetate/hexane=0/100 to 20/80), and the solvent was removed by evaporation under reduced pressure to obtain 226 mg of the compound (24-B).

MS (ESI m/z): 595 (M−K)

10 mg of the compound (24-B) and 1.4 ml of methylene chloride [manufactured by FUJIFILM Wako Pure Chemical Corporation] were added in a 5 mL pressure resistance test tube, and after cooling to 0° C., 0.006 ml of chlorosulfonic acid [manufactured by FUJIFILM Wako Pure Chemical Corporation] was added thereto, followed by stirring at 0° C. for 15 minutes. Subsequently, 20 mg of potassium carbonate [manufactured by FUJIFILM Wako Pure Chemical Corporation] and 0.7 ml of distilled water were added thereto, and only methylene chloride was removed by evaporation under reduced pressure. 0.1 ml of methanol [manufactured by FUJIFILM Wako Pure Chemical Corporation] was added to the reaction solution, and the resultant mixture was stirred with heating at 80° C. for 10 minutes in a microwave reactor [manufactured by Biotage, LLC]. The reaction solution was purified by reverse-phase silica gel column chromatography [SNAP12 column Ultra C18, (manufactured by Biotage, LLC] (acetonitrile:water=0:100), the solvent was removed by freeze-drying, thereby obtaining 1 mg of an orange solid of the compound (24).

MS (ESI m/z): 575 (M−K)

10 mg of the compound (24-NHS) (orange solid) was obtained in the same manner as in the method of synthesizing the compound (4-NHS), except that the compound (4) was changed to the compound (24).

MS (ESI m/z): 672 (M−K)

The labeled antibody (12) was obtained in the same manner as in the method of synthesizing the labeled antibody (1), except that the compound (4-NHS) was changed to the compound (24-NHS).

Although not particularly described in the compounds of Examples, the sulfo group and the carboxy group include a salt structure (for example, a potassium salt, a sodium salt, or a DIPEA salt).

<Example 1> Evaluation of Water Solubility and Light Resistance of Compound

The following characteristics were evaluated for the compounds synthesized above and the comparative compounds, and the results are shown in Table 1.

[Evaluation of Water Solubility]

5 μL of a DMSO solution (20 mM in dimethylsulfoxide (DMSO), an evaluation sample solution) containing the compound synthesized above and 495 μL of phosphate buffered saline (hereinafter, also referred to as "PBS solution") having a pH of 7.4 were added in a 1.5 mL Eppendorf tube and mixed, and the resultant mixture was stirred at 2,000 rpm for 30 minutes using Multi-shaker MS300 (trade name, manufactured by AS ONE Corporation). The mixed solution was allowed to be left for 60 minutes in the light-shielded conditions and then subjected to centrifugal precipitation (12,000 rpm, 5 minutes). The compound concentration (in a case where the whole compound is dissolved, the compound concentration is 200 μM) of the filtrate obtained by filtrating with a 0.20 m filter was measured using UHPLC Nexera [Shim-pack XR-ODSII, manufactured by Shimadzu Corporation]. The water solubility was evaluated based on the following evaluation criteria.

In the present test, it is determined that a compound has passed the evaluation of the water solubility in a case where the compound has a rank "B" or higher.

—Evaluation Criteria for Water Solubility—

A: 100 μM or more

B: 1 μM or more and less than 100 μM

C: 0.1 μM or more and less than 1 μM

D: Concentration measurement is impossible due to low water solubility

[Evaluation of Light Resistance]

The compound synthesized above was dissolved in a PBS solution (pH 7.4) so that the absorbance at the absorption peak wavelength was 0.095 to 0.105. In a state where this solution was exposed using a merry-go-round type light irradiation apparatus (xenon lamp UXL-500D-O manufactured by Ushio Inc., HA-50 filter, Y44 filter, exposure intensity: 22 mW/cm$^2$ (in terms of 500 nm)), the absorbance at the absorption peak wavelength of each compound was measured over time with a spectrometer (Agilent 8453, manufactured by Agilent Technologies). The absorbance at the absorption peak wavelength before exposure was set to 100% and the exposure time until the absorbance at this absorption peak wavelength decreases by 20% (absorbance at the absorption peak wavelength reaches 80%) was measured. The results were evaluated based on the following evaluation criteria.

In the present test, it is determined that a compound has passed the evaluation of the light resistance in a case where the compound has a rank "C" or higher.

—Evaluation Criteria for Light Resistance—

A: 100 hours or more

B: 50 hours or more and less than 100 hours

C: 25 hours or more and less than 50 hours

D: 2 hours or more and less than 25 hours

E: less than 2 hours

F: Evaluation is impossible due to low water solubility

TABLE 1

| | Name of fluorescent compound | Water solubility | Light resistance |
|---|---|---|---|
| Example 1-1 | Compound (1) | A | B |
| Example 1-2 | Compound (2) | A | A |
| Example 1-3 | Compound (3) | A | C |
| Example 1-4 | Compound (4) | A | A |
| Example 1-5 | Compound (5) | A | A |
| Example 1-6 | Compound (6) | A | A |
| Example 1-7 | Compound (7) | A | A |

TABLE 1-continued

| | Name of fluorescent compound | Water solubility | Light resistance |
|---|---|---|---|
| Example 1-8 | Compound (8) | A | A |
| Example 1-9 | Compound (9) | A | B |
| Example 1-10 | Compound (10) | A | A |
| Example 1-11 | Compound (11) | A | B |
| Example 1-12 | Compound (12) | A | A |
| Example 1-13 | Compound (13) | A | B |
| Example 1-14 | Compound (14) | A | A |
| Example 1-15 | Compound (16) | B | C |
| Example 1-16 | Compound (17) | A | C |
| Example 1-17 | Compound (18) | A | C |
| Example 1-18 | Compound (19) | A | C |
| Example 1-19 | Compound (20) | B | C |
| Example 1-20 | Compound (21) | B | B |
| Example 1-21 | Compound (24) | A | C |
| Comparative Example 1-1 | Comparative compound (1) | D | F |
| Comparative Example 1-2 | Comparative compound (2) | A | E |

From the results in Table 1 above, it can be seen that the fluorescent compound according to the embodiment of the present invention, which is represented by Formula (1) or Formula (4), has excellent water solubility and also excellent light resistance. Among them, compounds (1), (2) and (4) to (14) are excellent since they show evaluation A in water solubility and evaluation A or B in light resistance.

Further, it can be seen that in comparison with the comparative compound (1), the hydrophilic group included in the fluorescent compound according to the embodiment of the present invention not only enhances the hydrophilicity of the compound but also contributes to the improvement of light resistance. In this respect, compounds (4) to (14) are more preferable.

As described above, the fluorescent compound according to the embodiment of the present invention is a compound that realizes both sufficient hydrophilicity and excellent light resistance, which is suitable as a fluorescent dye for in vivo fluorescence imaging.

<Example 2> Evaluation of Water Solubility and Light Resistance of Labeled Antibody The labeled antibodies synthesized above were evaluated for both water solubility and light resistance, and the results are shown in Table 2.

The water solubility and the light resistance were evaluated in the same manner as in the evaluation of the water solubility and the light resistance in Example 1, except that the labeled antibody was used instead of the compound. However, with respect to the light resistance in Example 2, it is determined that a labeled antibody has passed the evaluation of the light resistance in a case where the labeled antibody has a rank "D" or higher.

TABLE 2

| | Name of fluorescent labeled antibody | Water solubility | Light resistance |
|---|---|---|---|
| Example 2-1 | Labeled antibody (1) | A | D |
| Example 2-2 | Labeled antibody (2) | A | D |
| Example 2-3 | Labeled antibody (3) | A | D |
| Example 2-4 | Labeled antibody (4) | A | C |
| Example 2-5 | Labeled antibody (5) | A | D |
| Example 2-6 | Labeled antibody (6) | A | C |
| Example 2-7 | Labeled antibody (7) | A | B |
| Example 2-8 | Labeled antibody (8) | A | C |

TABLE 2-continued

| | Name of fluorescent labeled antibody | Water solubility | Light resistance |
|---|---|---|---|
| Example 2-9 | Labeled antibody (9) | A | B |
| Example 2-10 | Labeled antibody (10) | A | C |
| Reference Example 2-1 | Reference labeled antibody (1) | A | D |

<Note for Table>
The reference labeled antibody (1) is Alexa Fluor (registered trademark) 568-labeled anti-mouse IgG antibody (manufactured by Abcam plc., trade name). In addition, Alexa Fluor 568 in this labeled antibody is presumed to be a fluorescent dye having the following chemical structure. In the following structural formula, * indicates a bonding portion with the anti-mouse IgG antibody.

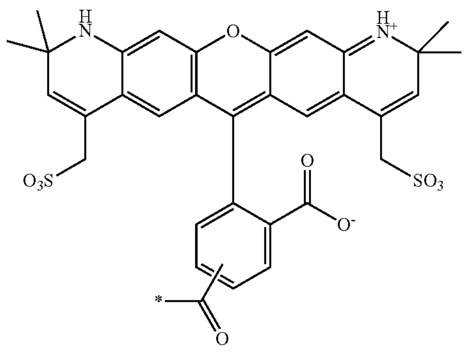

Alexa Fluor 568

From the results in Table 2 above, it can be seen that the labeled antibody according to the embodiment of the present invention, which is obtained from the fluorescent compound according to the embodiment of the present invention, which is represented by Formula (1) or Formula (4), has excellent water solubility and also excellent light resistance. Concretely, labeled antibodies obtained from the compounds (4) to (13) are excellent in water solubility and light resistance. In particular, labeled antibodies showing evaluation A in water solubility and evaluation C or more in light resistance, which are obtained from compounds (7) and (9) to (13), are preferable.

As described above, the fluorescent labeled biological substance according to the embodiment of the present invention realizes both sufficient hydrophilicity and excellent light resistance, and is suitable as a labeled biological substance, for example, for in vivo fluorescence imaging of a living body, requiring a long-term or high-resolution observation.

<Example 3> Evaluation of Light Resistance of Labeled Antibody in Stained Cells

Cell staining was carried out as follows using the labeled antibody and the comparative labeled antibody synthesized as described above. The following characteristics were evaluated for the prepared stained cells, and the results are shown in Table 3.

[Preparation of Stained Cell Sample]

NCI-H460 cells (catalog number: HTB-177TM, obtained from ATCC) were seeded on a chamber slide and were cultured in RPMI-1640 medium containing 10% fetal calf serum and 1% penicillin/streptomycin (both manufactured by Thermo Fisher Scientific, Inc.) in an incubator for 3 days.

Subsequently, the medium was removed, and the cells were treated with a 4% paraformaldehyde solution for 20 minutes for fixation. Then the fixed cells were washed with PBS [manufactured by Thermo Fisher Scientific, Inc.], treated with a PBS solution containing 0.5% of concentration of Triton X-100 (Polyethylene Glycol Mono-p-isooctylphenyl Ether) for 10 minutes, and then washed with PBS. Subsequently, the washed cells were added in an aqueous solution containing bovine serum albumin (BSA) at a concentration of 1% and treated for 30 minutes. Then, the cells were treated with a diluted solution of an anti-α-Tubulin antibody (mouse monoclonal, catalog number: 017-25031, manufactured by FUJIFILM Wako Pure Chemical Corporation) as a primary antibody at a final antibody concentration of 0.5 g/mL and allowed to be left at room temperature for 1 hour. After washing with PBS, the cells were treated with the aqueous solution containing 10 μg/mL of each labeled antibody as a secondary antibody, allowed to be left at room temperature for 1 hour while being shielded from light, and washed again with PBS to obtain each stained cell sample.

Immediately after the preparation of the stained cell sample, the following evaluation of light resistance was performed.

[Evaluation of Light Resistance in Stained Cells]

Each stained cell sample was placed under a confocal laser microscope [TCS SP5, manufactured by Leica Microsystems], and a time-lapse measurement was performed for 4 hours with a He—Ne laser (output: 100%) as a light source at a wavelength of 543 nm and a detection wavelength of 554 to 773 nm. The time-lapse profiles of the fluorescence intensities at the four stained and four unstained areas were acquired and the average signal intensity of the unstained areas was subtracted from the average signal intensity of the stained areas to take the resultant difference as the net fluorescence intensity. The fluorescence intensity before exposure was set to 100% and the exposure time until the absorbance decreases by 20% (absorbance reaches 80%) was measured. The results were evaluated based on the following evaluation criteria.

—Evaluation Criteria for Light Resistance—

A: 4 hours or more

B: 3 hours or more and less than 4 hours

C: 2 hours or more and less than 3 hours

D: 1 hour or more and less than 2 hours

E: less than 1 hour

TABLE 3

| | Name of fluorescent labeled antibody | Light resistance in stained cells |
|---|---|---|
| Example 3-1 | Labeled antibody (4) | C |
| Example 3-2 | Labeled antibody (6) | A |
| Example 3-3 | Labeled antibody (8) | A |
| Example 3-4 | Labeled antibody (10) | C |
| Reference Example 3-1 | Reference labeled antibody (1) | D |

From the results of Table 3, it can be seen that, as compared with the stained cells prepared using the reference labeled antibody (1), the stained cells prepared using the antibody labeled with the fluorescent compound according to the embodiment of the present invention, which is represented by Formula (1) or Formula (4), exhibit excellent light resistance. Concretely, labeled antibodies obtained from the compounds (4) to (13) are excellent in water solubility and light resistance. Further, labeled antibodies showing evaluation A in water solubility and evaluation C or more in light resistance, which are obtained from the compounds (7) and (9) to (13), are preferable. Among them, labeled antibodies showing evaluation A in water solubility and evaluation C in light resistance, which are obtained from compounds (4), (6), (8) and (10), are excellent in light resistance when used for staining cells.

As described above, the light resistance which has been a drawback of the compounds having a conventional dipyrromethene boron complex structure can be improved and the versatility as a fluorescent dye for the in vivo imaging or detection of the biological substance can be greatly improved in the fluorescent labeled biological substance using the fluorescent compound according to the embodiment of the present invention.

The present invention has been described together with the embodiments of the present invention. However, the inventors of the present invention do not intend to limit the present invention in any part of the details of the description unless otherwise specified, and it is considered that the present invention should be broadly construed without departing from the spirit and scope of the invention shown in the attached "WHAT IS CLAIMED IS". For example, when it is possible to combine/replace a plurality of embodiments, to the extent that a person skilled in the art can directly and unambiguously determine, such a combination or replacement can be done.

What is claimed is:

1. A fluorescent compound represented by Formula (1) or Formula (4),

Formula (1)

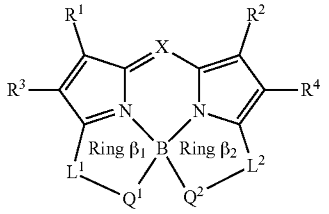

Formula (4)

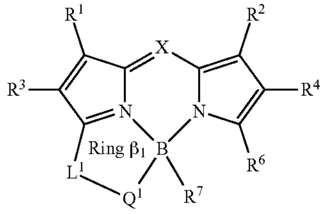

in the formula, X represents $CR^5$ or N, $R^1$ to $R^6$ represent a halogen atom, a cyano group, or a group represented by Formula (A), $R^7$ represents an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, or a halogen atom, where $R^6$ and $R^7$ do not bond to each other to form a ring, $Q^1$ and $Q^2$ represent a group represented by any one of Formulae (1-1) to (1-3), $L^1$ and $L^2$ represent an alkylene group, an alkenylene group, an arylene group, a heteroarylene group, a cycloalkylene group, a cycloalkenylene group, a divalent aliphatic heterocyclic group, or a group represented by any one of Formulae (1-1) to (1-8), or a linking group formed by combining two to four of these groups, and a ring $\beta_1$ and a ring $\beta_2$ are a 5- to 8-membered ring, provided that at least one of $R^1$ to $R^7$, $L^1$, $L^2$, $Q^1$, or $Q^2$ has at least one of a carboxy group or a salt thereof, a sulfo group or a salt thereof, a phosphono group or a salt thereof, an onio group selected from the group consisting of an ammonio group, a sulfonio group and a phosphonio group, or a polyamino acid residue, in a case where X is $CR^5$, where $R^5$ is a group represented by Formula (A), the ring pi and the ring $\beta_2$ are a 6-membered ring, and $L^1$ and $L^2$ are an arylene group, (a) there is no case in which $L^3$ is a single bond and Rill is an aryl group having a linear alkyl group having 18 or more carbon atoms, as a substituent, and (b) there is no case in which $L^3$ is arylene group and $R^{111}$ is a linear alkyl group having 18 or more carbon atoms, and in a case where X is $CR^5$, where $R^5$ is a group represented by Formula (A), the ring pi and the ring $\beta_2$ are a 6-membered ring, $L^1$ and $L^2$ are an arylene group, and $R^{111}$ has a substituent having a dipyrromethene boron complex structure, the dipyrromethene boron complex structure has a structure in which a dipyrromethene skeleton is coordinately bonded to a boron atom in a tridentate or tetradentate coordination, $$*L^3\text{-}R^{111}$$ Formula (A)

in the formula, $L^3$ represents a single bond or a linking group formed by combining one or two or more of an alkylene group, an arylene group, and a group represented by any one of Formulae (1-1) to (1-8), $R^{11}$ represents a hydrogen atom, an alkyl group, an alkenyl group, an alkynyl group, an aryl group, a heteroaryl group, or a monovalent aliphatic heterocyclic group, and

* represents a bonding portion,

Formula (1-1)

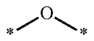

Formula (1-2)

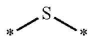

Formula (1-3)

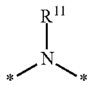

Formula (1-4)

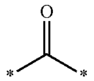

Formula (1-5)

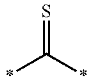

Formula (1-6)

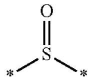

Formula (1-7)

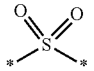

Formula (1-8)

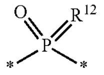

in the formula, $R^{11}$ and $R^{12}$ represent a hydrogen atom or a substituent, and

* represents a bonding portion.

2. The fluorescent compound according to claim 1, wherein both the $Q^1$ and the $Q^2$ are a group represented by Formula (1-1).

3. The fluorescent compound according to claim 1, wherein the X is $CR^5$, where $R^5$ is represented by Formula (A), and $L^3$ and $R^{111}$ in Formula (A) satisfy the following;

the $L^3$ is a single bond, the $R^{111}$ is a hydrogen atom, an alkyl group, an alkenyl group, an alkynyl group, an aryl group, or a heteroaryl group, or the $L^3$ is a group formed by combining one or two or more of an alkylene group, an arylene group, and a group represented by any one of Formulae (1-1) to (1-8), and the $R^{111}$ is a hydrogen atom.

4. The fluorescent compound according to claim 1, wherein at least one of the $R^3$ or the $R^4$ is a group containing a carboxy group or a salt thereof, a group containing a sulfo group or a salt thereof, a group containing a phosphono group or a salt thereof, a group containing an onio group selected from the group consisting of an ammonio group, a sulfonio group and a phosphonio group, or a group containing a polyamino acid residue.

5. The fluorescent compound according to claim 1, wherein at least one of the $R^3$ or the $R^4$ is a carboxy group or a salt thereof, a sulfo group or a salt thereof, or a phosphono group or a salt thereof.

6. The fluorescent compound according to claim 1, wherein at least one of the $R^3$ or the $R^4$ is a sulfo group or a salt thereof.

7. The fluorescent compound according to claim 1, wherein the $L^1$ and the $L^2$ are an alkylene group, an ethenylene group, an arylene group, a heteroarylene group, a cycloalkylene group, or a divalent aliphatic heterocyclic group, or a linking group formed by combining two of these groups, and the ring $\beta_1$ and the ring $\beta_2$ are a 6- to 8-membered ring.

8. The fluorescent compound according to claim 1, wherein the $Q^1$ and the $Q^2$ are a group represented by Formula (1-1), the $R^1$ to $R^4$ are represented by Formula (A), where the $L^3$ is a single bond or —$SO_3$—, and the $R^{111}$ is a hydrogen atom, the $R^6$ is represented by Formula (A), where the $L^3$ is a single bond, an arylene group or a group represented by Formula (1-1), or, a group formed by combining an arylene group and a group represented by Formula (1-1), and, the $R^{111}$ is a hydrogen atom or an alkyl group, the $R^7$ is a hydroxy group, the $L^1$ and the $L^2$ is an alkylene group or an arylene group, or, a group formed by combining an alkylene group and an arylene group, the ring $\beta_1$ and the ring $\beta_2$ are a 7-membered ring, the X is $CR^5$, where $R^5$ is represented by Formula (A), and the $L^3$ and the $R^{111}$ in Formula (A) satisfy the following (a) or (b);

(a) the $L^3$ is a single bond, and, the $R^{111}$ is an aryl group (b) the $L^3$ is an alkylene group, an arylene group, a group represented by Formula (1-1), a group represented by Formula (1-3), a group represented by Formula (1-4), or a group represented by Formula (1-7), or, a group formed by combining two or more of an alkylene group, an arylene group, a group represented by Formula (1-1), a group represented by Formula (1-3), a group represented by Formula (1-4), or a group represented by Formula (1-7), and, the $R^{111}$ is a hydrogen atom, wherein, in the fluorescent compound represented by Formula (1), at least one of the $R^3$ and the $R^4$ is a sulfo group or a salt thereof, or, at least one of the $R^1$ to $R^5$ includes two or more of a carboxy group or a salt thereof, a sulfo group or a salt thereof, a phosphono group or a salt thereof, an onio group selected from the group consisting of an ammonio group, a sulfonio group and a phosphonio group, or a polyamino acid residue, wherein, in the fluorescent compound represented by Formula (4), at least one of the $R^3$ and the $R^4$ is a sulfo group or a salt thereof, or, at least one of the $R^1$ to $R^7$ includes two or more of a carboxy group or a salt thereof, a sulfo group or a salt thereof, a phosphono group or a salt thereof, an onio group selected from the group consisting of an ammonio group, a sulfonio group and a phosphonio group, or a polyamino acid residue.

9. The fluorescent compound according to claim 1, wherein the fluorescent compound is represented by Formula (2) or Formula (5), Formula (2)

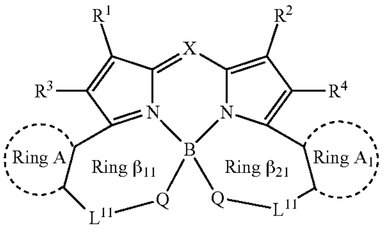

Formula (5)

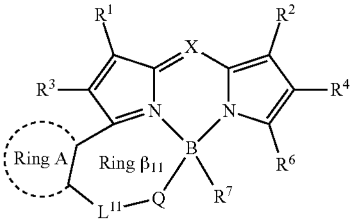

in the formula, X represents $CR^5$ or N, $R^1$ to $R^7$ and Q respectively have the same meanings as $R^1$ to $R^7$ and $Q^1$ in Formula (1) or (4), a ring A represents a hydrocarbon ring or a heterocycle, and $L^{11}$ represents a single bond or an alkylene group, an alkenylene group, an arylene group, a heteroarylene group, a cycloalkylene group, a divalent aliphatic heterocyclic group, or a group represented by any one of Formulae (1-1) to (1-8), or a linking group formed by combining two of these groups, where a ring $\beta_{11}$ and a ring $\beta_{21}$ are a 6- to 8-membered ring.

10. The fluorescent compound according to claim 1, wherein the fluorescent compound is represented by Formula (3) or Formula (6), Formula (3)

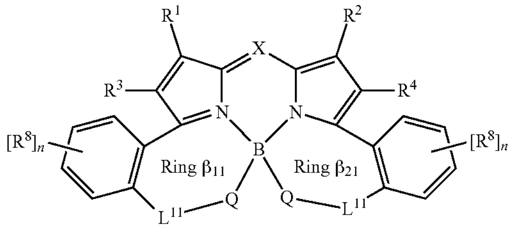

Formula (6)

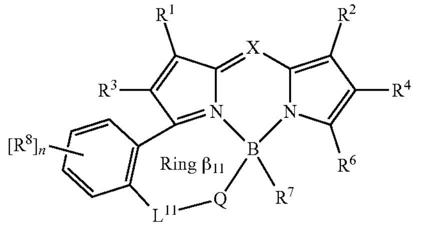

in the formula, X represents $CR^5$ or N, $R^1$ to $R^7$ and Q respectively have the same meanings as $R^1$ to $R^7$ and $Q^1$ in Formula (1) or (4), and $L^{11}$ has the same meaning as $L^{11}$ in Formula (2) or (5), and $R^8$ represents a substituent, and n is an integer of 0 to 4, where a ring $\beta_{11}$ and a ring $\beta_{21}$ are a 6- to 8-membered ring.

11. The fluorescent compound according to claim 10, wherein the fluorescent compound is represented by Formula (3), wherein the X is $CR^5$, where $R^5$ is represented by Formula (A) and the $L^3$ in Formula (A) is a single bond, an alkylene group, an arylene group, a group represented by Formula (1-1), a group represented by Formula (1-3), a group represented by Formula (1-4), or a group represented by Formula (1-7), or, a group formed by combining two or more of an alkylene group, an arylene group, a group represented by Formula (1-1), a group represented by Formula (1-3), a group represented by Formula (1-4), or a group represented by Formula (1-7), and, the Rill in Formula (A) is a hydrogen atom or an aryl group, the $R^1$ and $R^2$ are a hydrogen atom, the $R^3$ and $R^4$ are represented by Formula (A), where the $L^3$ is a single bond or —$SO_3$—, and the $R^{111}$ is a hydrogen atom, the Q is a group represented by Formula (1-1), the $L^{11}$ is a methylene group, the $R^8$ bonds only at the meta position on the side opposite to the pyrrole ring with respect to the bonding position with $L^{11}$, and is an alkoxy group or a halogen atom, and n is 0 or 1, in the case where n is 0, at least one of the $R^1$ to $R^5$, $L^{11}$, and Q includes a carboxy group or a salt thereof, a sulfo group or a salt thereof, and, in the case where n is 1, at least one of the $R^1$ to $R^5$, $R^8$, $L^{11}$, and Q includes a carboxy group or a salt thereof, a sulfo group or a salt thereof, wherein at least one of the $R^3$ and $R^4$ is a sulfo group or a salt thereof, or, at least one of the $R^1$ to $R^5$ includes two or more of a carboxy group or a salt thereof, a sulfo group or a salt thereof, a phosphono group or a salt thereof, an onio group selected from the group consisting of an ammonio group, a sulfonio group and a phosphonio group, or a polyamino acid residue in the case where n is 0, or at least one of the $R^1$ to $R^5$ and $R^8$ includes two or more of a carboxy group or a salt thereof, a sulfo group or a salt thereof, a phosphono group or a salt thereof, an onio group selected from the group consisting of an ammonio group, a sulfonio group and a phosphonio group, or a polyamino acid residue in the case where n is 1.

12. The fluorescent compound according to claim 1, wherein the fluorescent compound is represented by Formula (7) or Formula (8), Formula (7)

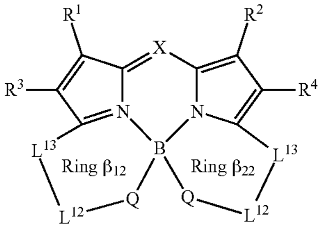

Formula (8)

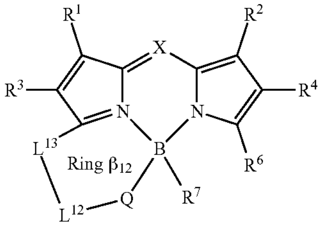

in the formula, X represents $CR^5$ or N, $R^1$ to $R^7$ and Q respectively have the same meanings as $R^1$ to $R^7$ and $Q^1$ in Formula (1) or (4), $L^{12}$ represents a single bond or an alkylene group, an alkenylene group, an arylene group, a heteroarylene group, a cycloalkylene group, a divalent aliphatic heterocyclic group, or a group represented by any one of Formulae (1-1) to (1-8), or a linking group formed by combining two of these groups, and $L^{13}$ represents a methylene group or a group represented by any one of Formulae (1-1) to (1-8), where a ring $\beta_{12}$ and a ring $\beta_{22}$ are a 5- to 8-membered ring.

13. The fluorescent compound according to claim 12, wherein the fluorescent compound is represented by Formula (7), wherein the Q is a group represented by Formula (1-1), the $R^1$ and the $R^2$ are a hydrogen atom, the $R^3$ and $R^4$ are represented by Formula (A), where the $L^3$ is a single bond or —$SO_3$—, and the $R^{111}$ is a hydrogen atom, the $L^{12}$ is an alkylene group, the $L^{13}$ is a methylene group, or a group represented by Formula (1-3), the ring $\beta_{12}$ and the ring $\beta_{22}$ are a 7-membered ring, the X is $CR^5$, where $R^5$ is represented by Formula (A), and the $L^3$ and the $R^{111}$ in Formula (A) satisfy the following (a) or (b);

(a) the $L^3$ is a single bond, and, the $R^{111}$ is an aryl group (b) the $L^3$ is an alkylene group, an arylene group, a group represented by Formula (1-1), a group represented by Formula (1-3), a group represented by Formula (1-4), or a group represented by Formula (1-7), or, a group formed by combining two or more of an alkylene group, an arylene group, a group represented by Formula (1-1), a group represented by Formula (1-3), a group represented by Formula (1-4), or a group represented by Formula (1-7), and, the $R^{111}$ is a hydrogen atom.

14. The fluorescent compound according to claim 1, wherein the fluorescent compound is represented by Formula (9), Formula (9)

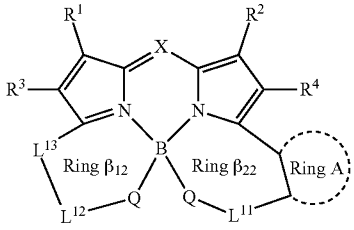

in the formula, X represents $CR^5$ or N, $R^1$ to $R^5$ and Q respectively have the same meanings as $R^1$ to $R^5$ and $Q^1$ in Formula (1) or (4), $L^{11}$ and $L^{12}$ represent a single bond or an alkylene group, an alkenylene group, an arylene group, a heteroarylene group, a cycloalkylene group, a divalent aliphatic heterocyclic group, or a group represented by any one of Formulae (1-1) to (1-8), or a linking group formed by combining two of these groups, $L^{13}$ represents a methylene group or a group represented by any one of Formulae (1-1) to (1-8), and a ring A represents a hydrocarbon ring or a heterocycle, and where a ring $\beta_{12}$ is a 5- to 8-membered ring, and a ring $\beta_{21}$ is a 6- to 8-membered ring.

15. The fluorescent compound according to claim 1, wherein at least one of $R^1$ to $R^8$, $L^1$, $L^2$, $L^{11}$ to $L^{13}$, Q, $Q^1$, or $Q^2$ has a moiety bondable to a biological substance.

16. A fluorescent labeled biological substance, which is obtained through bonding between the fluorescent compound according to claim 15 and a biological substance.

17. The fluorescent labeled biological substance according to claim 16, wherein the biological substance is any one of a protein, a peptide, an amino acid, a nucleic acid, a sugar chain, or a lipid.

18. The fluorescent labeled biological substance according to claim 16, wherein the bonding between the fluorescent compound and the biological substance is formed by any one of the followings i) to v), i) non-covalent or covalent bond between peptides, ii) Van der Waals interaction between a long-chain alkyl group in a fluorescent compound and a lipid bilayer or lipid in a biological substance, iii) an amide bond formed by reacting an N-hydroxysuccinimide ester in a fluorescent compound with an amino group in a biological substance, iv) a thioether bond formed by reacting a maleimide group in a fluorescent compound with a sulfanyl group in a biological substance, and v) a bond with a formation of a triazole ring, which is formed by Click reaction between an azido group in a fluorescent compound and an acetylene group in a biological substance, or between an acetylene group in a fluorescent compound and an azido group in a biological substance.

* * * * *